US012241085B2

(12) United States Patent
Sances et al.

(10) Patent No.: US 12,241,085 B2
(45) Date of Patent: Mar. 4, 2025

(54) HUMAN PLURIPOTENT STEM CELL DERIVED NEURODEGENERATIVE DISEASE MODELS ON A MICROFLUIDIC CHIP

(71) Applicant: CEDARS-SINAI MEDICAL CENTER, Los Angeles, CA (US)

(72) Inventors: Samuel Sances, Santa Monica, CA (US); Alexander Laperle, North Hollywood, CA (US); Nur Yucer, Los Angeles, CA (US); Clive N. Svendsen, Pacific Palisades, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 1196 days.

(21) Appl. No.: 17/041,672

(22) PCT Filed: Apr. 5, 2019

(86) PCT No.: PCT/US2019/026178
§ 371 (c)(1),
(2) Date: Sep. 25, 2020

(87) PCT Pub. No.: WO2019/195798
PCT Pub. Date: Oct. 10, 2019

(65) Prior Publication Data
US 2021/0130774 A1    May 6, 2021

Related U.S. Application Data

(60) Provisional application No. 62/816,785, filed on Mar. 11, 2019, provisional application No. 62/755,282, (Continued)

(51) Int. Cl.
*C12N 5/079*     (2010.01)
*C12M 1/12*      (2006.01)
(Continued)

(52) U.S. Cl.
CPC .......... *C12N 5/0622* (2013.01); *C12M 23/16* (2013.01); *C12M 25/02* (2013.01); *C12M 41/46* (2013.01);
(Continued)

(58) Field of Classification Search
CPC .. C12N 5/0622; C12N 5/0619; C12N 5/0696; C12N 5/0697; C12N 2502/081; C12N 2502/086; C12N 2506/45
See application file for complete search history.

(56) References Cited

U.S. PATENT DOCUMENTS 6,300,080 B1    10/2001    Brenner et al.
7,989,197 B2    8/2011    Yoo et al.
(Continued)

FOREIGN PATENT DOCUMENTS

AU    2015204375 A1    8/2015
AU    2016341880 A1    5/2018
(Continued)

OTHER PUBLICATIONS

EP 19771249.0 Partial Supplemental European Search Report dated Nov. 8, 2011, 15 pages.
(Continued)

*Primary Examiner* — Kara D Johnson
(74) *Attorney, Agent, or Firm* — NIXON PEABODY LLP

(57) ABSTRACT

Described herein is a microphysiological system for models of disease. Specifically, induced pluripotent stem cells (iPSCs) and iPSC-derived cells, including those obtained from disease patients, are seeded onto microfluidic "chip" devices to study cellular development and disease pathogenesis. Herein, neurodegenerative disease modeling, including Parkinson's Disease (PD) is shown to reproduce key PD pathology in a vascularized human model that contains neurons relating to PD pathology. Such compositions and
(Continued)

methods are used for research for PD biomarkers, patient screening for PD risk assessment, and therapeutic discovery and testing. A panel of biomarkers are generated through analysis of living PD-chips by neural activity, whole transcriptomic, proteomic, and metabolomic analysis, and functional enzyme tests of media and tissue. Introducing therapeutics through a vasculature channel, coupled with blood brain barrier penetration studies can be assessed for efficacy in the human neural cells present in the PD-Chip.

9 Claims, 57 Drawing Sheets

Related U.S. Application Data filed on Nov. 2, 2018, provisional application No. 62/653,697, filed on Apr. 6, 2018.

(51) Int. Cl.
| | | |
|---|---|---|
| *C12M 1/34* | (2006.01) | |
| *C12M 3/06* | (2006.01) | |
| *C12N 5/071* | (2010.01) | |
| *C12N 5/074* | (2010.01) | |
| *C12N 5/0793* | (2010.01) | |
| *G01N 33/50* | (2006.01) | |

(52) U.S. Cl.
CPC ......... *C12N 5/0619* (2013.01); *C12N 5/0696* (2013.01); *C12N 5/0697* (2013.01); *G01N 33/5058* (2013.01); *C12N 2502/081* (2013.01); *C12N 2502/086* (2013.01); *C12N 2502/45* (2013.01); *C12N 2506/45* (2013.01)

(56) References Cited

U.S. PATENT DOCUMENTS

| | | |
|---|---|---|
| 8,647,861 B2 | 2/2014 | Ingber et al. |
| 9,790,470 B2 | 10/2017 | Vallier et al. |
| 10,174,289 B2 | 1/2019 | Wells et al. |
| 11,326,149 B2 | 5/2022 | Kerns et al. |
| 2004/0247571 A1 | 12/2004 | Meijer et al. |
| 2007/0077649 A1 | 4/2007 | Sammak et al. |
| 2007/0128722 A1 | 6/2007 | Lin |
| 2007/0281353 A1 | 12/2007 | Vacanti et al. |
| 2008/0044847 A1 | 2/2008 | Shusta et al. |
| 2008/0132445 A1 | 6/2008 | Ormandy et al. |
| 2008/0305086 A1 | 12/2008 | Poole |
| 2009/0075374 A1 | 3/2009 | Palecek et al. |
| 2009/0123383 A1 | 5/2009 | Frangioni |
| 2009/0214649 A1 | 8/2009 | Gazit et al. |
| 2009/0258337 A1 | 10/2009 | Yagi |
| 2009/0317852 A1 | 12/2009 | Parker et al. |
| 2009/0324559 A1 | 12/2009 | Sakurada et al. |
| 2010/0136690 A1 | 6/2010 | Sundstorm et al. |
| 2011/0064700 A1 | 3/2011 | Cardozo et al. |
| 2011/0097796 A1 | 4/2011 | Loa |
| 2011/0111499 A1 | 5/2011 | Torihashi |
| 2011/0245307 A1 | 10/2011 | Alkon |
| 2011/0250585 A1 | 10/2011 | Ingber et al. |
| 2012/0094381 A1 | 4/2012 | Chambers et al. |
| 2012/0107934 A1 | 5/2012 | Poole |
| 2012/0128655 A1 | 5/2012 | Kim et al. |
| 2012/0171354 A1 | 7/2012 | O'Neill et al. |
| 2012/0211373 A1 | 8/2012 | El-Sayed et al. |
| 2013/0137130 A1 | 5/2013 | Wells et al. |
| 2013/0224857 A1 | 8/2013 | Blak et al. |
| 2013/0280802 A1 | 10/2013 | Schulz et al. |
| 2013/0288969 A1 | 10/2013 | Scadden |
| 2014/0038279 A1 | 2/2014 | Ingber et al. |
| 2014/0065660 A1 | 4/2014 | Hanseup et al. |
| 2014/0093905 A1 | 4/2014 | Ingber et al. |
| 2014/0134732 A1 | 5/2014 | Ashton |
| 2014/0142370 A1 | 5/2014 | Wong et al. |
| 2014/0171380 A1 | 6/2014 | Kim et al. |
| 2014/0199700 A1 | 7/2014 | Kume et al. |
| 2014/0248621 A1 | 9/2014 | Collins |
| 2014/0288093 A1 | 9/2014 | Krainc et al. |
| 2014/0315990 A1 | 10/2014 | Alkon et al. |
| 2014/0329321 A1 | 11/2014 | Rajesh et al. |
| 2014/0342445 A1 | 11/2014 | Ingber et al. |
| 2015/0017674 A1 | 1/2015 | Christensen et al. |
| 2015/0023928 A1 | 1/2015 | Hassiotou |
| 2015/0037320 A1 | 2/2015 | McGrath et al. |
| 2015/0151011 A1 | 6/2015 | Jang et al. |
| 2015/0218522 A1 | 8/2015 | Peterson et al. |
| 2015/0232810 A1 | 8/2015 | Luo et al. |
| 2015/0252328 A1 | 9/2015 | Woodruff et al. |
| 2015/0258124 A1 | 9/2015 | Katajisto et al. |
| 2015/0265652 A1 | 9/2015 | George et al. |
| 2015/0329828 A1 | 11/2015 | Rezania |
| 2016/0145642 A1 | 5/2016 | Cui et al. |
| 2016/0152950 A1 | 6/2016 | Zhang et al. |
| 2016/0175401 A1 | 6/2016 | Spiegelman et al. |
| 2017/0107498 A1 | 4/2017 | Sareen et al. |
| 2017/0226478 A1 | 8/2017 | Kerns et al. |
| 2017/0240866 A1 | 8/2017 | Wells et al. |
| 2017/0253856 A1 | 9/2017 | Douvaras et al. |
| 2017/0283772 A1 | 10/2017 | Qian et al. |
| 2017/0292116 A1 | 10/2017 | Erlls et al. |
| 2017/0313976 A1 | 11/2017 | Kuwahara et al. |
| 2018/0021383 A1 | 1/2018 | George et al. |
| 2018/0057788 A1 | 3/2018 | Kerns et al. |
| 2018/0237741 A1 | 8/2018 | Gazit et al. |
| 2018/0298331 A1 | 10/2018 | Kerns et al. |
| 2018/0298332 A1 | 10/2018 | Kerns et al. |
| 2018/0305651 A1 | 10/2018 | Kerns et al. |
| 2018/0305668 A1 | 10/2018 | Gazit et al. |
| 2019/0009270 A1 | 1/2019 | Gazit et al. |
| 2019/0018000 A1 | 1/2019 | Gazit et al. |
| 2019/0031992 A1 | 1/2019 | Kerns et al. |
| 2019/0153395 A1 | 5/2019 | Barrett et al. |
| 2019/0194606 A1 | 6/2019 | Vatine et al. |
| 2019/0359924 A1 | 11/2019 | Kerns et al. |
| 2020/0000267 A1 | 1/2020 | Zuidervaart et al. |
| 2020/0002671 A1 | 1/2020 | Qu et al. |
| 2020/0032215 A1 | 1/2020 | Svendsen et al. |
| 2020/0071673 A1 | 3/2020 | Sareen et al. |
| 2020/0157508 A1 | 5/2020 | Barrett et al. |
| 2021/0000880 A1 | 1/2021 | Svendsen et al. |
| 2021/0023039 A1 | 1/2021 | Laperle et al. |
| 2021/0024886 A1 | 1/2021 | Laperle et al. |
| 2021/0033628 A1 | 2/2021 | Laperle et al. |
| 2021/0130774 A1 | 5/2021 | Sances et al. |
| 2023/0159896 A1 | 5/2023 | Sharma et al. |
| 2024/0067933 A1 | 2/2024 | Laperle et al. |
| 2024/0076629 A1 | 3/2024 | Laperle et al. |

FOREIGN PATENT DOCUMENTS

| | | |
|---|---|---|
| AU | 2017213795 A1 | 8/2018 |
| AU | 2017214468 A1 | 9/2018 |
| AU | 2017319168 A1 | 3/2019 |
| AU | 2017321489 A1 | 3/2019 |
| AU | 2018235950 A1 | 10/2019 |
| AU | 2018236273 A1 | 10/2019 |
| AU | 2018270270 A1 | 12/2019 |
| AU | 2017319168 B2 | 4/2021 |
| AU | 2016341880 B2 | 5/2021 |
| CA | 3002399 A1 | 4/2017 |
| CA | 3013337 A1 | 8/2017 |
| CA | 3013357 A1 | 8/2017 |
| CA | 3034614 A1 | 3/2018 |
| CA | 3035058 A1 | 3/2018 |
| CA | 3055992 A1 | 9/2018 |
| CA | 3056089 A1 | 9/2018 |
| CA | 3064086 A1 | 11/2018 |
| EP | 3008168 A1 | 4/2016 |
| EP | 3031908 A1 | 6/2016 |
| EP | 3365424 | 8/2018 |
| EP | 3411470 A2 | 12/2018 |
| EP | 3411472 A1 | 12/2018 |

(56) References Cited

FOREIGN PATENT DOCUMENTS

| | | |
|---|---|---|
| EP | 3503901 A1 | 7/2019 |
| EP | 3504319 A1 | 7/2019 |
| EP | 3625331 A1 | 3/2020 |
| EP | 3768823 | 1/2021 |
| EP | 3775161 | 2/2021 |
| EP | 3787613 | 3/2021 |
| EP | 3787649 A1 | 3/2021 |
| GB | 2561312 A | 10/2018 |
| GB | 2562406 A | 11/2018 |
| GB | 2564582 A | 1/2019 |
| GB | 2568446 A | 5/2019 |
| GB | 2569058 A | 6/2019 |
| GB | 2574988 A | 12/2019 |
| GB | 2575574 A | 1/2020 |
| GB | 2561312 B | 3/2021 |
| GB | 2564582 B | 9/2021 |
| HK | 1260726 B | 7/2021 |
| JP | 2003-511346 | 9/2000 |
| JP | 2014-171434 | 9/2014 |
| JP | 2014-171434 A | 9/2014 |
| JP | 2015-504676 A | 2/2015 |
| JP | 2015504676 | 2/2015 |
| JP | 2018533940 A | 11/2018 |
| JP | 2019506861 A | 3/2019 |
| JP | 2021-520784 A | 8/2021 |
| JP | 2021-523700 A | 9/2021 |
| JP | 2021-523888 A | 9/2021 |
| KR | 20180069882 A | 6/2018 |
| SG | 11201803143Y A | 5/2018 |
| SG | 11201901621V A | 3/2019 |
| SG | 11201901628X A | 3/2019 |
| SG | 11201908358P A | 10/2019 |
| SG | 11201908359U A | 10/2019 |
| WO | 2000053218 | 9/2000 |
| WO | 2005021720 A2 | 3/2005 |
| WO | WO 2010009307 A1 | 1/2010 |
| WO | WO 2010/108005 A2 | 9/2010 |
| WO | 2011109440 A1 | 9/2011 |
| WO | 2012/100084 A1 | 7/2012 |
| WO | WO 2012/118799 A2 | 9/2012 |
| WO | 2013/056216 A1 | 4/2013 |
| WO | 2013/071282 A1 | 5/2013 |
| WO | WO 2013/065763 A1 | 5/2013 |
| WO | 2013/086486 A1 | 6/2013 |
| WO | WO2013106677 A1 | 7/2013 |
| WO | 2013/184193 A1 | 12/2013 |
| WO | WO 2014/172682 A1 | 10/2014 |
| WO | WO 2014/176606 A1 | 10/2014 |
| WO | WO 2014159356 A1 | 10/2014 |
| WO | WO 2015/052143 A1 | 4/2015 |
| WO | WO 2015/057261 A1 | 4/2015 |
| WO | WO 2015/126528 A1 | 8/2015 |
| WO | 2015143342 A1 | 9/2015 |
| WO | WO 2015/138032 A2 | 9/2015 |
| WO | WO 2015/138034 A2 | 9/2015 |
| WO | WO 2015/163823 A1 | 10/2015 |
| WO | WO 2015153451 A1 | 10/2015 |
| WO | WO 2015/181253 A1 | 12/2015 |
| WO | WO 2015/183920 A2 | 12/2015 |
| WO | WO 2015/188131 A1 | 12/2015 |
| WO | 2016061464 A1 | 4/2016 |
| WO | 2016063985 A1 | 4/2016 |
| WO | 2016093222 A | 6/2016 |
| WO | WO 2016/086040 A1 | 6/2016 |
| WO | 2016/141137 A1 | 9/2016 |
| WO | 2016162747 A2 | 10/2016 |
| WO | 2016183252 A1 | 11/2016 |
| WO | WO 2017/035119 A1 | 3/2017 |
| WO | WO-2017070224 A1 * | 4/2017 ........ B01L 3/502715 |
| WO | 2017075271 A1 | 5/2017 |
| WO | 2017078807 A1 | 5/2017 |
| WO | 2017/112455 A1 | 6/2017 |
| WO | WO 2017/123806 A1 | 7/2017 |
| WO | WO 2017/136462 A2 | 8/2017 |
| WO | WO 2017/136479 A1 | 8/2017 |
| WO | WO 2017/143049 A1 | 8/2017 |
| WO | WO 2017/200486 A1 | 11/2017 |
| WO | 2017/219000 A1 | 12/2017 |
| WO | 2018/035214 A1 | 2/2018 |
| WO | WO 2018/044934 A1 | 3/2018 |
| WO | WO-2018044885 A1 * | 3/2018 ............ A61K 35/30 |
| WO | 2018/140647 A1 | 8/2018 |
| WO | 2018/176001 A1 | 9/2018 |
| WO | WO 2018/170139 A1 | 9/2018 |
| WO | WO 2018/170180 A1 | 9/2018 |
| WO | WO 2018/213773 A1 | 11/2018 |
| WO | 2019/122291 A2 | 6/2019 |
| WO | 2019/178550 A1 | 9/2019 |
| WO | 2019169351 A1 | 9/2019 |
| WO | WO 2019/183597 A1 | 9/2019 |
| WO | 2019195798 A1 | 10/2019 |
| WO | 2019195800 A1 | 10/2019 |
| WO | 2019212690 A1 | 11/2019 |
| WO | 2019212691 A1 | 11/2019 |
| WO | 2021/081237 A1 | 4/2021 |
| WO | 2021081229 A1 | 4/2021 |
| WO | 2021222724 A1 | 11/2021 |

OTHER PUBLICATIONS

EP 18802136.4 Examination Report dated Oct. 14, 2021, 8 pages.
Abbott et al., Structure and function of the blood-brain barrier, Neurobiology of Desease, 2010 27:13-25.
Abbott et al., Structure and function of the blood-brain barrier, Pharm Tox BBB: Feb. 1-3, 2010, Conf. Abstract.
Demers et al., Development-on-Chip: in vitro Neutral Tube Patterning with a Microfluidic Device, Development, 2016, vol. 143(11), pp. 1884-1892.
Kauffman et al., Alternative functional in vitro models of human intestinal epithelia, frontiers in Pharmacology, Jul. 2013, vol. 4, Article 79, 18 pages.
Kelamangalath et al. k-Opioid receptor inhibition of calcium oscillations in spinal cord neurons,, Molecular Pharmacology, 2011, 79:1061-1071.
Kwasny et al., Static biofilm cultures of gram-positive pathogens grown in a microtiter format used for anti-biofilm drug discovery, Current Protocols in Pharmacology, 2010, 13A.8.1-13A.8.23.
Loo et al., An Arduous Journey from Human Pluripotent Stem Cells to Functional Pancreatic Beta Cells, Diabetes Obes Metab., 2018, vol. 20(3), pp. 3-13.
McGaugh et al., Efficient Differentiation of Pluripotent Stem Cells to NKX6-1 + Pancreating Progenitors, Journal of Visualized Experiments, 2017, vol. 121, pp. 1-5.
Naik et al., In vitro blood-brain models: Current and perspective technologies, J. Phar Sci., 2012, 1014(4):1337-1354.
Perry et al., The Neuromuscular junction: Structure and function, downloaded from the internet (Neuromuscular junction: Parts, structure and steps/Kenhub>, pp. 1-6, downloaded 2.25.21.
Polydimethylsiloxane—Wikipedia, dowloaded on Feb. 24, 2021 <Silicon dioxide—Wikipedia>, pp. 1-11.
Ryan et al., Progranulin is expressed within motor neurons and promotes neuronal cell survival, BMC Neuroscience, 2009, 10:130, pp. 1-22.
Sances et al., Modeling ALS with Motor Neurons Derived from Human Induced Pluripotent Stem Cells, Nature Neuroscience, 2016, vol. 19, pp. 542-553.
Santaguida et al., Side By Side Comparison Between Dynamic Versus Static Models of Blood-Brain-Barrier in vitro: A Permeability Study, Brain Research, 2006, vol. 1109(1), pp. 1-13.
Schiesser et al., Derivation of Insulin-Producing Beta-Cells from Human Pluripotent Stem Cells, The Review of Diabetic Studies, 2014, vol. 11(1), pp. 6-18.
Schwartz et al., Allan-Herndon-Dudley Syndrome and the Monocarboxylate Transporter 8 (MCT8) Gene, 2005, AJHG, vol. 77(1), pp. 41-53.
Silicon dioxide—Wikipedia, downloaded on Feb. 24, 2021 <silicon dioxide—Wikipedia> pp. 1-20.

(56) References Cited

OTHER PUBLICATIONS

Southam et al., Microfluidic primary culture model of the lower motor neuron-neuromuscular junction circuit, J Neurosc Meth 2013, 218:164-169.
Southam et al., A Novel in vitro Primary Culture Model of the Lower Motor Neuron -Nueromuscular Junction Circuit, Microfludic and Compartmentalized Platforms for Neurobiological Research, Humana Press, 2015, pp. 181-193, abstract only.
Uzei et al., Microfluidic Device for the Formation of Optically Excitable, Three-Dimensional, Compartmentalized Motor Units, Science Advances, 2016, pp. e1501429.
Wang et al., Microfluidics: A new cosset for neurobiology, Lab Chip, 2009, 9:644-652.
Wang et al., Generation of an Induced Pluripotent Stem Cell Line (SHCDNi003-A) from a One-Year Old Chinese Han Infant with Allan-Herndon-Dudley Syndrome, Stem Cell Research, 2020, vol. 46, 4 pages.
Yang et al., From the vascular microenvironment to neurogenesis, Brain Res Bull. Jan. 15, 2011; 84(1):1-7.
International Search Report and Written Opinion for PCT/US2018/015318 May 2, 2018, 16 pages.
International Search Report and Written Opinion for PCT/US2018/024198 dated Aug. 13, 2018, 15 pages.
International Search Report and Written Opinion for PCT/US2020/056896 dated Oct. 22, 2020, 11 pages.
International Search Report and Written Opinion for PCT/US2020/056906 dated Mar. 16, 2021, 13 pages.
International Preliminary Report on Patentability for PCT/US2018/015318 dated Jul. 30, 2019, 12 pages.
International Preliminary Report on Patentability for PCT/US2018/024198 dated Feb. 25, 2020, 12 pages.
EP 19782199.4 Extended European Search Report dated Mar. 3, 2022, 12 pages.
EP 19796911.6 Extended Search Report dated Apr. 29, 2022, 15 pages.
Akhtar et al., Inducible Expression of GDNF in Transplanted iPSC-Derived Nueral Progenitor Cells, Stem Cell Reports, 2018, vol. 10, pp. 1696-1704.
Araoka, et al., Efficient and rapid induction of human iPSCs/ESCs into nephrogenic intermediate mesoderm using small molecule-based differentiation methods, PLoS One, 2014, 9(1), 14 pages.
Badger et al., Parkinson's disease in a dish Using stem cells as a molecular tool. Neuropharmacology, 2014, vol. 76, pp. 88-96.
Bai et al., BMP-2, VEGF and bFGF Synergistically Promote the Osteogenic Differentiation of Rat Bone Marrow-Derived Mesenchymal Stem Cells, Biotechnol Lett, 2013, vol. 35, pp. 301-308.
Bar-Am et al., Regulation of protein kinase C by the anti-Parkinson drug, MAO-B inhibitor, rasagiline and its derivatives, in vivo, Journal of Neurochemistry, 2004, vol. 89, No. 5, pp. 1119-1125.
Bohrsen et al. Supportive angiogenic and osteogenic differentiation of mesenchymal stromal cells and endothelial cells in monolayer and co-cultures. International Journal of Oral Science (2016) 8, 223-230 (Year: 2016).
Chen, et al., Chemically defined conditions for human iPSC derivation and culture, 2011, Nat. Methods, 8(5), 8 pages.
Cooper et al., Differentiation of human ES and Parkinson's disease iPS cells into ventral midbrain dopaminergic neurons requires a high activity form of SHH, FGF8a and specific regionalization by retinoic acid, Molecular and Cellular Neurosciences, 2010, vol. 45, No. 3, pp. 258-266.
Farrelly et al., Extracellular matrix regulates apoptosis in mammary epithelium through a control on insulin signaling, The Journal of Cell Biology, 1999, 144(6):1337-1347.
Gurusamy et al., Hepatocyte Growth Factor-Like Protein is a Positive Regulator of Early Mammary Gland Ductal Morphogenesis, Mechanisms of Development, 2014, vol. 133, pp. 11-22.
Hens et al., BMP4 and PTHrP interact to stimulate ductal outgrowth during embryonic mammary development and to Inhibit hair follicle induction, Development, 2017, 134:1221-1230.

Ichida et al., Probing disorders of the nervous system using reprogramming approaches, The EMBO Journal/European Molecular Biology Organization, 2015, vol. 34, No. 11, pp. 1456-1477.
Kessler et al., The Notch and Wnt pathways Regulate Stemness and Differentiation in Human Fallopian Tube Organoids, Nature Communications, 2015, vol. 6, p. 8989.
Kim et al. A practical guide to microfluidic perfusion culture of adherent mammalian cells. Lab Chip, 2007, 7, 681-694 (Year: 2007).
Kim et al. Shear Stress Induced by an Interstitial Level of Slow Flow Increases the Osteogenic Differentiation of Mesenchymal Stem Cells through TAZ Activation. PLoS ONE 9(3): e92427. p. 1-9 (Year: 2014).
Kreke et al. Effect of Intermittent Shear Stress on Mechanotransductive Signaling and Osteoblastic Differentiation of Bone Marrow Stromal Cells. Tissue Engineering: Part A vol. 14, No. 4, 2008. p. 529-537 (Year: 2008).
Levanon, et al., Primary ex vivo cultures of human fallopian tube epithelium as a model for serous ovarian carcinogenesis, Oncogene, 2010, 29(8):1103-1113.
Maegawa et al. Enhancement of osteoblastic differentiation of mesenchymal stromal cells cultured by selective combination of bone morphogenetic protein-2 (BMP-2) and fibroblast growth factor-2 (FGF-2). J Tissue Eng Regen Med 2007; 1: 306-313 (Year: 2007) Abstract Only.
Nishimura et al. Effect of osteogenic differentiation medium on proliferation and differentiation of human mesenchymal stem cells in threedimensional culture with radial flow bioreactor. Regenerative Therapy 2 (2015) 24-31 (Year: 2015).
O'Neill et al., Genetic disorders coupled to ROS deficiency, Redox Biology, 6: 135-156. (Year: 2015).
Qu et al., Differentiation of human induced pluripotent stem cells to mammary-like organoids, Stem Cell Reports, 2017, 8(2):205-215.
Rey, et al., Chapter 7, Sexual Differentiation, 2016 [online]. [Retrieved on Sep. 19, 2019]. Retrieved from the Internet <URL:https://www.endotext.org/wp-content/uploads/pdfs/sexual-differentiation.pdf>, 89 pages.
Ryan et al., Isogenic Human iPSC Parkinson's Model Shows Nitrosative Stress-Induced Dysfunction in MEF2-PGCI [alpha] Trans, Cell, Elsevier, 2013, vol. 155, No. 6, pp. 1351-1364.
Sanchez-Danes et al., Disease-specific phenotypes in dopamine neurons from human iPS-based models of genetic and sporadic Parkinson's disease, EMBO Molecular Medicine, 2015, vol. 4, No. 5, pp. 380-395.
Simeone et al., The Otx Family, Pattern Formation and Development Mechanisms, 2002, vol. 12, pp. 409-415.
Sun et al., Role of Bone Morphogenetic Protein-2 in Osteogenic Differentiation of MesenChymal Stem Cells, Molecular Medicine Reports, 2015, vol. 12, pp. 4230-4237.
Vogel et al., Co-culture of human induced pluripotent stem cells 9iPSCs) with human fallopian tube epithelium (FTE) Induces Pax8 and CK7 expression: Initial steps in modeling fallopian tube epithelium to study serous carcinogenesis; Gynecologic Oncology, 2015 137(1):206.
Zhang et al., Regulation and Patterning of Cell Differentiation and Pluripotency, Thesis, Columbia University, pp. 1-177, 2011.
Zhang et al., FGF Ligands of the Postnatal Mammary Stroma Regulate Distinct Aspects of Epithelial Morphogenesis, Stem Cells and Regeneration, 2014, vol. 141, pp. 3352-3362.
Zhou et al., Rapid and efficient generation of transgene-free iPSC from a small volume of cryopreserved blood, Stem Cell Reviews and Reports 11: 652-665. (Year: 2015).
EP 19782199.4 Partial Supplementary Search Report dated Nov. 30, 2021, 15 pages.
EP 19796470.3 European Extended Search Report dated Dec. 10, 2021, 11 pages.
Burkhardt et al., A Cellular Model for Sporadic ALS using Patient-Derived Induced Pluripotent Stem Cells, Molecular and Cellular Neuroscience, 2013, vol. 56, pp. 355-364.
Kitamura et al., Possible Involvement of Both Mitochondria and Endoplasmic Reticulum-Dependent Caspase Pathways in Retenone-Induced Apoptosis in Human Neuroblastoma SH-SY5Y Cells, Neuroscience Letters, 2002, vol. 2002, pp. 25-28.

(56) References Cited

OTHER PUBLICATIONS

Lenzi et al., Differentiation of Control and ALS Mutant Human iPSCs into Functional Skeletal Muscle Cells, A Tool for the Study of Neuromuscolar Diseases, Stem Cell Research, 2016, vol. 17, pp. 140-147.

Tian et al., Salvianolic Acid B, An Antioxidant from Saliva Miltiorrhiza, prevents 6-hydroxydopamine Induced Apoptosis In SH-SY5Y Cells, The International Science Journal of Biochemistry & Cell Biology, 2008, vol. 40, pp. 409-422.

Wu et al., Nuclear Accumulation of Histone Deacetylase 4 (HDAC4) Exerts Neurotoxicity in Models of Parkinson's Disease, Moi Neurobiol, 2017, vol. 54, pp. 6970-6983.

Arendt et al., Form and Function: how Estrogen and Progesterone Regulate the Mammary Epithelial Hierarchy, J. Mammary Gland Biol Neoplasia, 2015, 20:9-25.

Qiao et al., AP2y regulates neural and epiderman development downstream of the BMP pathway at early stages of ectodermal patterning, Cell Research, 2012, 22:1546-1561.

Lin et al., Embryoid body formation from human pluripotent stem cells in chemically defined E8 media, StemBook, ed, Jun. 1, 2014.

JP Reasons for Rejection—2020-560893 dated Feb. 6, 2023, 9 pages.

Matsumoto et al., Functional neurons generated from T Cell-derived induced pluripotent stem cells for neurological disease modeling, 2016, 6:422-435.

Moors et al., Therapeutic potential of autophagy-enhancing agents in Parkinson's disease, Molecular Neurodegeneration, 2017, 12:11, p. 1-18.

Okita et al., An efficient nonviral method to generate integration-free human-induced pluripotent stem cells from cord blood and peripheral blood cells, Stem Cells 2013, 31:458-466.

Kondo et al., iPSC-Based compound screening and in vitro trials identify a synergistic anti-amyloid B combination for Alzheimer's Disease, Cell Reports 2017, 21:2304-2312.

Hojo et al., Development of high-throughput screening system for osteogenic drugs using a cell-based sensor, Biochemical and Biophysical Research Communiatins 376(2):375-379, 2008.

Hayes et al., Strategies to generate induced pluripotentstem cells, Methods in Molecular Biology 1029: 77-92. doi: 10.1007/978-1-62703-478-4_6 (Year: 2013).

Shafa et al., Human-Induced Pluripotent Stem Cells Manufactured Using a Current Good Manufacturing Practice-Compliant Process Differentiate Into Clinically Relevant Cells From Three Germ Layers, Frontiers in Medicine 5: 69. doi: 10.3389/fmed.

ISR and WO for PCT/US2021/030128 mailed Aug. 25, 2021, 10 pages.

Essential 8 medium C037161 Essential8System Brochure (thermofisher.com), downloaded on Aug. 24, 22, pp. 1-2.

Ionescu et al., Compartmental microfluidic system for studying muscle-neuron communication and neuromuscular junction maintenance, 2016 European Journal.

DMEM F-12 Formulation, pp. 1-5, 2022.

Mehta et al., The actions of retinoids on cellular growth correlate with their actions on gap junctional communication, JCB 108, 1053-1065, 1989.

Munera et al., Differentiation of Human Pluripotent Stem Cells into Colonic Organoids via Transient Activation of BMP Signaling, Cell Stem Cell, 21, 51-64, 2017.

Kim, et al. [3-Cell regeneration through the transdifferentiation of pancreatic cells: Pancreatic progenitor cells in the pancreas, Journal of Diabetes Investigation 7(3): 286-296. doi: 10.1111/jdi .12475. (Year: 2016)IDS.

Clayton, et al., Generating induced pluripotent stem cell derived endothelial cells and induced endothelial cells for cardiovascular disease modelling and therapeutic angiogenesis, International Journal of Cardiology 197: 116-122. doi: 10.1016/j.ijcard.2015.06.038. (Year: 2015).

International Search Report and Written Opinion of PCT Application No. PCT/US2017/013250, Dated Mar. 31, 2017, 12 Pages.

International Search Report and Written Opinion of PCT Application No. PCT/US2016/057724, Dated Jan. 9, 2017, 17 Pages.

International Search Report and Written Opinion of PCT/US2017/016098, Dated Jun. 22, 2017, 14 Pages.

International Search Report and Written Opinion of PCT/US2017/016079, Dated Jul. 25, 2017, 26 Pages.

International Search Report and Written Opinion of PCT/US2017/049193, Dated Nov. 6, 2017, 9 Pages.

International Search Report and Written Opinion of PCT/US2017/049115, Dated Nov. 28, 2017, 11 Pages.

International Search Report and Written Opinion of PCT/US2018/022511, Dated Jul. 26, 2018, 11 Pages.

International Search Report and Written Opinion of PCT/US2018/033498, Dated Aug. 9, 2018, 9 Pages.

International Search Report and Written Opinion for PCT/US2018/022455 dated Aug. 23, 2018, 13 pages.

International Preliminary Report on Patentability for PCT/US2016/057724 dated Apr. 24, 2018, 15 pages.

International Preliminary Report on Patentability for PCT/US2017/013250 dated Jul. 17, 2018, 7 pages.

International Preliminary Report on Patentability for PCT/US2017/016098 dated Aug. 7, 2018, 10 pages.

International Preliminary Report on Patentability for PCT/US2017/016079 dated Aug. 7, 2018, 21 pages.

International Preliminary Report on Patentability for PCT/US2018/022511, dated Sep. 17, 2019, 8 pages.

International Preliminary Report on Patentability for PCT/US2018/022455 dated Aug. 23, 2018, 9 pages.

International Preliminary Report on Patentability for PCT/US2018/033498 dated Nov. 19, 2019, 8 pages.

International Preliminary Report on Patentability for PCT/US2017/049193 dated Mar. 5, 2019, 8 pages.

International Preliminary Report on Patentability for PCT/US2017/049115 dated Mar. 5, 2019, 8 pages.

International Search Report and Written Opinion of PCT/US2019/023749, Dated Jun. 25, 2019, 12 Pages.

AU 2016341880 Examination Report dated Jan. 15, 2020, 5 pages.

AU 2017214468 Examination Report dated Dec. 10, 2019, 5 pages.

CA 3034614 Examination Report dated Jul. 5, 2019, 5 pages.

EP 16858141.1 Extended Search Report dated Mar. 15, 2019, 10 pages.

EP 17748100.9 European Partial Supplementary Search Report dated Sep. 18, 2019, 15 pages.

EP 17748100.9 European Extended Search Report dated Dec. 20, 2019, 12 pages.

EP 17748084.5 European Extended Search Report dated Sep. 10, 2019.

EP 17847396.3 European Extended Search Report dated, Jan. 28, 2020, 11 pages.

EP17847365.8 European Extended Search Report dated Jan. 21, 2020, 11 pages.

GB1811716.8 Examination Report dated Feb. 12, 2020, 6 pages.

GB 1903007.1 Search Report dated Apr. 1, 2019, 8 pages.

SG 11201803143Y Search Report dated Jul. 15, 2019, 3 pages.

Action Potential, Wikipedia, pp. 1-29 Downloaded on Apr. 28, 2019, https://en.wikipedia.org/wiki/Action_potential.

Adriani et al., Modeling the Blood-Brain Barrier in a 3D Triple Co-Culture Microfluidic System, 37th Annual International Conference of the IEEE Engineering in Medicine and Biology Society, IEEE, pp. 338-341.

Armstrong et al., Human Induced Pluripotent Stem Cell Lines Show Stress Defense Mechanisms and Mitochondrial Regulation Similar to Those of Human Embryonic Stem Cells, 2010, Stem Cells, vol. 28(4), pp. 661-673.

Barrett et al., Reliable Generation of Induced Pluripotent Stem Cells from Human Pymphoblastoid Cell Lines, 2014, Stem Cells Translational Medicine, vol. 3, pp. 1429-1434.

Ben-Zvi et al., Modeling Human Nutrition Using Human Embryonic Stem Cells, Cell, 2015, vol. 161(1), pp. 12-17.

Bhatia et al., Microfluidic Organs-on-Chips, Nature Biotechnology, 2014, vol. 32(8), pp. 760-772.

Booth, Ross Hunter, A Microfluidic in Vitro Model of the Blood-Brain Barrier, Dissertation, 2014, pp. 1-177.

(56) References Cited

OTHER PUBLICATIONS

Boyer et al., More than a Bystander: The Contributions of Intrinsic Skeletal Muscle Defects in Motor Neuron Diseases, 2013, Frontiers in Physiology, vol. 4, Article 356, pp. 1-12.
Brown et al., Recreating Blood-Brain Barrier Physiology and Structure on Chip: A Novel Neurovascular Microfluidic Bioreactor, 2015, Biomicrofluidics, vol. 9(5).
Cashman et al., Induced Pluripotent Stem Cells and Motor Neuron Disease: Toward an Era of Individualized Medicine, J. Neurosci, 2013, vol. 33, pp. 8587-8589.
Chal et al., Differentiation of Pluripotent Stem Cells to Muscle Fiber to Model Duchenne Muscular Dystrophy, 2015, Nature Biotechnology, vol. 33(9), pp. 962-969.
Chen et al., Surface Marker Epithelial Cell Adhesion Molecule and E-Cadherin Facilitate the Identification and Selection of Induced Pluripotent Stem Cells, 2011, Stem Cell Rev., vol. 7(3), pp. 722-735.
Date et al., Mini-Gut Organoids: Reconstruction of the Stem Cell Niche, Annu. Rev. Cell Dev. Biol., 2015, vol. 31, pp. 269-289.
Dhumpa et al., Temporal Gradients in Microfluidic Systems to Probe Cellular Dynamics: A Review, Anal. Chim. Acta, 2012, vol. 743, pp. 9-18.
Dimos et al., Induced Pluripotent Stem Cells Generated from Patients with ALS can be Differentiated into Motor Nuerons, Science, 2008, vol. 321, pp. 1218-1221.
Douville et al., Fabrication of Two-Layered Channel System with Embedded Electrodes to Measure Resistance Across Epithelial and Endothelial Barriers, 2010, Analytical Chemistry, vol. 82(6), pp. 2505-2511.
Ebert et al., EZ Spheres: A Stable and Expandable Culture System for the Generation of Pre-rosette Multipotent Stem Cells from Human ESCs and iPSCs., 2013, Stem Cell Research, vol. 10(3), pp. 417-427.
Esch et al., Organs-on-Chips at the Frontiers of Drig Discovery, Nature Reviews, 2015, vol. 14(4), pp. 248-269.
Evans et al., The Development of a Method for the Preparation of Rat Intestinal Epithelial Cell Primary Cultures, 1992, Journal of Cell Science, vol. 101, pp. 219-231.
Gao et al., Regulation of Cell Migration and Osteogenic Differentiation in Mesenchymal Stem Cells under Extremely Low Fluidic Shear Stress, Biomicrofluidics, 2014, vol. 8(5), Article No. 052008.
Gel, Wikipedia, pp. 1-29 Downloaded on Sep. 14, 2018, https://en.wikipedia.org/wiki/Gel.
Gracz et al., CD24 and CD44 Mark Human Intestinal Epithelial Cell Populations with Characteristics of Active and Facultative Stem Cells, 2013, Stem Cells, vol. 31(9), pp. 2024-2030.
Gross et al., Applications of Microfluidics for Neuronal Studies, 2007, Journal of the Neurological Sciences, vol. 252, pp. 135-143.
Hu et al. Neural differentiation of human induced pluripotent stem cells follows developmental principles but with variable potency, PNAS, 2010, vol. 107(9), pp. 4335-4340.
Hu et al., Derivation, Expansion and Motor Neuron Differentiation of Human-Induced Pluripotent Stem Cells with Non-Integrating Episomal Vectors and a Defined Xenogeneic-Free Culture System, Mol Neurobiol, 2016, vol. 53, pp. 1589-1600.
Hughes et al., Matrigel: A Complex Protein Mixture Required for Optimal Growth of Cell Culture, 2010, Proteomics, vol. 10, pp. 1886-1890.
Huh et al., From 3D Cell Culture to Organs-on-Chips, Trends in Cell Biology, 2011, vol. 21(2), pp. 745-754.
Huh et al., Microfabrication of Human Organs-on-Chips, Nature Protocols, 2013, vol. 8(11), pp. 2135-2157.
Hynds et al., Concise Review: The Relevance of Human Stem Cell-Derived Organoid Models for Epithelial Transitional Medicine, Stem Cells, 2013, vol. 1 31, pp. 417-422.
Jang et al., JAK-STAT Pathway and Myogenic Differentiation, JAKSTAT, 2013, vol. 2(2), pp. e23282-1 to e-23282-6.
Joo-Eun, L., Patient-Specific Induced Pluripotent Stem Cell Models of Variant Angina Derived from Peripheral Blood, The Department of Biomedical Sciences Seoul National University College of Medicine, Jul. 2017, pp. 1-75.
Kilic et al., Brain-on-a-Chip Model Enables Analysis of Human Neuronal Differentiation and Chemotaxis, 2016, Lab on a Chip, vol. 16(21), pp. 4152-4162.
Kim et al., Human Gut-on-a-Chip Inhabited by a Microbial Flora that Experiences Intestinal Peristalsis-Like Motions and Flow, Lab on a Chip, 2012, vol. 12(12). pp. 2165.
Kim et al., Gut-on-a-Chip Microenvironmental Induces Human Intestinal Cells to Undergo Villus Differentiation, Integrative Biology, 2013, vol. 5(9), p. 1130-1140.
Kim et al., Contributions of Microbiome and Mechanical Deformation to Intestinal Bacterial Overgrowth and Inflammation in a Human Gut-on-a-Chip, PNAS, 2015, vol. 113(1), pp. E7-E15.
Kirkby et al., A Role for Correlated Spontaneous Activity in the Assembly of Neural Circuits, 2013, Neuron, vol. 80(5), 27 Pages.
Lenner, J., Fat Cells More Easily Programmed into iPS Cells, 2009, pp. 1-2.
Lin et al., Neural Stem Cell Differentiation in a Cell-Collagen-Bioreactor Culture System, 2004, Developmental Brain Research, vol. 153, pp. 163-173.
Lippmann, et al., Human Blood-Brain Barrier Endothelial Cells Derived from Pluripotent Stem Cells, 2012, Nature Biotechnology, vol. 30(8), pp. 783-791.
Lippmann et al., A Retinoic Acid-Enhanced, Multicellular Human Blood-Brain Barrier Model Derived from Stem Cell Sources, Scientific Reports, vol. 4(1), 2014, pp. 1-10.
Lippmann et al., Chemically Defined Differentiation of Human Pluripotent Stem Cells to Hindbrain and Spinal Cord Neural Stem Cells with Defined Regional Identifies, 2015, Protocol Exchange.
Martin et al., Laparoscopic Colorectal Resection in the Obese Patient, 2011, Clinics in Colon and Rectal Surgery, vol. 24(4), pp. 263-273.
Massumi et al., Efficient Programming of Human Eye Conjunctiva-Derived Induced Pluripotent Stem (ECiPS) Cells into Definitive Endoderm-Like Cells, Experimental Cell Research, 2014, vol. 322, pp. 51-61.
Medical Dictionary—Myotube, Downloaded on Jul. 8, 2018, https://medical-dictionary.thefreedictionary.com/myotube, p. 1.
Murphy et al., Scaffolds for 3D in vitro Culture of Neural Lineage Cells, Acta Biomaterialia, 2017, vol. 54, pp. 1-20.
Nicoleau et al., Embryonic Stem Cells Neural Differentiation Qualifies the Role of Wnt/[beta]-Catenin Signals in Human Telecephalic Specification and Regionalization: Human ESC Telencephalic Differentiation, Stem Cells, 2013, vol. 31(9), pp. 1763-1774.
Niego et al., Improved Method for the Preparation of a Human Cell-based, Contact Model of the Blood-Brain Barrier, 2013, J. Vis. Exp., vol. 81(e50934), pp. 1-9.
Nostro et al., Efficient Generation of NKX6-1+ Pancreatic Progenitors from Multiple Human Pluripotent Stem Cell Lines, Stem Cell Reports, 2015 4(4), pp. 591-604.
Ochetta et al., High-Throughput Microfluidic Platform for 3D Cultures of Mesenchymal Stem Cells, Towards Engineering Developmental Processes, Scientific Reports, 2015, vol. 5, Article No. 10288, pp. 1-12.
Okita et al., A More Efficient Method to Generate Integration-Free Human iPS Cells, 2011, Nature Methods, vol. 8(5), pp. 409-412.
Ong et al., A Gel-Free 3D Microfluidic Cell Culture System, Biomaterials, 2008, vol. 29, pp. 3237-3244.
Park et al., Chip-Based Comparison of the Osteogenesis of Human Bone Marrow and Adipose Tissue-Derived Mesenchymal Stem Cells under Mechanical Stimulation, PLOS One, 2012, vol. 7(9), pp. 1-12.
Polini et al., Organs-on-a-Chip: A New Tool for Drug Discovery, Expert Opinion on Drug Discovery, 2014, vol. 9(4), pp. 335-352.
Prabhakarpandian et al., SyM-BBB: A Microfluidic Blood Brain Barrier Model, Lab on a Chip, 2013, vol. 13(6), p. 1093.
Qian et al., A Simple and Efficient System for Regulating Gene Expression in Human Pluripotent Stem Cells and Derivatives, Stem Cells, 2014, vol. 32(5), pp. 1230-1238.

(56) References Cited

OTHER PUBLICATIONS

Rajesh et al., Human Lymphoblastoid B-Cell Lines Reprogrammed to EBV-Free Induced Pluripotent Stem Cells, 2011, Blood, vol. 118(7), pp. 1797-1800.
Rhee et al., Patterned Cell Culture Inside Microfluidic Devices, Lab Chip, 2005, vol. 5(1), pp. 102-107.
Roberts et al., Expression of the Thyroid Hormone Transports Monocarboxylate Transporter-8 (SLC16A2) and Organic Ion Transporter-14 (SLCO1C1) at the Blood-Brain Barrier, Endocrinol, 2008, vol. 149(12), pp. 6251-6261.
Rosenberg et al., Calcium Signaling in Neuronal Development, 2011, Cold Spring Harb Perspect Biol., vol. 3(a004259), 13 Pages.
Sareen et al., Human Neural Progenitor Cells Generated from Induced Pluripotent Stem Cells can Survive, Migrate, and Integrate in the Rodent Spinal Cord, Journal of Comparative Neurology, 2014, vol. 522(12), pp. 2707-2728.
Sareen et al., Targeting RNA foci in iPSC-Derived Motor Neurons from ALS Patients with C90RF72 Repeat Expansion, 2013, Science Translational Medicine, vol. 5(208), 208ra149, 26 Pages.
Shimojo et al., Rapid, Efficient and Simple Motor Neuron Differentiation from Human Pluripotent Stem Cells, Molecular Brain, 2015, vol. 8(1), pp. 1-15.
Shimuzu et al., Microfluidic Devices for Construction of Contractile Skeletal Muscle Microtissues, J. Biosci. Bioeng., 2015, vol. 119, pp. 212-216.
Soria-Valles et al., NF-KB Activation Impairs Somatic Cell Reprogramming in Ageing, 2015, Nat. Cell Biol., vol. 17(8), pp. 1004-1013.
Stepniewski et al., Induced Pluripotent Stem Cells as a Model for Diabetes Investigation, Scientific Reports, 2015, 5:8597, 14 pages.
Telias et al., Electrical Maturation of Neurons Derived from Human Embryonic Stem Cells, F1000 Research, 2014, vol. 3(196), p. 1-12.
Tenstad et al., Extensive Adipogenic and Osteogenic Differentiation of Patterned Human Mesenchymal Stem Cells in a Microfluidic Device, Lab on a Chip, 2010, vol. 10(11), pp. 1401-1409.
Uzel et al., New Microfluidic Chip Replicates Muscle-Nerve Connection, 2016, Science Daily, pp. 1-4.
Vatine et al., Human iPSC-Derived Blood-Brain Barrier Chips Enable Disease Modeling and Personalized Medicine Applications, Cell Stem Cell, 2019, vol. 24(6), pp. 995-1005.
Vatine et al., Human iPSC-Derived Blood-Brain Barrier Chips Enable Disease Modeling and Personalized Medicine Applications, Cell Stem Cell, 2019, vol. 24, Supplemental Figures, p. 1-10.
Wang et al., Androgen Receptor-Mediated Apoptosis in Bovine Testicular Induced Pluripotent Stem Cells in Response to Phthalate Esters, 2013, Cell Death Dis., vol. 4(e907), pp. 1-11.
Wang et al., Modeling the Mitochondrial Cardiomyopathy of Barth Syndrome with Induced Pluripotent Stem Cell and Heart-on-Chip Technologies, Nature Medicine, 2014, vol. 20(6), pp. 616-623.
Watson et al., Modelling the Endothelial Blood-CNS Barriers: A Method for the Production of Robust in Vitro Models of the Rat Blood-Brain Barrier and Blood-Spinal Cord Barrier, 2013, BMC Neuroscience, vol. 14(59), pp. 1-21.
Wehkamp et al., Reduced Paneth Cell [alpha]-Defensins in Ileal Crohn's Disease, PNAS, 2005, vol. 102, pp. 18129-18134.
Workman et al., Enhanced Utilization of Induced Pluripotent Stem Cell-Derived Human Intestinal Organoids Using Microengineered Chips, CMGH Cellular and Molecular Gastroenterology and Hepatology, 2018, vol. 5(4), pp. 669-677.
Yamamoto et al., Fluid Shear Stress Induces Differentiation of Flk-1-positive Embryonic Stem Cells into Vascular Endothelial Cells in vitro., 2004, Am. J. Physiol. Heart Circ. Physiol., vol. 288, pp. 1915-1924.
Zilio et al., Universal Hydrophilic Coating of Thermoplastic Polymers Currently Used in Microfluidics, 2014, Biomed. Microdevices, vol. 16(1), pp. 107-114.
Fridley et al., Hydrodynamic modulation of pluripotent stem cells, Stem cell research & therapy,2012, vol. 45.
Zhang et al., Patient-specific 3D microfluidic tissue model for multiple myeloma, Tissue Engineering Part C: Methods, 2014, pp. 663-670.
Jenke et al., DNA Methylation Analysis in the Intestinal Epithelium—Effect of Cell Separation on Gene Expression an Methylation Profile, PLOS One, 2013, vol. 8(2), pp. 1-8.
Brittan et al., The gastrointestial stem cell, Cell Prolif., 2004, vol. 37, pp. 35-53.
Yamamoto et al., The Stabilization Effect of Mesenchymal Stem Cells on the Formation ofMicrovascular Networks in a Microfluidic Device, Journal of Biomechanical Science and Engineering, 2013, vol. 8(2).
Danmark et al., Development of a novel microfluidic device for long-term in situ monitoring of live cells in 3-dimensional matrices, Biomed Microdevices, 2012, pp. 885-893.
Yu et al., A Microfluidic-Based Multi-Shear Device for Investigating the Effects of Low Fluid-Induced Stresses on Osteoblasts, PLOS One, 2014, vol. 9(2), pp. 1-7.
GB 1903007.1 Search Report dated Jun. 24, 2020, 3 pages.
Extended European Search Report for EP 18802136.4 dated Jan. 22, 2021, 12 pages.
Kuratnik et al., Intestinal organoids at tissue surrogates for toxicological and pharmacological studies, biochemical Pharmacology, Apr. 25, 2013, vol. 85:12, pp. 1721-1726.
Workman et al., Intestine-Chip: A new model to understand the role of the Intestinal Epithelium in IBD by combining Microengineering Technology and IPSC-Derived human intestinal organoids, Gastroenterology, Apr. 1, 2017, vol. 152:5, Abstract only.
Jha et al., Motor Neuron differentiation from Pluripotent Stem Cells and Other Intermediate Proliferative Precursors that can be Discriminated by Lineage Specific Reports, Stem Cell Rev Rep, Aug. 2014, 11:194-204.
Lee et al. Microfluidic 3D bone tissue model for high-throughput evaluation of would healing and infection-preventing biomaterials, Biomaterials 33.4 2012 999-1006.
Amoroso M. W. et al., Accelerated High-Yield Generation of Limb-Innervating Motor Neuronsfrom Human Stem Cells. J Neurosci, Jan. 9, 2013, vol. 33, No. 2, pp. 574-586 pp. 575 and 578, Fig. 1 and 2.
Faravelli I. et al., Motor neuron derivation from human embryonic and induced pluripotent stem cells: Experimental approaches and clinical perspectives. Stem Cell Res Ther, Jul. 14, 2014, vol. 5, No. 4, pp. 87.
Written Opinion 11201901628X dated Mar. 10, 2021, 9 pages.
International Search Report and Written Opinion of PCT/US2019/26178, Dated Jun. 11, 2019, 14 Pages.
Notice of Reasons for Rejection for JP 2018-540028 dated Mar. 1, 2021.
International Search Report and Written Opinion of PCT/US2019/26183, Dated Jun. 12, 2019, 10 Pages.
International Search Report and Written Opinion of PCT/US2019/026195 Jun. 12, 2019, 10 pages.
International Search Report and Written Opinion of PCT/US2019/026193 Jul. 1, 2019, 8 pages.
Kondo, T. et al., Ipsc-based Coound screening and in vitro trials identify a synergistic anti-amyloid b combination for Alzheimer's Disease, Cell Reports, 2017, vol. 21, pp. 2304-2312.
McKinney, C.E. et al., Using induced pluripotent stem cells derived neurons to model brain diseases, Neural Regeneration Research, 2017, 12:7 pp. 1-11.
Li, Y. et al., Protein kinase C controls lysosome biogenesis independently of mTORC1, Nature Cell Biology, 2016, 10:10, pp. 1-26.
Kilpatrick, K. et al., Genetic and chemical activation of TFEB mediates clearance of aggregated a-synuclein, PLoS One, 2015, 10:3, pp. 1-21.
Chou, B.K. et al., Efficient human iPS cell derivation by a non-integrating plasmid from blood cells with unique epigenetic and gene expression signatures, Cell Research, 2011, 21:3, pp. 518-529.
Sundberg, m. et al., Improved cell therapy protocol for Parkinson's Disease based on differentiation efficiency and safety of Hesc-,

(56) References Cited

OTHER PUBLICATIONS

Hipsc and non-human primate Ipsc-derived DA neurons, Stem Cells, 2013, 31:8, pp. 1-25.

* cited by examiner

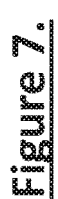
figure 7.
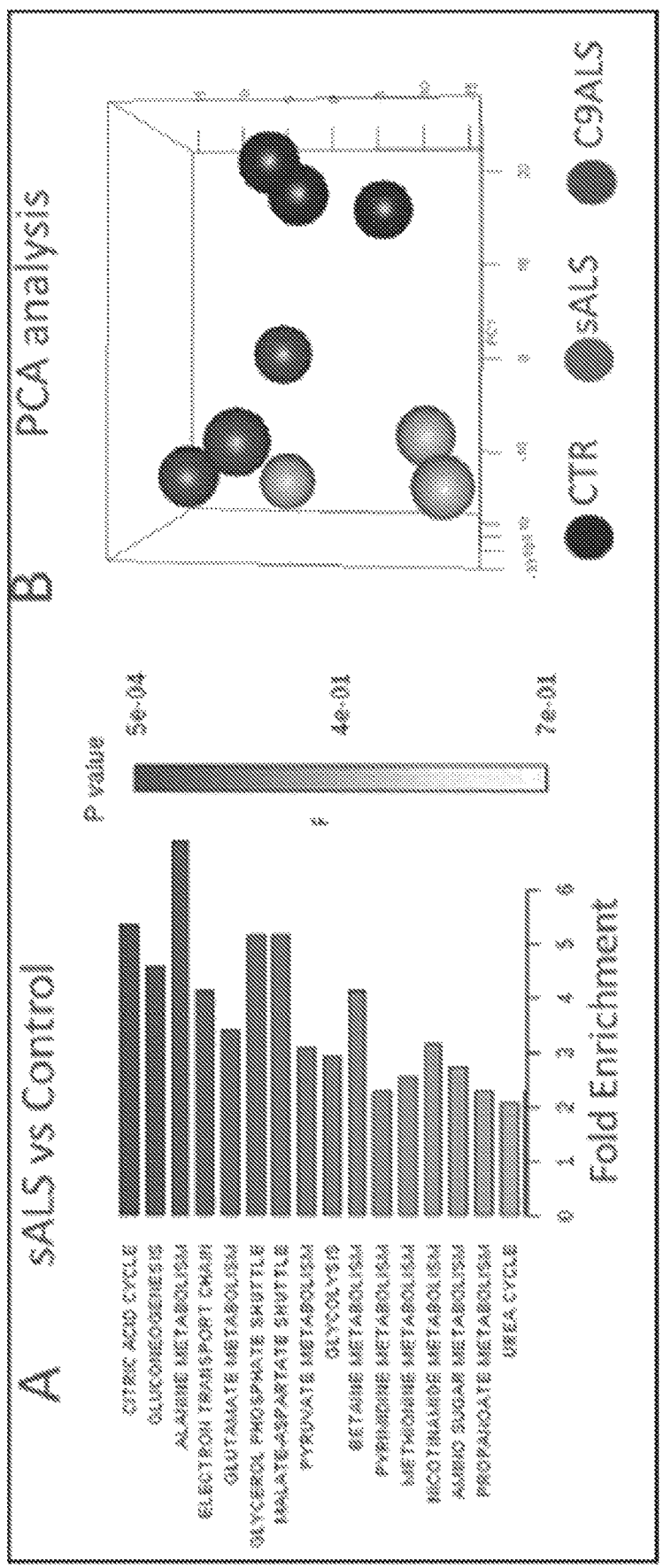

Figure 13.

| Optimum cell combinations | | | | Neurons | Neurons | Neurons Astrocytes | Neurons Microglia Astrocytes |
|---|---|---|---|---|---|---|---|
| Live-Analysis | Post-Analysis | Total | Type | | BMEC | BMEC | BMEC |
| Calcium imaging | Population & Morphology | 20 | PET | Pooled (3) per rep | Pooled (3) per rep | Pooled (3) per rep | Pooled (3) per rep |
| | | | | 5 | 5 | 5 | 5 |
| Metabolomics | Support Cell Characterization | 20 | PET | Pooled (3) per rep | Pooled (3) per rep | Pooled (3) per rep | Pooled (3) per rep |
| | | | | 5 | 5 | 5 | 5 |
| SA1a | (3 Reps) | 120 | PET | Culture time (6) ZOEs: 2 Months | | | |

Figure 14.

| | | spMN | DAN | Assay | |
|---|---|---|---|---|---|
| Live Imaging | Function | Spontaneous Activity | | Ca. Imaging (MEA) | Live Analysis |
| | | Network Activity | | | |
| Effluent | Enzyme | Cell Death | | Lactate Dehydrogenase | |
| | Metabolite | Metabolome | | Mass Spec. | |
| | | Glutamate | Dopamine | | |
| | | Acetylcholine | Tyrosine Hyroxylase | | |
| | | Norepinephrine | | | |
| | | Glutathione | | | |
| High Content Imaging | Population | Nestin, Tuj1, MAP2, GFAP, S100β, CD11β, PU.1, GLUT-1, ZO-1 | | Support Cell Characterization | Post-Analysis |
| | | SMI32/Isl1 | TH/PITX3 | Population & Morphology | |
| | Death | Apoptosis | | Caspase-3 | |
| | | Oxidative Stress | | Mitotracker | |
| | Protein Agg. | Phospho-TDP | α-Synuclein | High Resolution Microscopy | |
| | | RanGAP | ubiquitin | | |
| | | FAS ligand | | | |
| | | SOD1 | | | |
| Omics | | Proteome | | SWATH | |
| | | Transcriptome | | RNASeq | |

Figure 15.

Disease Phenotype Screen

| Live-Analysis | Post-Analysis | Total | Type | spMN | | | | | | | | | DAN | | | |
|---|---|---|---|---|---|---|---|---|---|---|---|---|---|---|---|---|
| | | | | Control (spMNs) | Chips | ALS (spMNs) | Chips | SMA (spMNs) | Chips | Control (DANs) | Chips | Sporadic PD (DANs) | | | | |
| Calcium Activity | Morphology, Protein Aggregation | 20 | PET | SMI32(Ms)/Isl1(Gt) p-TDP43(Rb) | 4 | SMI32(Ms)/Isl1(Gt) p-TDP43(Rb) | 4 | SMI32(Rbs)/Isl1(Gt) p-TDP43(Rb) | 4 | PITX3(Rb)/TH(Sh) α-Syn(Ms) | 4 | PITX3(Rb)/TH(Sh) α-Syn(Ms) | | | | |
| | Apoptosis, Mitochondria | 20 | PET | Mitotracker/Caspase3 | 4 | Mitotracker/Caspase3 | 4 | Mitotracker/Caspase3 | 4 | Mitotracker/Caspase3 | 4 | Mitotracker/Caspase3 | | | | |
| LDH Assay | RNA Seq | 50 | PET | Pooled (3) per rep | 10 | Pooled (3) per rep | 10 | Pooled (3) per rep | 10 | Pooled (3) per rep | 10 | Pooled (3) per rep | | | | |
| Metabolomics | Proteomics | 50 | PET | Pooled (3) per rep | 10 | Pooled (3) per rep | 10 | Pooled (3) per rep | 10 | Pooled (3) per rep | 10 | Pooled (3) per rep | | | | |
| *if available | MEA Activity | 8 | MEA | Assay Week 1, 2, 3, 4 | 1 | Assay Week 1, 2, 3, 4 | 1 | Assay Week 1, 2, 3, 4 | 1 | Assay Week 1, 2, 3, 4 | 1 | Assay Week 1, 2, 3, 4 | | | | |
| SA2a | (20 Lines) | 560 | PET | Culture time (6) ZOEs: 7.78 Months | | | | | | | | | | | | |

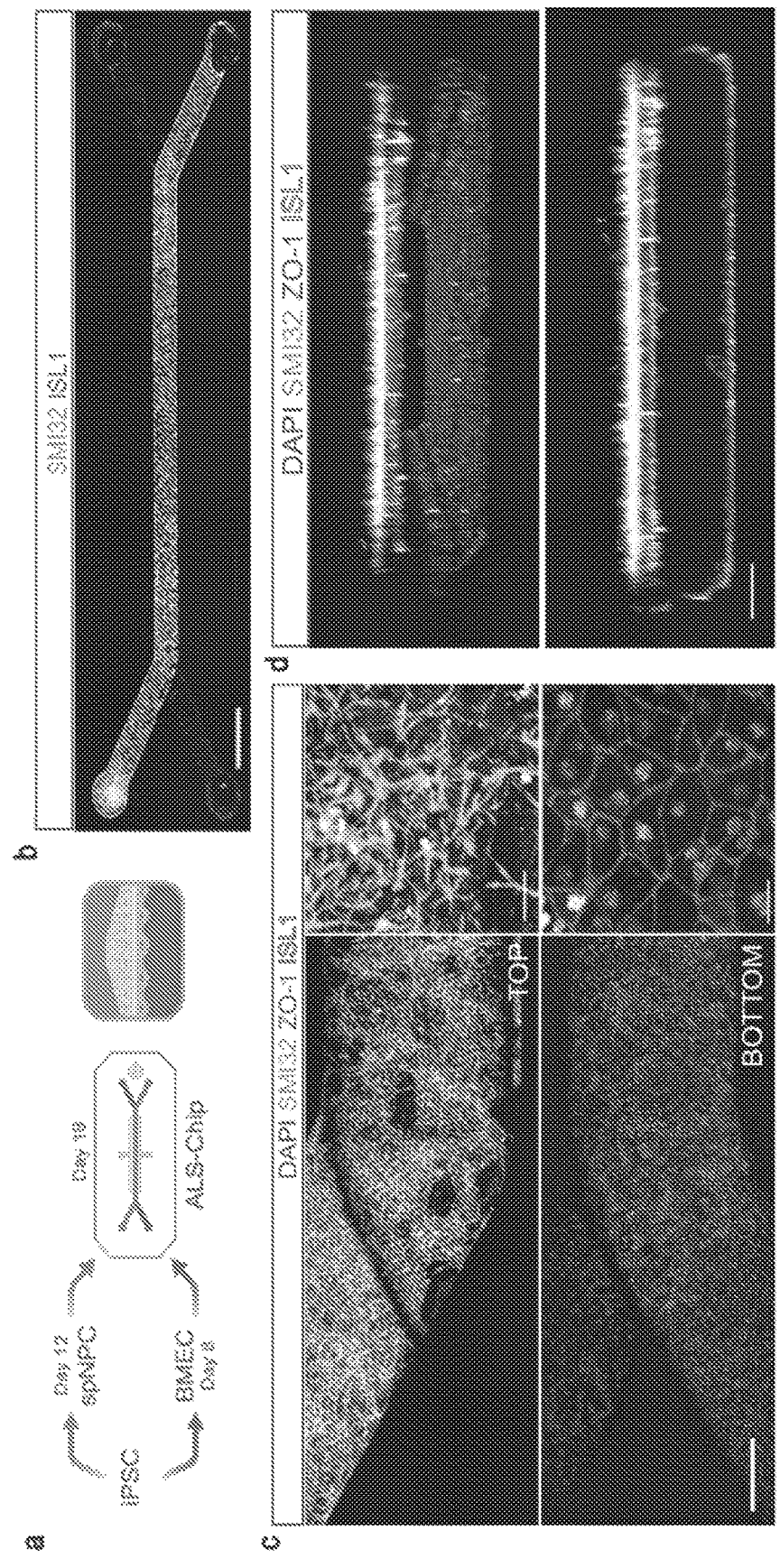
Figure 16. ALS-Chip: Spinal Motor Neurons (spMNs).

PD-Chip: Dopaminergic Neurons (DANs).

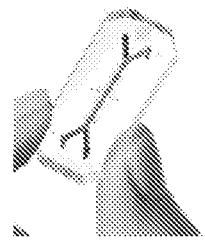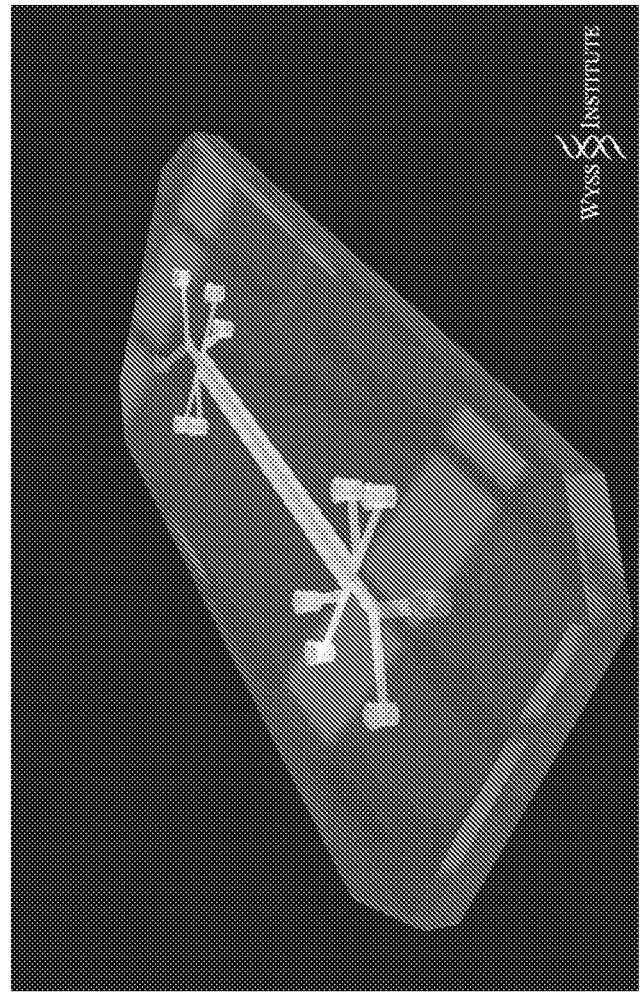
Figure 22.

Figure 23.
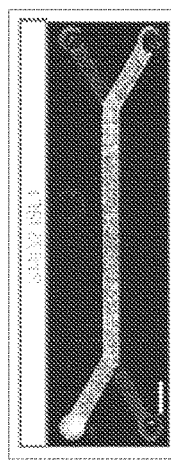
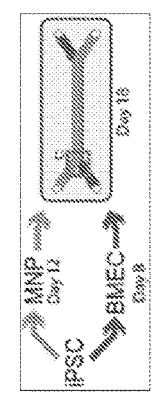
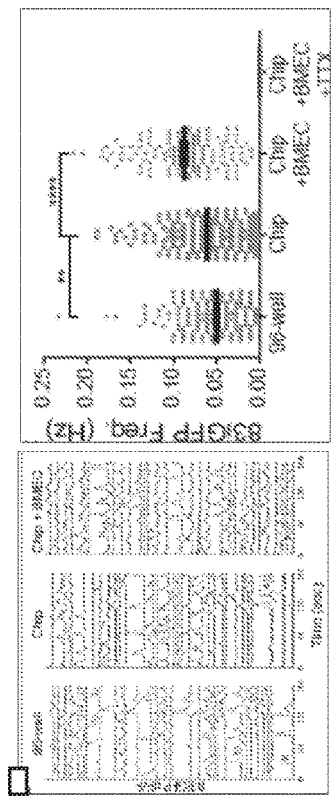
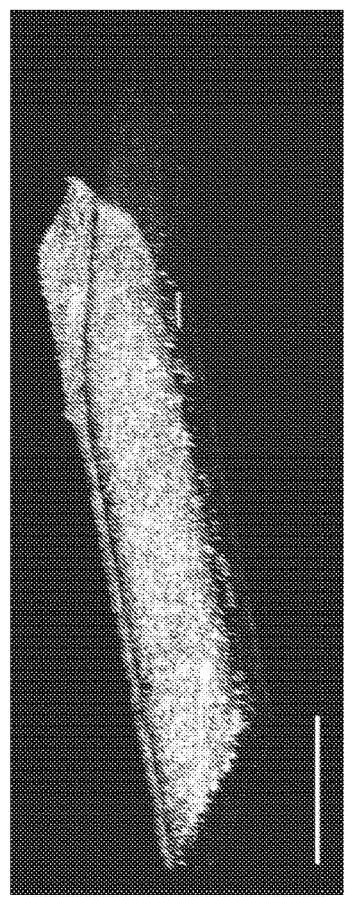
Sances, et. al. *Stem Cell Reports (2018)*

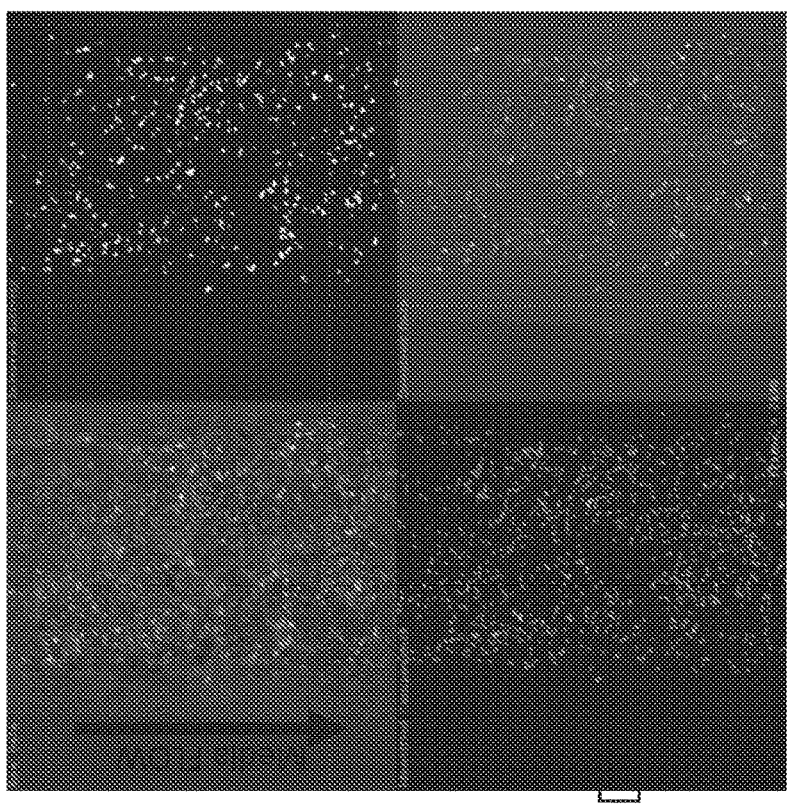
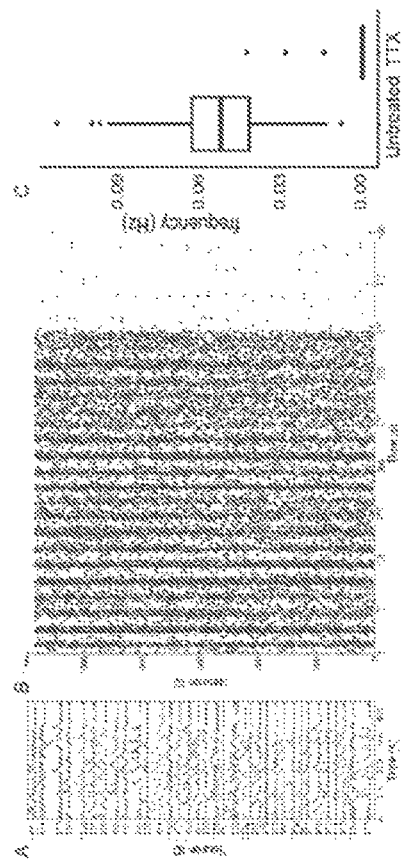
Figure 26.

Figure 27.
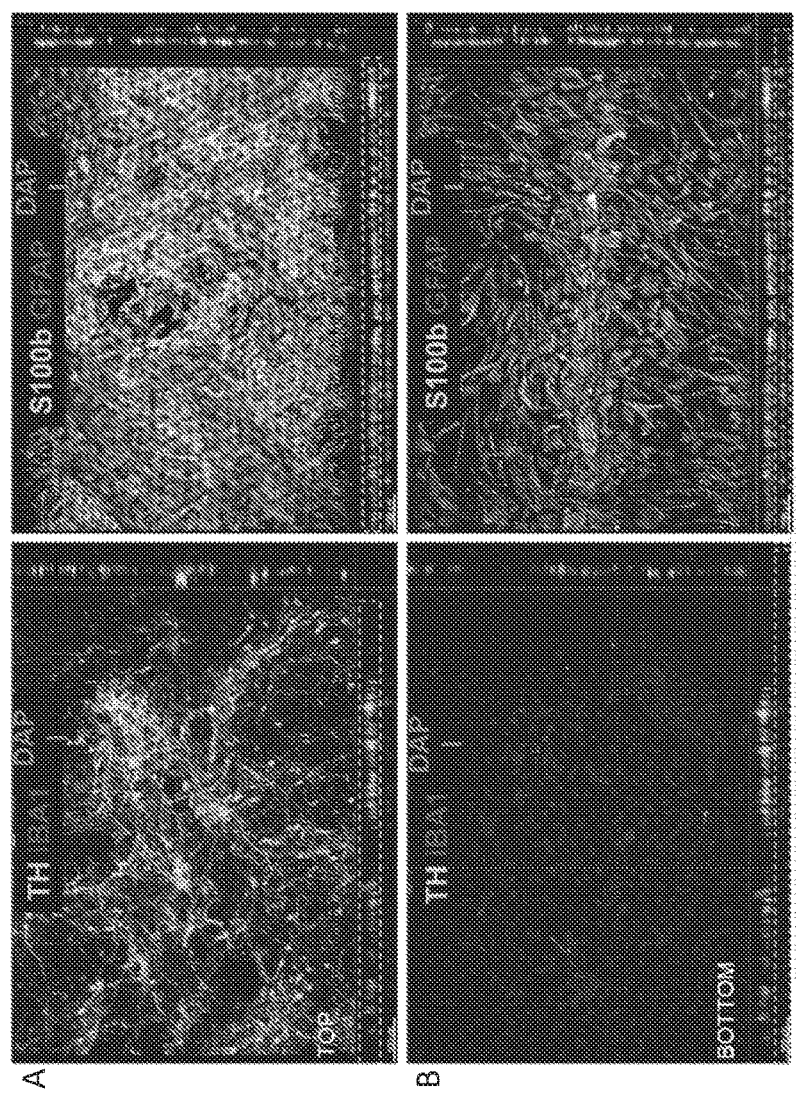
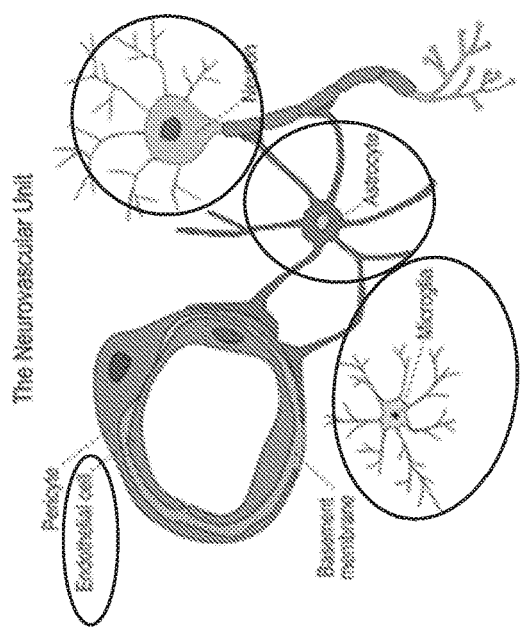

Sporadic ALS and Parkinson's disease modeled in Chips.

Figure 32.

| Milestone | Year | Criteria |
|---|---|---|
| 1) Establish maturation effect of astrocytes and microglia. | 1 | CV <20% survival across 5 chips at 28 days. |
| 2) Establish inter-run stability in one line | 1 | CV <25% across multiple runs at 28 days. |
| 3) Establish inter-line stability in 4 control lines. | 1 | CV <30% across multiple lines at 28 days. |
| 4) Generate 20 PD lines from consortium | 1 | Karyotype and pluritest. |
| 5) Establish disease specific biomarkers for sALS and sPD | 2 | Completion of phenotype panel |
| 6) Confirm biomarker reproducibility across 20 sALS, sPD | 3 | Significant biomarkers must be present in 17 of 20 lines. |
| 7) Complete list of clinically relevant biomarkers | 3 | Literature report completed |
| 8) Screen BBB permeability of novel drug library | 4 | Generation of permeability list. |
| 9) Biomarker reversal screening on novel compounds | 5 | Generation of candidate molecules for clinical trial. |

Figure 33.
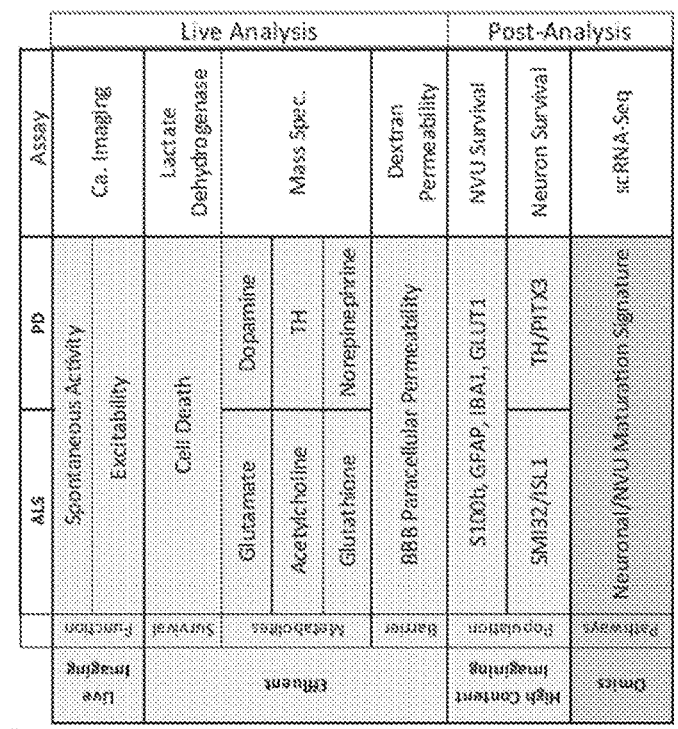
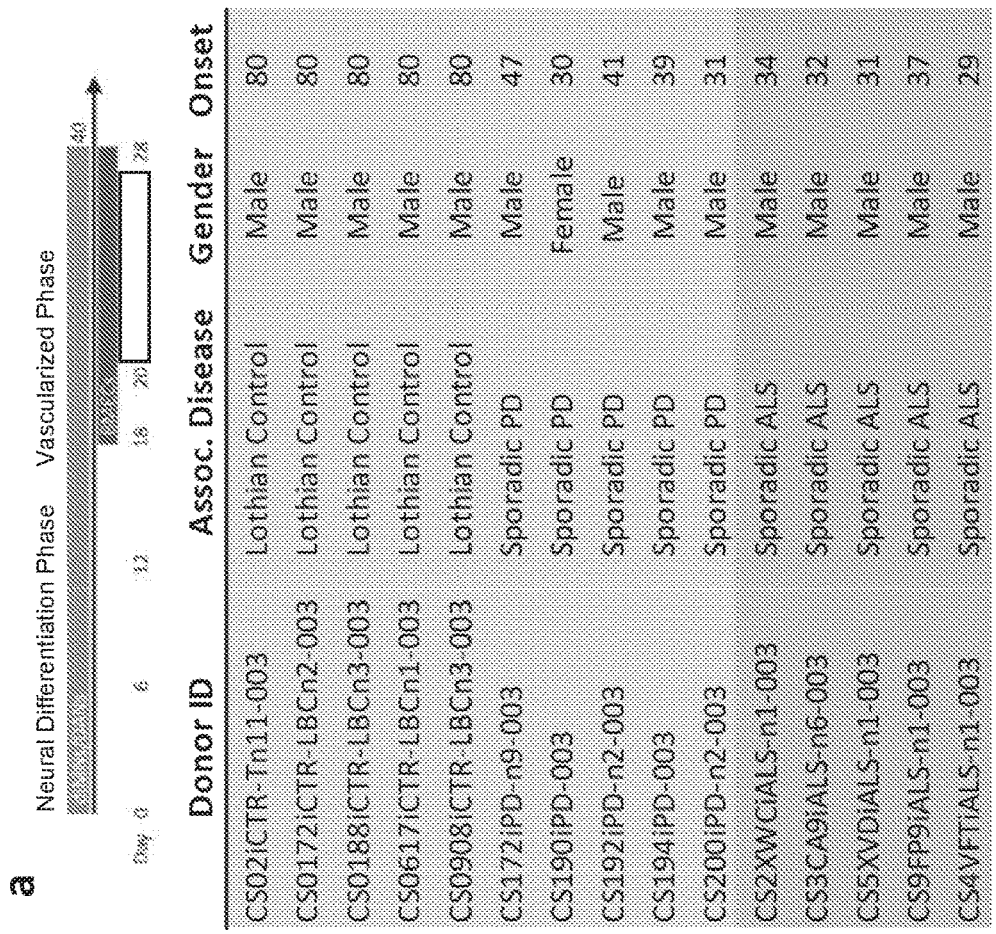

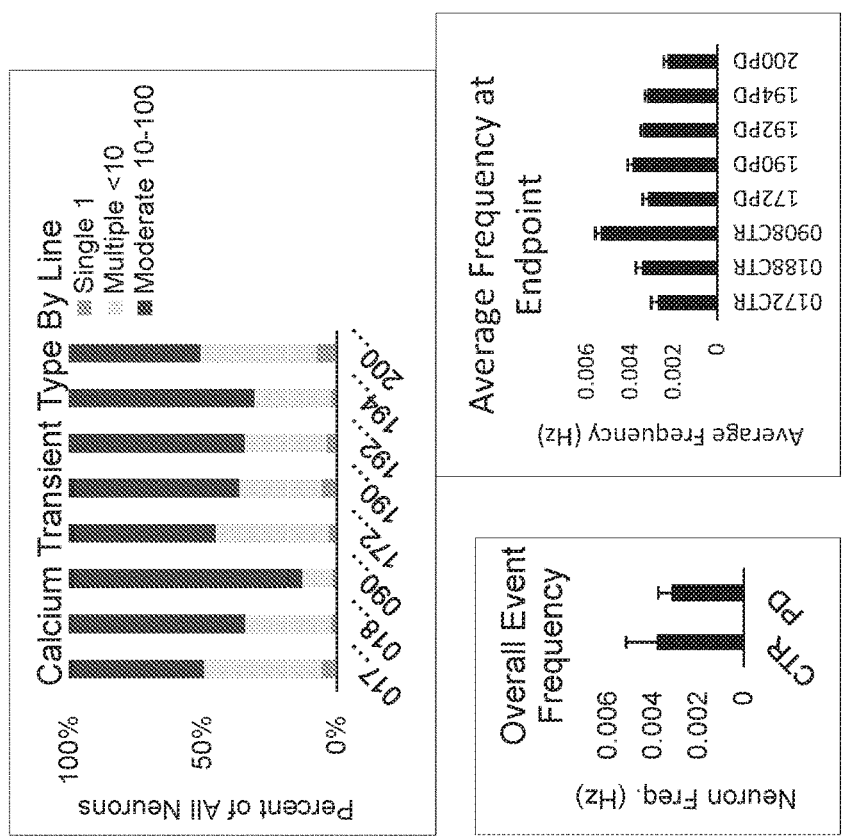
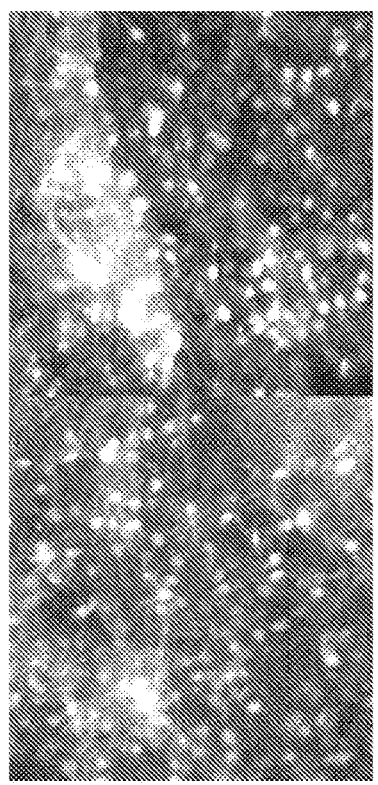
Figure 38.

HUMAN PLURIPOTENT STEM CELL DERIVED NEURODEGENERATIVE DISEASE MODELS ON A MICROFLUIDIC CHIP

CROSS-REFERENCE TO RELATED APPLICATIONS

This application is a National Phase of International Application No. PCT/US2019/026178, filed Apr. 5, 2019, which designated the U.S. and that International Application was published under PCT Article 21 (2) in English, which claims the benefit under 35 U.S.C. § 119 (e) to U.S. provisional patent application No. 62/653,697, filed Apr. 6, 2018, U.S. provisional patent application No. 62/755,282, filed Nov. 2, 2018, and U.S. provisional patent application No. 62/816,785, filed Mar. 11, 2019, the contents of which are incorporated herein by reference in their entirety.

STATEMENT REGARDING FEDERALLY-SPONSORED RESEARCH OR DEVELOPMENT

This invention was made with government support under Grant No. NS105703 awarded by the National Institutes of Health. The government has certain rights in the invention.

FIELD OF THE INVENTION

The present invention relates to the field of culturing cells, and in particular, cells for disease modeling in a fluidic device, including but not limited to a microfluidic device or chip.

BACKGROUND

The physiological, molecular and cellular changes that underlie amyotrophic lateral scleroris (ALS) and Parkinson's disease (PD) are complex. Post-mortem brain tissues clearly have losses in motor and dopamine neurons that underlie the diseases, but the path to neuronal death remains open to speculation—with several existing theories. However, these mutant specific phenotypes have not yet explained adult onset diseases of a sporadic origin, which do not display overt cell death in current culture systems. While genetic forms of ALS and PD are interesting to work on due to specific molecular targets, approximately 90% of ALS and PD cases do not have known genetic mutations and are termed sporadic. There has been relatively little published on sporadic ALS (sALS) or sporadic Parkinson's disease (sPD), with only a few papers using small numbers of patient-derived iPSCs differentiated into motor or dopamine neurons. These studies show some changes in gene expression patterns including mitochondrial function and increased caspase activity or TDP aggregation in a subset of sALS cases. For sporadic PD, some reports show no phenotype while others demonstrate a reduction in DA neuron processes and a cell death phenotype at later time points in vitro. While more challenging than genetic forms of the diseases, the Inventors believe that studies on sALS and sPD have a far greater significance due to the prevalence of sporadic forms and that immediate work is needed to develop these models. In addition, the complex nature of sporadic disease may necessitate a more complete model of neuron physiology to elicit common disease phenotypes that are more indicative of disease pathogenesis at large. The fact that the sporadic lines do not have an overt genetic "smoking gun" does not preclude that complex genetics may contribute to the disease. Thus, there is a great need in the art for models of cellular development and disease pathology that can account for the underlying disease complexity. The confounding issues with sporadic cases can be elegantly examined by using the microphysiological (MPS) models with functionally relevant living human tissues.

Described herein are compositions and methods for microphysiological (MPS) models of disease (MODs), including neurodegenerative diseases such as ALS and Parkinson's Disease. Sporadic ALS and PD cases that have not yet been fully utilized in iPSC models. MPS-based MODs will allow study of electrophysiology and metabalomics as outcome measures. Capitalizing on the MPS ability to flow drugs over the cells and collect information on disease relevant biomarkers in real time, allows for study of these diseases in a manner not otherwise possible.

SUMMARY OF THE INVENTION

As described, iPSC-derived neurons have been extremely successful in modeling early onset neurological diseases, as the Inventors have shown previously for spinal muscular atrophy (SMA). Here, preliminary studies by the inventors show that iPSC-derived motor neurons underwent neurodegeneration in the cell culture dish within 8 weeks of differentiation, mimicking the human pathology in a microphysiological (MPS) model of disease (MOD).

Extending these studies, one can focus on biomarkers based on electrophysiology and metabalomic profiling. Electrophysiological changes specific to genetic forms of ALS have been shown in iPSC models of ALS by us and others. The Inventors predict these will be seen in sporadic models as well. There is less known about PD models, but using MPS MOD one can examine for the first time whether sporadic Parkinson's Disease (sPD) dopaminergic (DANs) have differences in neuronal signaling using calcium imaging. Metabalomic profiling allows the monitoring of up to 300 metabolites in the effluent coming from the chips and is uniquely suited to the MPS. As an example, one can deploy a neurotransmitter screen to monitor neuronal health in the same effluent.

The described MPS MOD disease modeling on a chip allows for study of neurodegenerative disease, including cellular development and disease pathogenesis. As an example, a Parkinson's Disease (PD), PD-Chip is used to model PD in a perfusable system that enables a full array of cellular assays on living human brain tissues. This can be used for diagnostics when compared to PD-chips made from non-diseased patients, and used for research of the mechanisms and therapeutic targets of PD itself. Finally, it can be used for the screening for novel drugs with the added benefit of determining blood brain barrier permeability The PD-Chip is a culture system that utilizes iPSC-derived tissues to create a "brain-on-chip" model that represents specifically the part of the brain that degenerates in Parkinson's disease. In preliminary results, this chip reproduces key PD pathology and includes a novel vascularized compartment. It is used for research for PD biomarkers, patient screening for PD risk assessment, and therapeutic discovery and testing. A panel of biomarkers are generated through analysis of living PD-Chips by neural activity, whole transcriptomic, proteomic, and metabolomic analysis, and functional enzyme tests of media and tissue. By flowing experimental therapeutics through the vasculature channel, key blood brain barrier penetration studies can be performed. In addition, drugs that penetrate can be assessed for efficacy in the human neural cells present in the PD-Chip using the same readouts mentioned for biomarker discovery. While PD models using iPSCs have been attempted, none are from young onset sporadic patients. These chips reproduce PD pathophysiology from sporadic patients. In addition, there are no models that include human vascular component, a critical feature of therapeutic delivery, or incorporate the cast of support cells (e.g., microglia, astrocytes), believed to play roles in disease progression, There are several, additional innovative aspects using the described MPS MOD. The first is the use of a highly scalable MPS, including the culture system to conduct high content biological studies with an entirely human patient specific system. The second is a focus on sporadic ALS and PD cases that have not been fully utilized in iPSC models. The third is the focus on electrophysiology and metabalomics (including neurotransmitter levels) as outcome measures which will capitalize on the MPS ability to flow drugs over the cells or through the blood brain barrier (BBB) and collect information on disease relevant biomarkers in real time biological screens through the cartage system (FIG. 1). The fourth is the combination of an active blood brain barrier with the neural tissue to allow administration of drugs either to the brain side or the blood side, which would simulate the ability of the compound to cross the blood brain barrier. A fifth aspect includes non-PDMS chips (in order to reduce drug absorption) as well as MEA devices built into the chip for real time recording of neural activity.

Described herein is a method of culturing cells, including providing (i) astrocytes, brain microvascular endothelial cells (BMECs), or both (ii) neurons (iii) a microfluidic device including a membrane including a top surface and a bottom surface, seeding the BMECs on the bottom surface to create seeded endothelial cells, or seeding the astrocytes on the top surface to create seeded astrocyte, or seeding the BMECs on the bottom surface to create seeded endothelial cells and seeding the astrocytes on the top surface to create seeded astrocyte, seeding neurons on the top surface to create seeded neurons, culturing the one or more of seeded endothelial cells, seeded astrocytes, and seeded neurons at a flow rate for a period of time. In other embodiments, the method culturing cells, includes providing (i) astrocytes, brain microvascular endothelial cells (BMECs), or both (ii) neurons (iii) microglia (iv) a microfluidic device including a membrane including a top surface and a bottom surface, seeding the BMECs on the bottom surface to create seeded endothelial cells, or seeding the astrocytes on the top surface to create seeded astrocyte, or seeding the BMECs on the bottom surface to create seeded endothelial cells and seeding the astrocytes on the top surface to create seeded astrocyte, seeding neurons on the top surface to create seeded neurons, seeding microglia on the top surface to create seeded microglia, culturing the one or more of seeded endothelial cells, seeded astrocytes, seeded neurons and seeded microglia at a flow rate for a period of time. In other embodiments, astrocytes, brain microvascular endothelial cells, neurons and microglia are each differentiated from stem cells or primary cells. In other embodiments, seeding neurons is one or more days after seeding brain microvascular endothelial cells. In other embodiments, seeding neurons is six days after seeding BMECs. In other embodiments, seeding the BMECs and seeding the astrocytes are done simultaneously. In other embodiments, the seeded endothelial cells exhibit a more mature phenotype after culturing at a flow rate for a period of time compared to the same cells cultured in a static culture. In other embodiments, flow of culture media at a flow rate promotes the formation of tight cell-to-cell junctions among the seeded endothelial cells and brain microvascular endothelial cells. In other embodiments, the method includes detecting the tight cell-to-cell junctions. In other embodiments, tight cell-to-cell junctions are detected by TEER measurements. In other embodiments, measuring neuron or astrocyte activity by at least one of patch clamp measurements, extracellular electrophysiology measurements, imaging using calcium-sensitive dyes or proteins, or imaging using voltage-sensitive dyes or proteins. In other embodiments, tight cell-to-cell junctions are detected by cell permeability assays In other embodiments, the top surface of the membrane includes part of a top microfluidic channel and the bottom surface of the membrane includes part of a bottom microfluidic channel. In other embodiments, the top microfluidic channel and the bottom microfluidic channel each comprise at least one inlet port and at least one outlet port, and the culture media enters the inlet port and exits the outlet port. In other embodiments, the neurons are derived from induced pluripotent stem cells from a human patient diagnosed with a neurodegenerative disease. In other embodiments, the neurodegenerative disease is Amyotrophic lateral sclerosis (ALS), Parkinson's disease (PD), Huntington's disease (HD), or Alzheimer's disease (AD). In other embodiments, the neurons are spinal motor neurons or dopaminergic neurons. In other embodiments, the spinal motor neurons or dopaminergic neurons are cultured under conditions including the flow of culture media at a flow rate for at least three weeks.

Also described herein is a microfluidic device including a co-culture, the co-culture including brain microvascular endothelial cells (BMECs), astrocytes and neurons. In other embodiments, the neurons are spinal motor neurons and dopaminergic neurons. In other embodiments, the co-culture further includes microglia cells. In other embodiments, the microglia are induced pluripotent stem cell (iPSC)-derived microglia. In other embodiments, the neurons are iPSC-derived neurons. In other embodiments, the BMECs are iPSC-derived BMECs. In other embodiments, the astrocytes are iPSC-derived astrocytes. In other embodiments, the BMECs, astrocytes, and neurons are in a microchannel or on a membrane of a microfluidic chip. In other embodiments, the microfluidic chip includes two microchannels separated by a porous membrane having first and second surfaces, wherein the neurons are cultured on the first surface and the brain microvascular endothelial cells are cultured on the second surface. In other embodiments, the brain endothelial cells and the neurons are in contact with flowing culture media.

Described herein is a method, including: contacting a quantity of blood cells with one or more vectors encoding a reprogramming factor, and delivering a quantity of reprogramming factors into the blood cells, culturing the blood cells in a reprogramming media, wherein the quantity of blood cells are obtained from a human subject afflicted with a neurodegenerative disease, and further wherein delivering the reprogramming factors, and culturing in a reprogramming media generates blood cell derived induced pluripotent stem cells (iPSCs). In other embodiments, the neurodegenerative disease is Parkinson's disease (PD). In other embodiments, the neurodegenerative disease is amyotrophiclateral sclerosis (ALS). In other embodiments, the iPSCs are further cultured in fluidic communication with one or more of astrocytes, microglia, and vascular cells. In other embodiments, the one or more vectors are oriP/EBNA1 vectors. In other embodiments, the method includes differentiating the iPSCs into neuron. In other embodiments, the method includes d differentiating the iPSCs into vascular cells. In other embodiments, the method includes differentiating the iPSCs into astrocytes. In other embodiments, the method includes differentiating the iPSCs into microglia.

Described herein is a quantity of neurodegenerative disease derived induced pluripotent stem cells (iPSCs) made by a method including contacting a quantity of blood cells with one or more vectors encoding a reprogramming factor, and delivering a quantity of reprogramming factors into the blood cells, culturing the blood cells in a reprogramming media, wherein the quantity of blood cells are obtained from a human subject afflicted with a neurodegenerative disease, and further wherein delivering the reprogramming factors, and culturing in a reprogramming media generates blood cell derived iPSCs. In other embodiments, the neurodegenerative disease is Parkinson's disease (PD). In other embodiments, the neurodegenerative disease is amyotrophiclateral sclerosis (ALS)

Also described herein is a method of compound screening, including contacting a quantity of cells with one or more test compounds measuring one or more parameters, and selecting one or more test compounds based on the measured one or more parameters, wherein cells are differentiated from neurodegenerative disease derived induced pluripotent stem cells (iPSCs). In other embodiments, the differentiated cells are neurons. In other embodiments, the differentiated cells vascular cells. In other embodiments, the differentiated cells are astrocytes. In other embodiments, the differentiated cells are microglia. In other embodiments, the one or more parameters include permeability of the test compound across a quantity of vascular cells. In other embodiments, the iPSCs are made by a method including contacting a quantity of blood cells with one or more oriP/EBNA1 vectors encoding a reprogramming factor and delivering a quantity of reprogramming factors into the blood cells culturing the blood cells in a reprogramming media, wherein the quantity of blood cells are obtained from a human subject afflicted with a neurodegenerative disease, and further wherein delivering the reprogramming factors, and culturing in a reprogramming media generates blood cell derived iPSCs.

BRIEF DESCRIPTION OF THE FIGURES

FIG. 7. (A) Metabolic Enrichment Analysis shows enriched pathways with corresponding p values and fold enrichment. In sALS vs control, the top five affected pathways are citric acid cycle, gluconeogenesis, alanine metabolism, mitochondrial electron transport chain and glutamate metabolism. This preliminary data shows there are metabolomic differences between sporadic and control and this will be expanded upon using effluent from chip samples. (B) Principal Component Analysis (PCA) of metabolite samples shows a distinct separation between control and disease samples. There is slight separation between C9 and sALS, showing metabolic differences between the two disease states. This preliminary study shows that there are metabolic differences in iPSC derived motor neurons between control and disease. N=1, triplicate.

FIG. 13. Study design showing variable combinations of cells in co-culture.

FIG. 14. Study design showing phenotypic readouts, including electrophysiology, cell survivability, metabolomics, cellular contents, proteome and transcriptome.

FIG. 15. Study design for screening disease phenotypes.

FIG. 22. iPSC-tissues and Organ-Chips: Enhanced modeling through microengineering. Microphysiological Systems (MPS) from Emulate Inc. Microvolume culture could enhances autocrine and paracrine signaling. Multiple compartments allow multiple cell types. Laminar flow of media have unique effects on neuronal culture.

FIG. 23. iPSC-tissues and Organ-Chips: Enhanced modeling through microengineering. Chip and BMECs increase neuronal activity. iPSC-derived neurons in Chip with BMECs had unique gene expression over 96-well.

FIG. 26. DA-Chip: Automated DA neuron activity analysis for live drug efficacy. 1000-2000 neurons per site automatically identified. Chips under continuous perfusion of media. Drugs can be administered to determine efficacy and blood brain barrier permeability.

FIG. 27. Co-culture of iPSC-derived NVU cell types for PD-Chip. Circled cell types were differentiated from same patient separately and co-cultured together on chip. (a) top view (b) bottom view.

FIG. 32. ALS- and PD-Chip development

FIG. 32. Research goals.

FIG. 33. Biomarker discovery trial using SC-Chips with ALS backgrounds. ALS and PD Chips will be validated for stability in stepwise fashion. (a) Table of chosen donor lines for both sporadic ALS and sporadic PD modeling in chips. Lothain controls are clinically assesed, and present with no neurological disease or co-morbidities. (b) Comprehensive array of physiological assays are performed that will also serve as the baseline for future biomarker development studies. Media effluent is assayed for cell death through lactate dehydrogenase assay, and metabolomics through mass spectrometry (Mass Spec.). Neuronal activity is observed through calcium imaging (Ca. Imaging). Cell populations and disease relevant expression will be assessed using advanced imaging techniques. Cells are also analyzed for molecular signatures through transcriptomic analysis. To preserve the unique origin of each cell type, single cell RNA sequencing (scRNA-Seq) is performed and PD-Chip development.

FIG. 38. Calcium imaging shows differential activity in PD-Chips. Calcium imaging acquired in each line at endpoint. Average of 313 neurons per video analyzed. Overall decrease in frequency of firing, highly variant per neuron. Representative still images of live calcium imaging using Fluo-4AM dye. Percent of neurons with calcium transients throughout the 10 minute acquisition binned by extent of activity. Average frequency of all neurons per condition in hertz (Hz).

DETAILED DESCRIPTION

Figure 1:
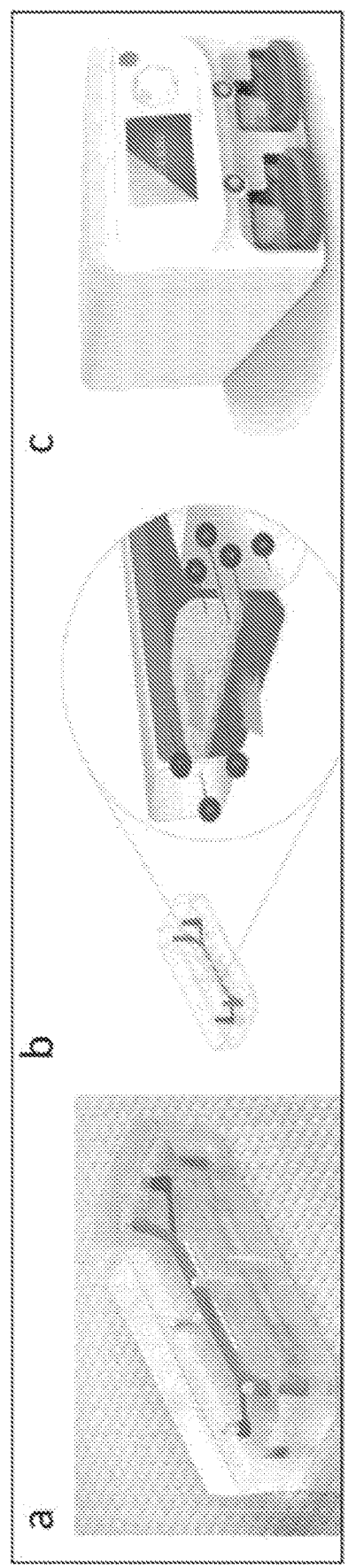
FIG. 1. (a) Organs-chip PDMS microfluidic systems are manufactured at scale. (b) Organ-Chips contain two distinct channels separated by a porous membrane that allow for direct interaction of cell types cultured in microvolume. (c) up to 12 identical chips can be under continuous flow in a microfluidic media delivery system. Each chip is encased in individual cartridges including fluid reservoirs that can be easily sampled for effluent.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., Revised, J. Wiley & Sons (New York, NY 2006); and Sambrook and Russel, *Molecular Cloning. A Laboratory Manual* 4$^{th}$ ed., Cold Spring Harbor Laboratory Press (Cold Spring Harbor, NY 2012), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

Some abbreviations are used herein.

The term "microfluidic" as used herein relates to components where moving fluid is constrained in or directed through one or more channels wherein one or more dimensions are 10 mm or smaller (microscale). Microfluidic channels may be larger than microscale in one or more directions, though the channel(s) may be on the microscale in at least one direction. In some instances the geometry of a microfluidic channel may be configured to control the fluid flow rate through the channel. Microfluidic channels can be formed of various geometries to facilitate a wide range of flow rates through the channels. However, it is important to note that while the present disclosure makes frequent reference to "microfluidic" devices, much of what is taught applies similarly or equally to larger fluidic devices. Larger devices may be especially relevant if the organ-chip is intended for therapeutic application. Examples of applications that may make advantage of larger fluidic devices include the use of the device for the generation of highly differentiated cells (e.g. the device can used to drive cell differentiation and/or maturation, whereupon the cells are extracted for downstream use, which may include implantation, use in an extracorporeal device, or research use), or use of the device for implantation or extracorporeal use, for example, islet on chip, endothelial vascular cell on chip, skeletal muscle chip, or combination of the aforementioned cells (e.g., islet-vascular cells in channels on the chip, islet-muscle cells in channels on the chip). Unlike conventional static cultures, the present invention contemplates microfluidic devices where the cells are exposed to a constant flow of media providing nutrients and removing waste.

As used herein, the phrases "connected to," "coupled to," and "in communication with" refer to any form of interaction between two or more entities, including mechanical, electrical, magnetic, electromagnetic, fluidic, and thermal interaction. For example, in one embodiment, first and second channels in a microfluidic device are in fluidic communication with a fluid reservoir. Two components may be coupled to each other even though they are not in direct contact with each other. For example, two components may be coupled to each other through an intermediate component (e.g. tubing or other conduit).

As described, iPSC-derived neurons have been extremely successful in modeling early onset neurological diseases, as the Inventors have shown previously for spinal muscular atrophy (SMA). Here, preliminary studies by the inventors show that iPSC-derived motor neurons underwent neurodegeneration in the cell culture dish within 8 weeks of differentiation, mimicking the human pathology in a microphysiological (MPS) model of disease (MOD).

Extending these studies, one can focus on biomarkers based on electrophysiology and metabalomic profiling. Electrophysiological changes specific to genetic forms of ALS have been shown in iPSC models of ALS by us and others. The Inventors predict these will be seen in sporadic models as well. There is less known about PD models, but using MPS MOD one can examine for the first time whether sporadic Parkinson's Disease (sPD) DANs have differences in neuronal signaling using calcium imaging. Metabalomic profiling allows the monitoring of up to 300 metabolites in the effluent coming from the chips and is uniquely suited to the MPS. As an example, one can deploy a neurotransmitter screen to monitor neuronal health in the same effluent.

The described MPS MOD disease modeling on a chip allows for study of neurodegenerative disease, including cellular development and disease pathogenesis. As an example, a Parkinson's Disease (PD), PD-Chip is used to model PD in a perfusable system that enables a full array of cellular assays on living human brain tissues. This can be used for diagnostics when compared to PD-chips made from non-diseased patients, and used for research of the mechanisms and therapeutic targets of PD itself. Finally, it can be used for the screening for novel drugs with the added benefit of determining blood brain barrier permeability The PD-Chip is a culture system that utilizes iPSC-derived tissues to create a "brain-on-chip" model that represents specifically the part of the brain that degenerates in Parkinson's disease. In preliminary results, this chip reproduces key PD pathology and includes a novel vascularized compartment. It is used for research for PD biomarkers, patient screening for PD risk assessment, and therapeutic discovery and testing. A panel of biomarkers are generated through analysis of living PD-Chips by neural activity, whole transcriptomic, proteomic, and metabolomic analysis, and functional enzyme tests of media and tissue. By flowing experimental therapeutics through the vasculature channel, key blood brain barrier penetration studies can be performed. In addition, drugs that penetrate can be assessed for efficacy in the human neural cells present in the PD-Chip using the same readouts mentioned for biomarker discovery. While PD models using iPSCs have been attempted, none are from young onset sporadic patients. These chips reproduce PD pathophysiology from sporadic patients. In addition, there are no models that include human vascular component, a critical feature of therapeutic delivery, or incorporate the cast of support cells (e.g., microglia, astrocytes), believed to play roles in disease progression, There are several, additional innovative aspects using the described MPS MOD. The first is the use of a highly scalable MPS, including the culture system to conduct high content biological studies with an entirely human patient specific system. The second is a focus on sporadic ALS and PD cases that have not been fully utilized in iPSC models. The third is the focus on electrophysiology and metabalomics (including neurotransmitter levels) as outcome measures which will capitalize on the MPS ability to flow drugs over the cells or through the blood brain barrier (BBB) and collect information on disease relevant biomarkers in real time biological screens through the cartage system (FIG. 1). The fourth is the combination of an active blood brain barrier with the neural tissue to allow administration of drugs either to the brain side or the blood side, which would simulate the ability of the compound to cross the blood brain barrier. A fifth aspect includes non-PDMS chips (in order to reduce drug absorption) as well as MEA devices built into the chip for real time recording of neural activity. Further information is on organ chip is found in Sances, et al. Human iPSC-derived endothelial cells and microengineered Organ-Chip enhance neuronal development. Stem Cell Reports In press, (2018), which is incorporated by reference herein.

Described herein is a method of culturing cells, including providing (i) astrocytes, brain microvascular endothelial cells (BMECs), or both (ii) neurons (iii) a microfluidic device including a membrane including a top surface and a bottom surface, seeding the BMECs on the bottom surface to create seeded endothelial cells, or seeding the astrocytes on the top surface to create seeded astrocyte, or seeding the BMECs on the bottom surface to create seeded endothelial cells and seeding the astrocytes on the top surface to create seeded astrocyte, seeding neurons on the top surface to create seeded neurons, culturing the one or more of seeded endothelial cells, seeded astrocytes, and seeded neurons at a flow rate for a period of time. In other embodiments, is a method of culturing cells, including providing (i) astrocytes, brain microvascular endothelial cells (BMECs), or both (ii) neurons (iii) microglia (iv) a microfluidic device including a membrane including a top surface and a bottom surface, seeding the BMECs on the bottom surface to create seeded endothelial cells, or seeding the astrocytes on the top surface to create seeded astrocyte, or seeding the BMECs on the bottom surface to create seeded endothelial cells and seeding the astrocytes on the top surface to create seeded astrocyte, seeding neurons on the top surface to create seeded neurons, seeding microglia on the top surface to create seeded microglia, culturing the one or more of seeded endothelial cells, seeded astrocytes, seeded neurons and seeded microglia at a flow rate for a period of time. In other embodiments, astrocytes, BMECs, neurons and microglia are each differentiated from stem cells or are primary cells. In various embodiments, the stem cells are induced pluripotent stem cells (iPSCs). In various embodiments, the iPSCs are from a subject afflicted with a neurodegenerative disease. In various embodiments, one or more of astrocytes, BMECs, neurons and microglia are differentiated from iPSCs. In various embodiments, one or more of astrocytes, BMECs, neurons and microglia are differentiated from iPSCs from a subject afflicted with a neurodegenerative disease. It is to be understood that various combinations of astrocytes, BMECs, neurons and microglia can include cells from both healthy, normal non-disease subjects, and/or subjects afflicted with a neurodegenerative disease. Neurodegenerative diseases include ALS, Parkinson's disease, Alzheimer's disease, Huntington disease, Prion disease, motor neuron diseases (MND), ataxias and palsys such as spinocerebellar ataxia (SCA), spinal muscular atrophy (SMA) and all other neurodegenerative diseases recognized in the art. In various embodiments, the aforementioned diseases include dominant mutant and sporadic forms, for example sporadic ALS, Alzheimer's and Parkinson's. In other embodiments, the neurons, are neurons of the forebrain, midbrain, and/or hindbrain. In other embodiments, the neurons are spinal motor neurons, dopaminergic neurons, or cholinergic neurons.

In other embodiments, seeding neurons is one or more days after seeding BMECs. In other embodiments, seeding neurons is six days after seeding BMECs. In other embodiments, seeding the BMECs and seeding the astrocytes are done simultaneously. In other embodiments, the seeded endothelial cells exhibit a more mature phenotype after culturing at a flow rate for a period of time compared to the same cells cultured in a static culture. In other embodiments, flow of culture media at a flow rate promotes the formation of tight cell-to-cell junctions among the seeded endothelial cells and BMECs. In other embodiments, the method includes detecting the tight cell-to-cell junctions. In other embodiments, tight cell-to-cell junctions are detected by TEER measurements. In other embodiments, measuring neuron or astrocyte activity by at least one of patch clamp measurements, extracellular electrophysiology measurements, imaging using calcium-sensitive dyes or proteins, or imaging using voltage-sensitive dyes or proteins. In other embodiments, tight cell-to-cell junctions are detected by cell permeability assays.

For example, transport and permeability assays can be conducted by perfusion of both, the top and bottom channels with medium at 30 µl/hr. The bottom channel was perfused with neural media or whole human blood treated with sodium citrate and the bottom channel was perfused with neural media. Media/blood collected from both, inputs and effluents from both, top and bottom channels were read by fluorescence, luminescence or MS. Fluorescence (485 nm excitation and 530 nm emission) or luminescence were detected on a plate reader. The values measured were used to calculate $P_{app}$ values as follow:

$$Papp = \frac{\left(\text{Top Output}\left(\frac{\mu g}{ml}\right) - \text{Top Input}\left(\frac{\mu g}{ml}\right)\right)}{\left(\text{Bottom Input}\left(\frac{\mu g}{ml}\right)\right)} * \frac{\left(\text{Flow Rate}\left(\frac{ml}{\sec}\right)\right)}{\text{Membrane area (cm}^2)}$$

In other embodiments, the top surface of the membrane includes part of a top microfluidic channel and the bottom surface of the membrane includes part of a bottom microfluidic channel. In other embodiments, the top microfluidic channel and the bottom microfluidic channel each comprise at least one inlet port and at least one outlet port, and the culture media enters the inlet port and exits the outlet port. In other embodiments, the neurons are derived from induced pluripotent stem cells from a human patient diagnosed with a neurodegenerative disease. In other embodiments, the spinal motor neurons, dopaminergic neurons, or cholinergic neurons are cultured under conditions including the flow of culture media at a flow rate for at least three weeks.

Also described herein is a microfluidic device including a co-culture, the co-culture including brain microvascular endothelial cells (BMECs), astrocytes and neurons. In other embodiments, the neurons are spinal motor neurons and dopaminergic neurons. In other embodiments, the co-culture further includes microglia cells. In other embodiments, astrocytes, brain microvascular endothelial cells, neurons and microglia are each differentiated from stem cells or are primary cells. In various embodiments, the stem cells are induced pluripotent stem cells (iPSCs). In other embodiments, the microglia are induced pluripotent stem cell (iPSC)-derived microglia. In other embodiments, the neurons are iPSC-derived neurons. In other embodiments, the BMECs are iPSC-derived BMECs. In other embodiments, the astrocytes are iPSC-derived astrocytes. In various embodiments, the iPSCs are from a subject afflicted with a neurodegenerative disease. In various embodiments, one or more of astrocytes, BMECs, neurons and microglia are differentiated from iPSCs. In various embodiments, one or more of astrocytes, BMECs, neurons and microglia are differentiated from iPSCs from a subject afflicted with a neurodegenerative disease. It is to be understood that various combinations of astrocytes, BMECs, neurons and microglia can include cells from both healthy, normal non-disease subjects, and/or subjects afflicted with a neurodegenerative disease. Neurodegenerative diseases include ALS, Parkinson's disease, Alzheimer's disease, Huntington disease, Prion disease, motor neuron diseases (MND), ataxias and palsys such as spinocerebellar ataxia (SCA), spinal muscular atrophy (SMA) and all other neurodegenerative diseases recognized in the art. In various embodiments, the aforementioned diseases include dominant mutant and sporadic forms, for example sporadic ALS, Alzheimer's and Parkinson's. In other embodiments, the method includes differentiating the iPSCs into neurons, including neurons of the forebrain, midbrain, and/or hindbrain. In other embodiments, the neurons are spinal motor neurons, dopaminergic neurons, or cholinergic neurons.

In other embodiments, the BMECs, astrocytes, and neurons are in a microchannel or on a membrane of a microfluidic chip. In other embodiments, the microfluidic chip includes two microchannels separated by a porous membrane having first and second surfaces, wherein the neurons are cultured on the first surface and the BMECs are cultured on the second surface. In other embodiments, the cells are in contact with flowing culture media. In various embodiments, the membrane is semi-porous, including 1, 2, 3, 4, 5, 6, 7, 8, 9 10 micro pores. This includes, for example, 3 micron pores.

Described herein is a method, including: contacting a quantity of blood cells with one or more vectors encoding a reprogramming factor, and delivering a quantity of reprogramming factors into the blood cells, culturing the blood cells in a reprogramming media, wherein the quantity of blood cells are obtained from a human subject afflicted with a neurodegenerative disease, and further wherein delivering the reprogramming factors, and culturing in a reprogramming media generates blood cell derived induced pluripotent stem cells (iPSCs). In other embodiments, the neurodegenerative disease is Parkinson's disease (PD). In other embodiments, the neurodegenerative disease is amyotrophiclateral sclerosis (ALS). In other embodiments, the iPSCs are further cultured in fluidic communication with one or more of astrocytes, microglia, and vascular cells. In other embodiments, the one or more vectors are oriP/EBNA1 vectors. In other embodiments, the method includes differentiating the iPSCs into neuron. In other embodiments, the method includes differentiating the iPSCs into vascular cells. In various embodiments, the vascular cells are brain microvascular endothelial cells (BMECs). In other embodiments, the method includes differentiating the iPSCs into astrocytes. In other embodiments, the method includes differentiating the iPSCs into microglia. In other embodiments, the method includes differentiating the iPSCs into neurons, including neurons of the forebrain, midbrain, and/or hindbrain. In various embodiments, the neurons are spinal motor neurons, dopaminergic neurons, or cholinergic neurons. Further information on iPSC reprogramming is found in Barrett, R. et al. Reliable Generation of Induced Pluripotent Stem Cells from Human Lymphoblastoid Cell Lines. Stem Cells Transl Med. 2014 December; 3(12):1429-34, which is fully incorporated by reference herein.

Described herein is a quantity of neurodegenerative disease derived induced pluripotent stem cells (iPSCs) made by a method including contacting a quantity of blood cells with one or more vectors encoding a reprogramming factor, and delivering a quantity of reprogramming factors into the blood cells, culturing the blood cells in a reprogramming media, wherein the quantity of blood cells are obtained from a human subject afflicted with a neurodegenerative disease, and further wherein delivering the reprogramming factors, and culturing in a reprogramming media generates blood cell derived iPSCs. In other embodiments, the neurodegenerative disease is Parkinson's disease (PD). In other embodiments, the neurodegenerative disease is amyotrophiclateral sclerosis (ALS). In various embodiments, the aforementioned diseases include dominant mutant and sporadic forms, for example sporadic ALS and Parkinson's.

Also described herein is a method of compound screening, including contacting a quantity of cells with one or more test compounds measuring one or more parameters, and selecting one or more test compounds based on the measured one or more parameters, wherein cells are differentiated from neurodegenerative disease derived induced pluripotent stem cells (iPSCs). In other embodiments, the differentiated cells are neurons. In other embodiments, the differentiated cells vascular cells. In other embodiments, the differentiated cells are astrocytes. In other embodiments, the differentiated cells are microglia. In other embodiments, the one or more parameters include permeability of the test compound across a quantity of vascular cells, alterations in electrophysiological properties of the cells, alterations in metabolic profile of the cells, including for example, neurotransmitter production and release. In other embodiments, the iPSCs are made by a method including contacting a quantity of blood cells with one or more oriP/EBNA1 vectors encoding a reprogramming factor and delivering a quantity of reprogramming factors into the blood cells culturing the blood cells in a reprogramming media, wherein the quantity of blood cells are obtained from a human subject afflicted with a neurodegenerative disease, and further wherein delivering the reprogramming factors, and culturing in a reprogramming media generates blood cell derived iPSCs.

Further described herein is a biomarker panel for prognosis, diagnosis, or aiding therapeutic selection, including assaying one or more biomarkers in a subject suspected of being afflicted with a neurodegenerative disorder, and prognosing, diagnosing, or selecting a therapeutic regimen based on the assayed one or more biomarkers. In various embodiments, the subjected if suspected of being afflicted with amyotrophic lateral sclerosis (ALS) or Parkinson's disease. In various embodiments, the biomarker is a metabolic enzyme, including neurotransmitters. In various embodiments, biomarkers including nestin, Tuj1, MAP2, GFAP, S100B, CD11B, PU.1, GLUTA-1, ZO-1, SMI31/Isl1, TH/PITX3, Phospho-TDP, FAS ligand, and SOD1, among others. In various embodiments, the biomarkers include opioid receptors. In various embodiments, opioid receptors include Mu 1, Kappa 1, Delta 1, and Opioid Related Nociceptin Receptor 1.

Further information is found in U.S. application Ser. Nos. 15/458,185, 15/352,289, PCT App. No. PCT App. No. PCT/US2017/49115, PCT App. No. PCT/US2017/49193, PCT App. No. PCT/US2017/16079, PCT App. No. PCT/US2017/16098, PCT App. No. PCT/US2017/16079, PCT App. No. PCT/US2017/16098, PCT App. No. PCT/US2017/016098, PCT App. No. PCT/US2017/16079, PCT App. No. PCT/US2018-022511, PCT App. No. PCT/US2016/57724, and PCT App. No. PCT/US2017/49115, and U.S. Prov. App. No. 62/653,697, U.S. Prov. App. No. 62/755,282, U.S. Prov. App. No. 62/816,785, U.S. Prov. App. No. 62/664,888, U.S. Prov. App. No. 62/664,827, U.S. Prov. App. No. 62/816,795, U.S. Prov. App. No. 62/664,942, U.S. Prov. App. No. 62/755,365, each of which is incorporated by reference herein.

EXAMPLES

Below are non-limiting examples.

Example 1

Preliminary Data

Organ-chips allow for MPS models of several organ and tissue systems, including the lung alveolus and small airway, intestine, liver, kidney, and blood-brain barrier and other organs. Organ-chips can be scaled-up while operating in parallel, and can be paired specially developed instruments to eliminate the need for the user to connect and disconnect tubing, reduce fluid dead-volumes to improve sampling, and remove undesired bubbles. These advantages increase experimental throughput, and reducing variability (FIG. 1).

Biological material on organ-chips include induced pluripotent stem cells (iPSCs), iPSC-derived cells and tissue. With a simple blood sample taken in the clinic, one can derive iPSC lines that carry the donor's genetic makeup. The patient's peripheral blood mononuclear cells (PBMCs) are directly reprogrammed, without the need for an expansion step, using non-integrating techniques that allow for transient ectopic expression of reprogramming factors. Over a short period of time, iPSC colonies shed epigenetic marks of their origin tissue and remain a stable source of pluripotent cells carrying the genetic makeup of the donor patient. This method has now been successfully implemented on over 200 PBMC samples from ALS patients, which show less karyotypic abnormalities than other fibroblast-based methods. These iPSCs can be expanded and cryogenically stored for subsequent disease modeling research of various tissue types of interest. The Inventors have developed robust differentiation techniques for the generation of multiple iPSC-derived cell lineages, including brain microvascular endothelial cells (BMECs), astrocytes, microglia, spinal motor neurons (spMNs) and dopaminergic neurons (DANs).

Figure 2:
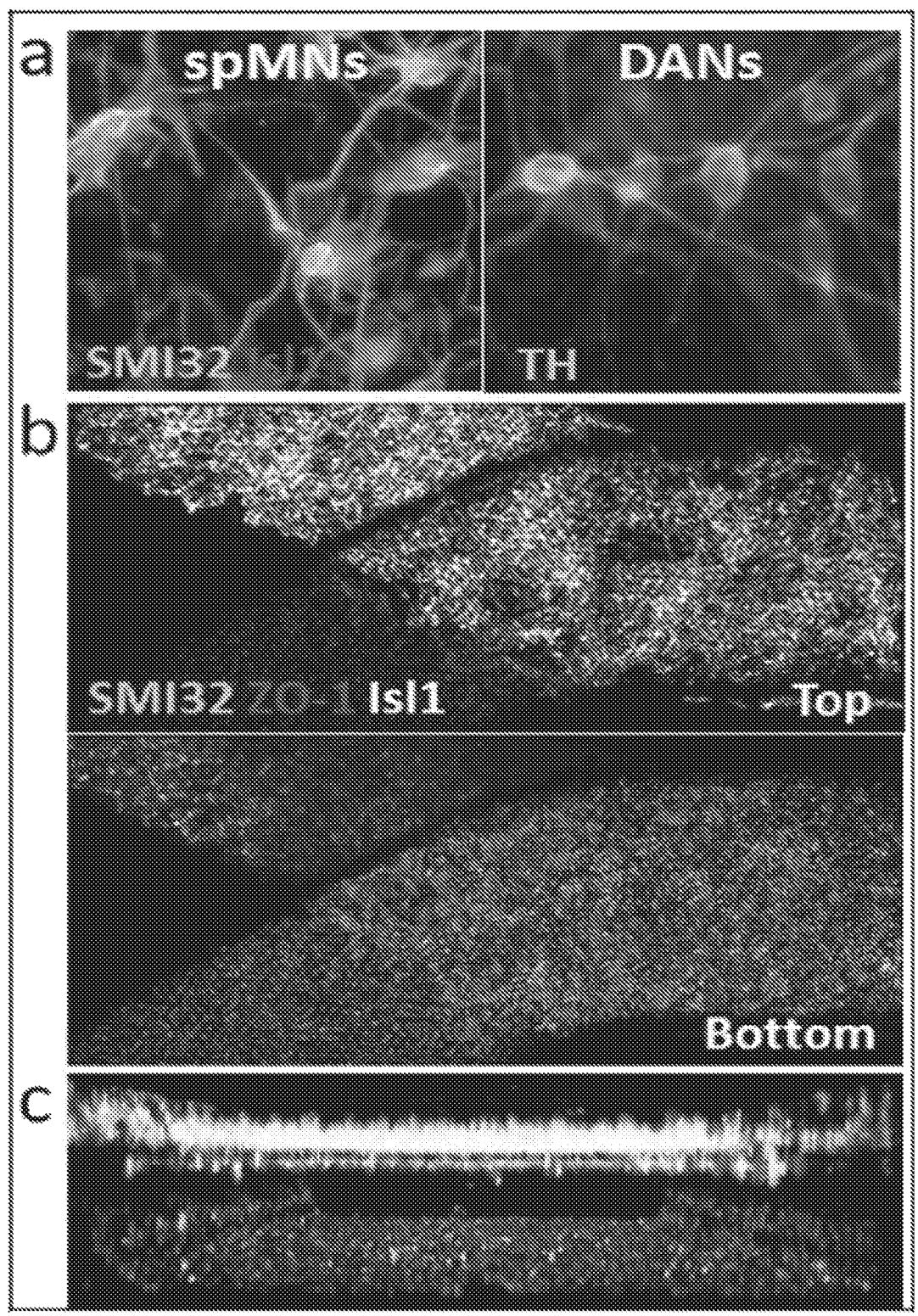
FIG. 2. (A) The Inventors have established robust and highly reproducible methods to direct human iPSCs to spinal motor neurons (spMNs) and dopaminergic neurons (DANs) to study ALS and PD, respectively. spMNs express marker islet 1 (isl1) and DANs express tyrosine hydroxylase (TH). (B) spMNs and DANs (top), mature in the chip with zona-occludens 1 (ZO-1) expressing BMECs (bottom). (C) BMECs coat the entire bottom channel creating a vascular-like lumen that simulate blood brain barrier properties.
Figure 3:
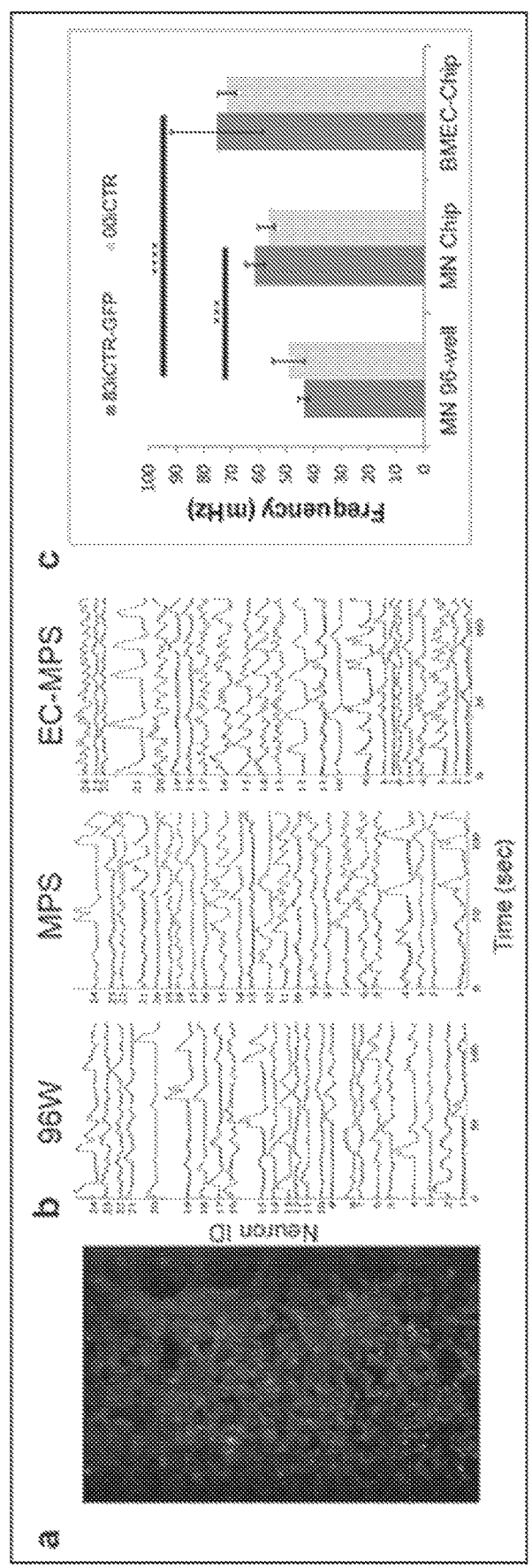
FIG. 3. Neurons are more active in MPS culture. (A) Representative image of spMNs in MPS treated with calcium-activated florescent dye. (B) Transients can be tracked in upwards of 300 neurons in each acquisition simultaneously to determine neural function in the chip. Significant increase in transient activity was observed when spMNs were cultured in MPS, and increased further when BMECs were included into the bottom channel. (C) Two non-diseased iPSC lines were analyzed separately and transient frequency was significantly increased when cultured in the MPS alone (MN chip) and in co-culture with BMECs (BMEC-Chip). Error bars are reported as standard error of the mean, * denotes ANOVA $P \leq 0.001$, ** denotes $P \leq 0.0001$.
Figure 4:
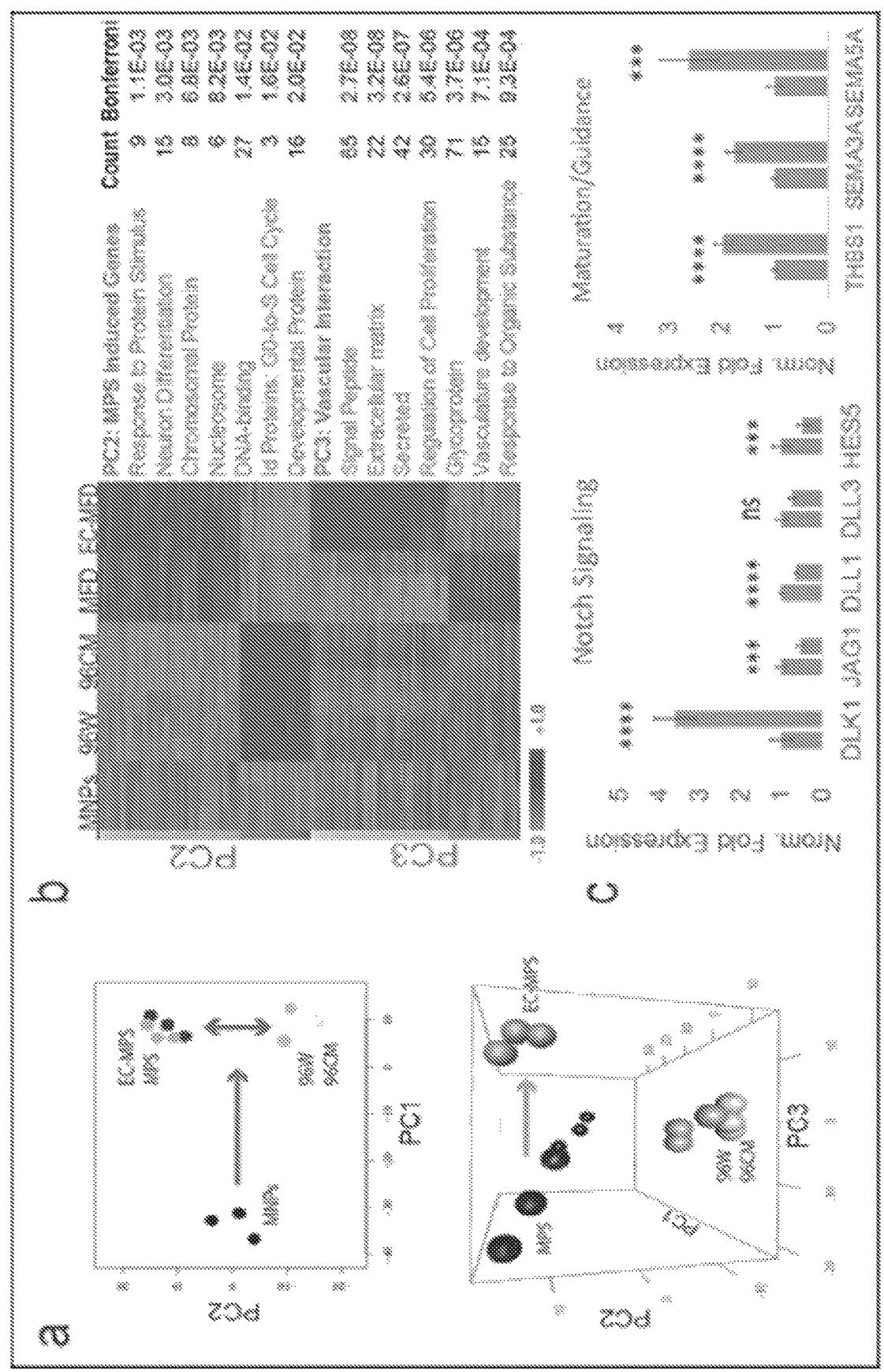
FIG. 4. BMEC co-culture induce specific transcript changes that are related to maturation. Rna-sequencing was conducted on spMNs cultured in the chip (MPS), or in co-culture with BMECs (EC-MPS). Additionally, identical spMNs were cultured in traditional 96 well plates (96W) and in the presence of BMEC conditioned media (96CM). (a) Principle component analysis was conducted on gene transcript reads to determine gene sets associated with the highest variance among all conditions. As spMNs matured away from motor neuron progenitors (MNPs), MPS culture activated a unique set of transcripts (PC2, blue arrow). PC3 genes were expressed specifically in the context of BMEC co-culture (EC-MPS) (b) Top ranking gene sets were sorted into pathways using DAVID. Top ranking PC2 genes enriched for pathways involved in protein stimulation and neural differentiation. PC3 gene pathways contained genes known to control vascular interaction, unique extracellular matrix interaction, and increased secreted protein expression. (c) Known signaling pathways involved in neural maturation were also reproduced in the EC-MPS condition. Notch inhibition is known to promote motor neuron maturation. Secretion of thrombospondin-1 (THBS1) by astrocytes has been previously shown to increase neural maturation in vitro. EC-MPS spMNs upregulated THBS1 as well as semaphorins 3A and 5A.
Figure 8:
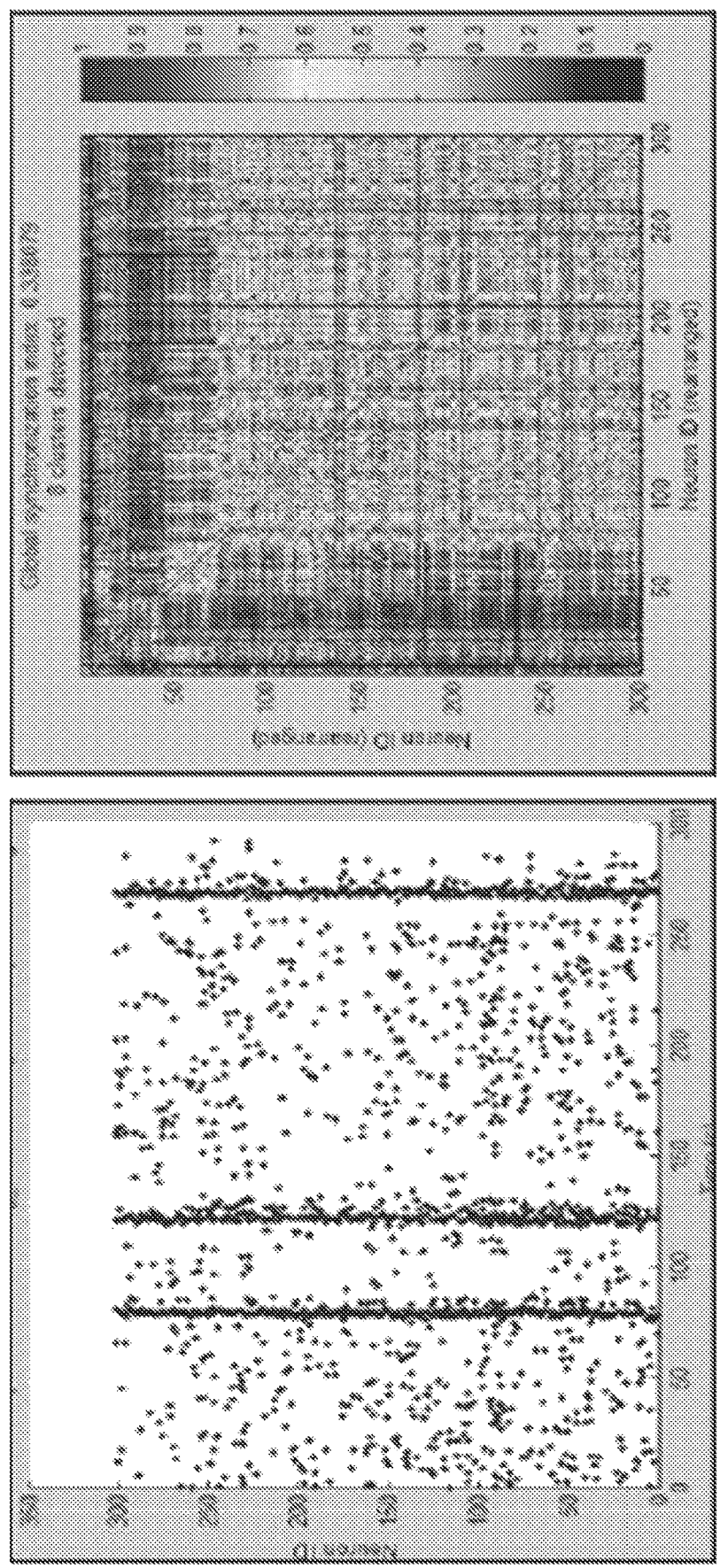
FIG. 8. spMNs matured for more than two weeks in the chips exhibit coordinated bursts of activity indicating neural network formation. This can be quantified at the population level and converted into raster plots (left) showing total neuronal activity from 300 assayed neurons on chip. Individual neurons (y-axis) are recorded over time in seconds (x-axis) and fire simultaneously (lines). The connectivity of these bursts can be quantified by similarity of bursts and displayed by Pierson correlation (right). More network bursting is indicative of healthy developing human neural tissue.

The Inventors have successfully deployed iPSCs, iPSC-derived cells and tissue into MPS systems to better model neurodegenerative disease. The Inventors' preliminary studies have shown that spMNs and DANs can survive in co-culture with BMECs (and with astrocytes) in the MPS for over 3 weeks and produce appropriate neuronal phenotypes (FIG. 2). In addition, the Inventors can detect activation of neurons using calcium imaging that is enhanced by the chip environment and the presence of BMECs (FIGS. 3 & 8). Finally, the Inventors observe that the combined chip and endothelial interaction leads to specific changes in RNA-seq profiles, suggesting that the interacting cell types stimulate known vascular interaction pathways and are beginning to mature towards a more functional condition (FIG. 4).

Figure 12:
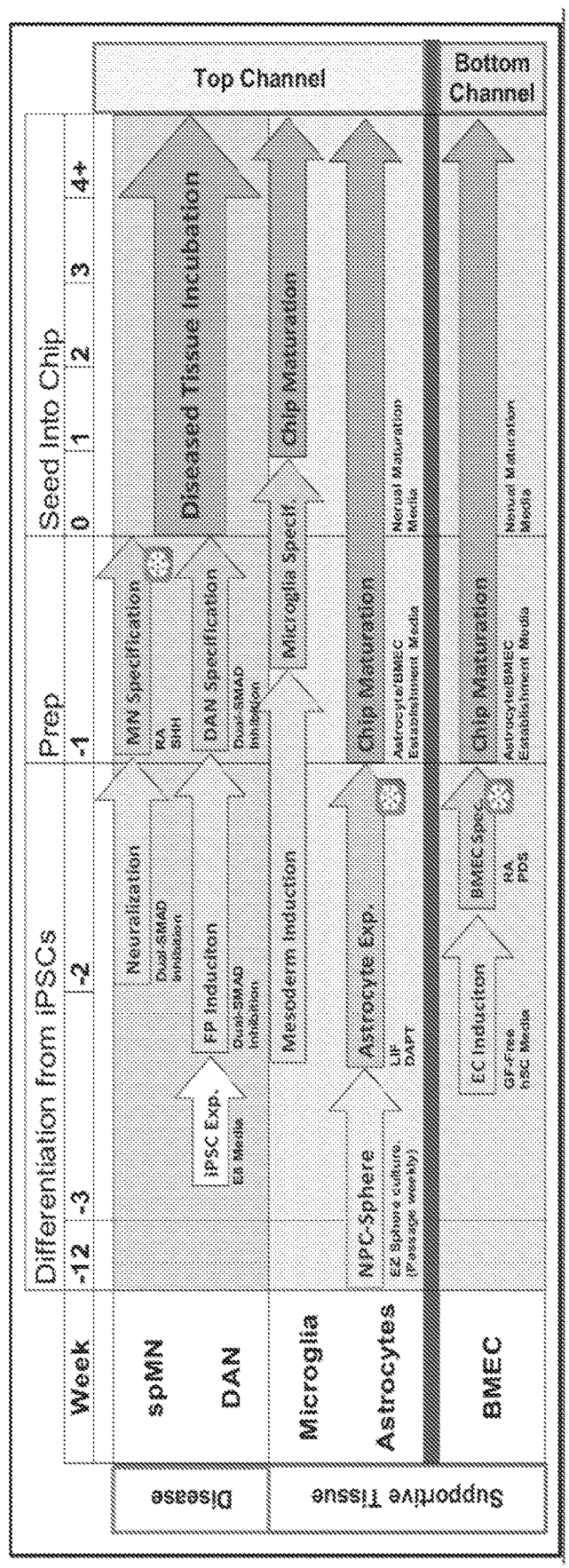
FIG. 12. iPSC-derived tissues can be directed to specific neural, glial and endothelial fates by defined protocols. The Inventors have previously determined the ability of these protocols to be carried out in parallel in preparation for seeding into the chip. Briefly, Astrocytes and BMECs are simultaneously into the chip and allowed to establish during a preparation stage (Prep). spMNs and DANs are then seeded into the chip 6 days later. Finally, microglia are seeded at 1 week and all cell types are allowed to mature under flow. spMNs, Astrocytes, and BMECs can also be generated and frozen into large lots at a stage prior to seeding into the chip (snowflakes). This enables "on demand" seeding of chips and facilitates scaling.
Figure 16:
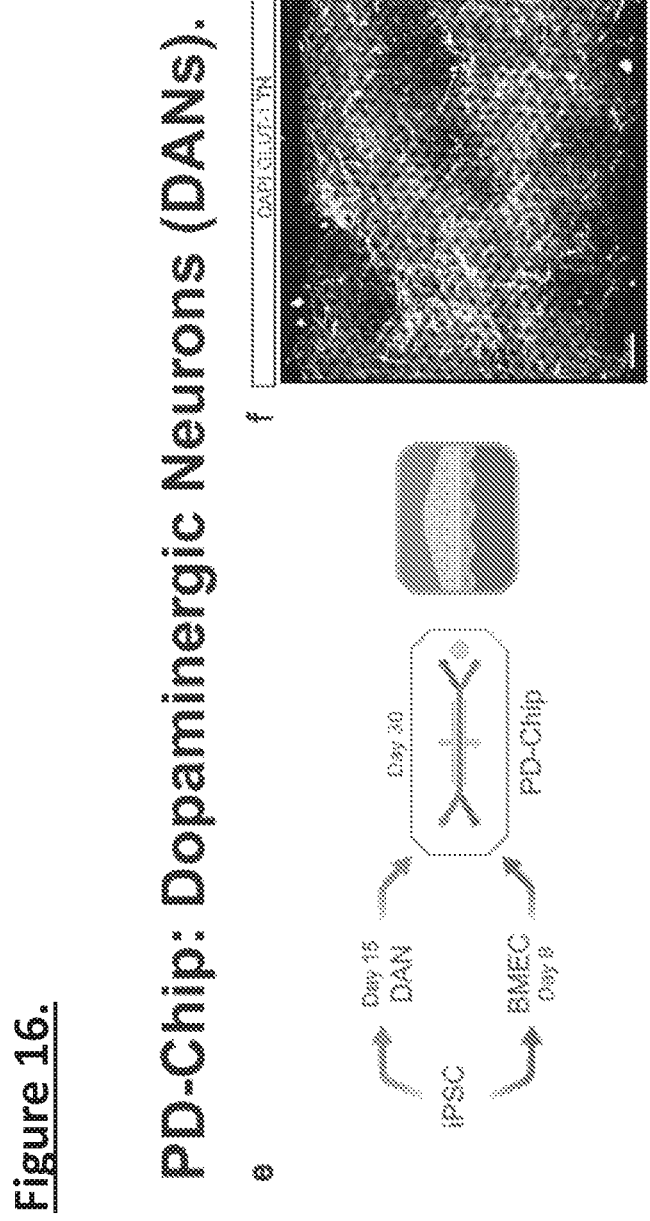
FIG. 16. ALS and PD-relevant Chip platforms for disease modeling studies. (a) Schematic of dual-differentiation and seeding paradigm of ALS-Chip. Both spNPCs and BMECs are generated from human iPSCs and seeded into top and bottom channels respectively. Transverse section of the EC/Spinal Cord-Chip (right) shows two compartments separated by porous membrane. (b) Immunostaining of whole Spinal Cord-Chip at 6-days incubation expressing SMI32 in top channel and ISL1 expressed by BMECs on bottom channel. (c) Maximum projection images cropped at membrane Z-plane show top and bottom compartments of seeding end of EC/Spinal Cord-Chip immunostained with spMN markers SMI32 and islet 1 (ISL1), and tight junction marker zona occludens 1 (ZO-1). Scale bar=400 microns (left) 40 microns (right). (d) Confocal optical reconstruction at along Z axis of Spinal Cord-Chip with computer generated perspective view (top) exhibits confluent layer of BMECs surrounding entire bottom channel. Orthogonal view (bottom) exhibits distinct separation of cultures at 6 days separated by porous PDMS membrane. Scale bar=100 microns. (e) Schematic of dual-differentiation and seeding of PD-Chip. iPSCs are differentiated into dopaminergic neurons (DANs) and BMECs and seeded into the chip at day 15 of differentiation. (f) Immunocytochemistery at day 30 for tyrosine hydroxylase (TH) shows DANs have survived and established in chip (Top). Glucose transporter 1 (GLUT-1) is specifically expressed in the microvasculature of CNS and is expressed in BMECs (Bottom).
Figure 17:
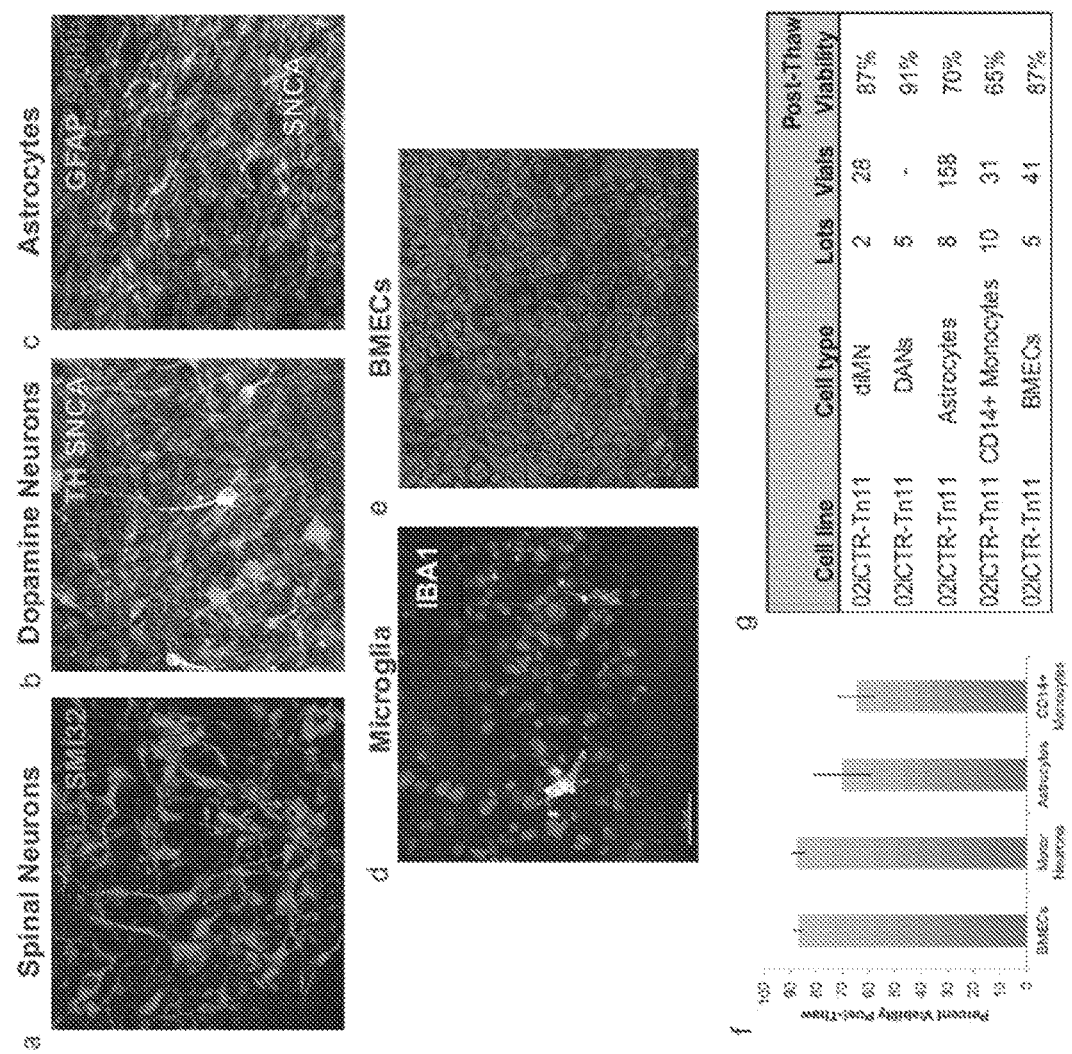
FIG. 17. Spinal motor neurons, dopaminergic neurons, astroctyes, microglia, and endothelial cells are generated from the Non-diseased iPSC line. (a) Spinal motor neurons (spMNs) are differentiated to spinal neural progenitors and frozen at day 12 of differentiation. (b) Dopaminergic neurons (DANs) are differentiated into floorplate progenitors that differentiate into tyrosinze hydroxylase (TH) expressing neurons. (c) Astrocytes are derived from iPSCs and express astrocytic markers GFAP and S100b. (d) Myeloid progenitors are derived from iPSCs from hematopoietic progenitors that can give rise to macrophages. When co-cultured with neurons in the Chip, myeloid progenitors differentiate to microglia-like cells expressing TREM2 and IBA1. (f) Post-thaw viability of cell types from at least two independent differentiations per cell type (g) Table of cell banks for use in Chip experiments. Dopaminergic neurons (DANs) do not contain TH positive cells after thaw, indicating further cryopreservation optimization is necessary FIG. 18. All NVU cell types survive for 28 days on chips. (a) ALS-chip (b) PD-chip. Various dimensional view of chips (c) stained for SMI32, ISL1, GLUT1, (d) stained for SMI32, ISL1, GLUT1, (e) GFAP, S100b, Tuj1, (f) IBA1, DAPI.
Figure 18:
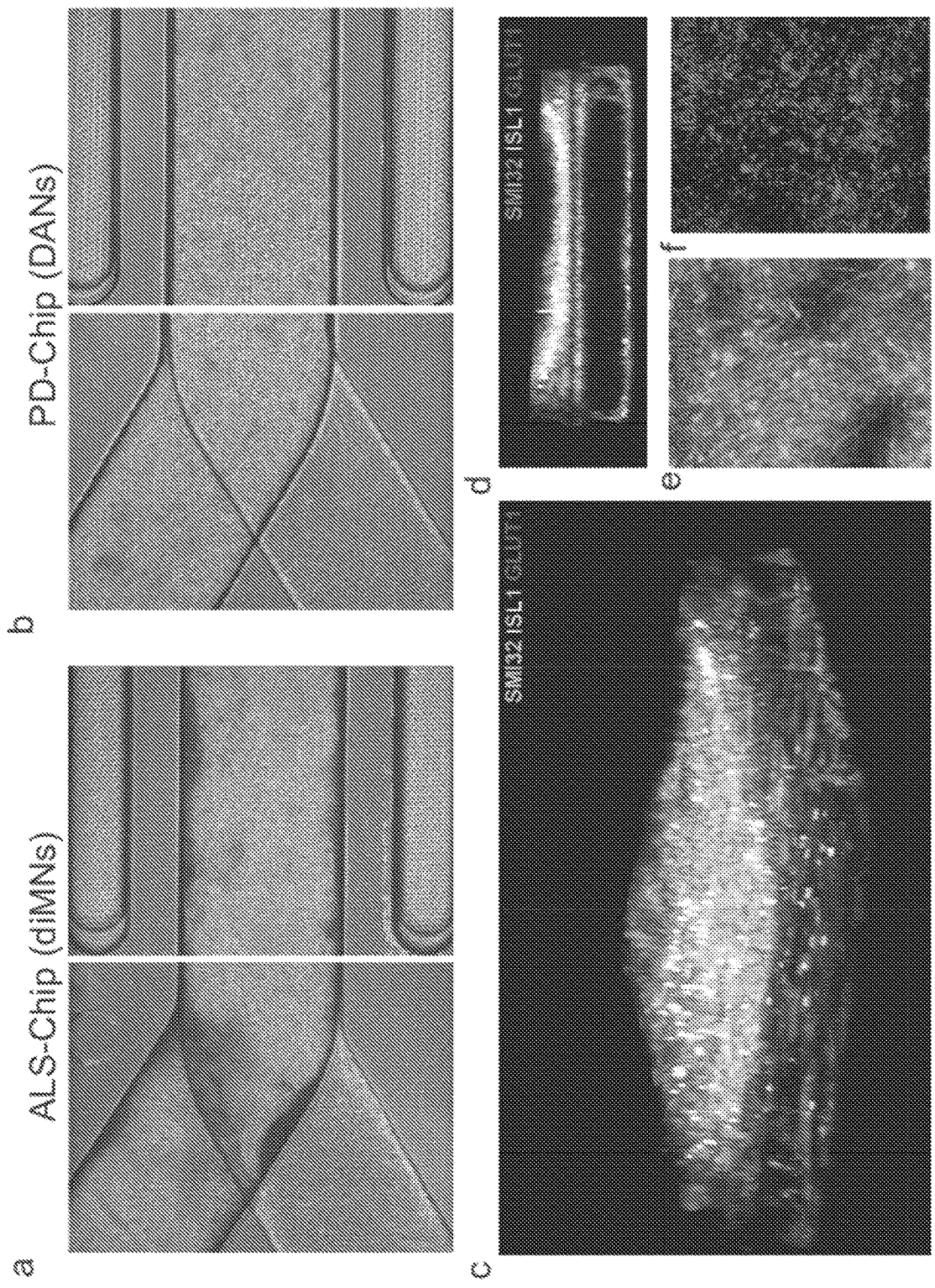
Figure 19:
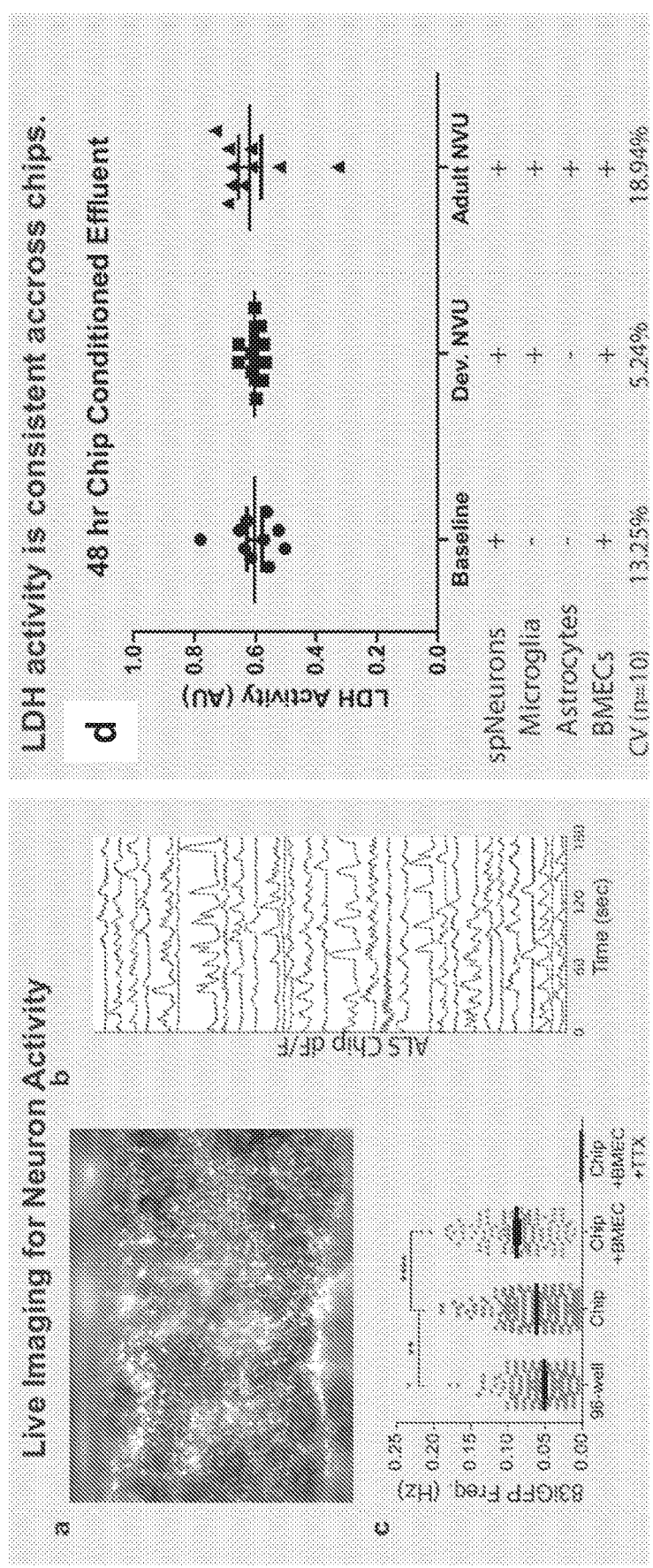
FIG. 19: Comparison of 4 sALS, 4 sPD, 4 control, and 4 SMA lines in the validated spMN and DAN MPS models to identify disease biomarkers. Having determined the optimum conditions and stable sets of potential biomarkers in Aim 1, the Inventors will move to analyzing sALS and sPD lines. Spinal muscular atrophy (SMA) iPSC lines will be used as a positive control, as the Inventors know the Inventors will see specific biomarkers such as lack of SMN. protein and a cell death phenotype. Each chip line (ALS and PD) will undergo a battery (Panel of Assays) of disease relevant analyses on both live and post-endpoint tissue to detect disease-specific biomarkers to aid in diagnostic and therapy development. Neurons are more active in MPS culture. (a) Representative image of spMNs in MPS treated with calcium-activated florescent dye. (b) Transients can be tracked in 300 neurons in each acquisition simultaneously to determine neural function in the chip. (c) Significant increase in transient activity was observed when spMNs were cultured in MPS, and increased further when BMECs were included into the bottom channel. Error bars are reported as standard error of the mean, * denotes ANOVA $P<=0.001$, ** denotes $P<=0.0001$. (d) LDH assay from cell media show stability across chips. Flow-cytometry and 3D imaging enable population and morphometric quantitation of disease relevant proteins. (e) GFP-expressing neurons (GFP+) in ALS-Chip were separated from non-GFP neurons (GFP−) and quantified by FACS. (f) Confocal imaging of DAN cultures stained with tryosine hydroxylase (TH) and alpha-synuclein (α-SYN). Morphometric reconstruction (green) and automated quantification of α-SYN puncta (white) can be conducted to determine disease-specific biomarkers.
Figure 19:
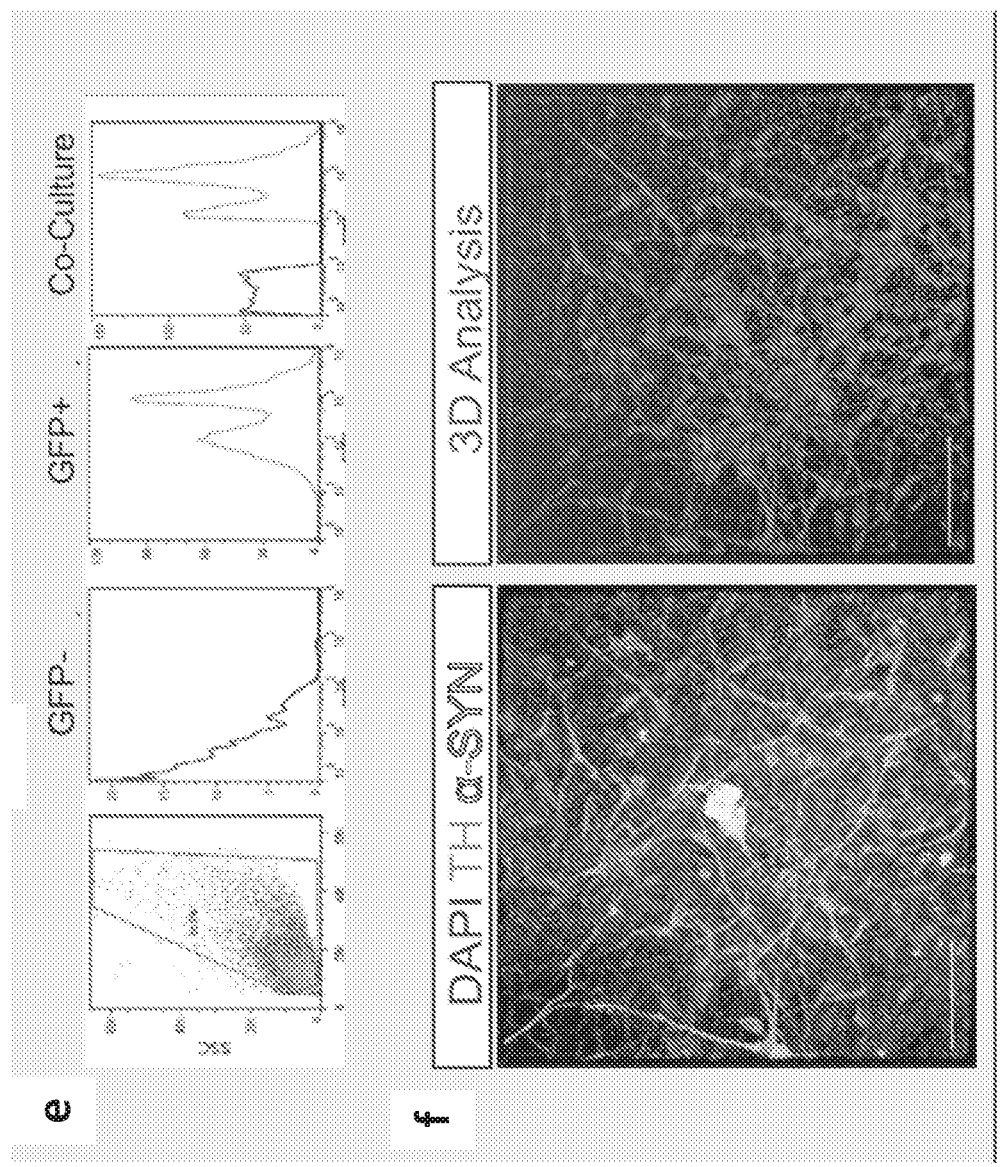
Figure 20:
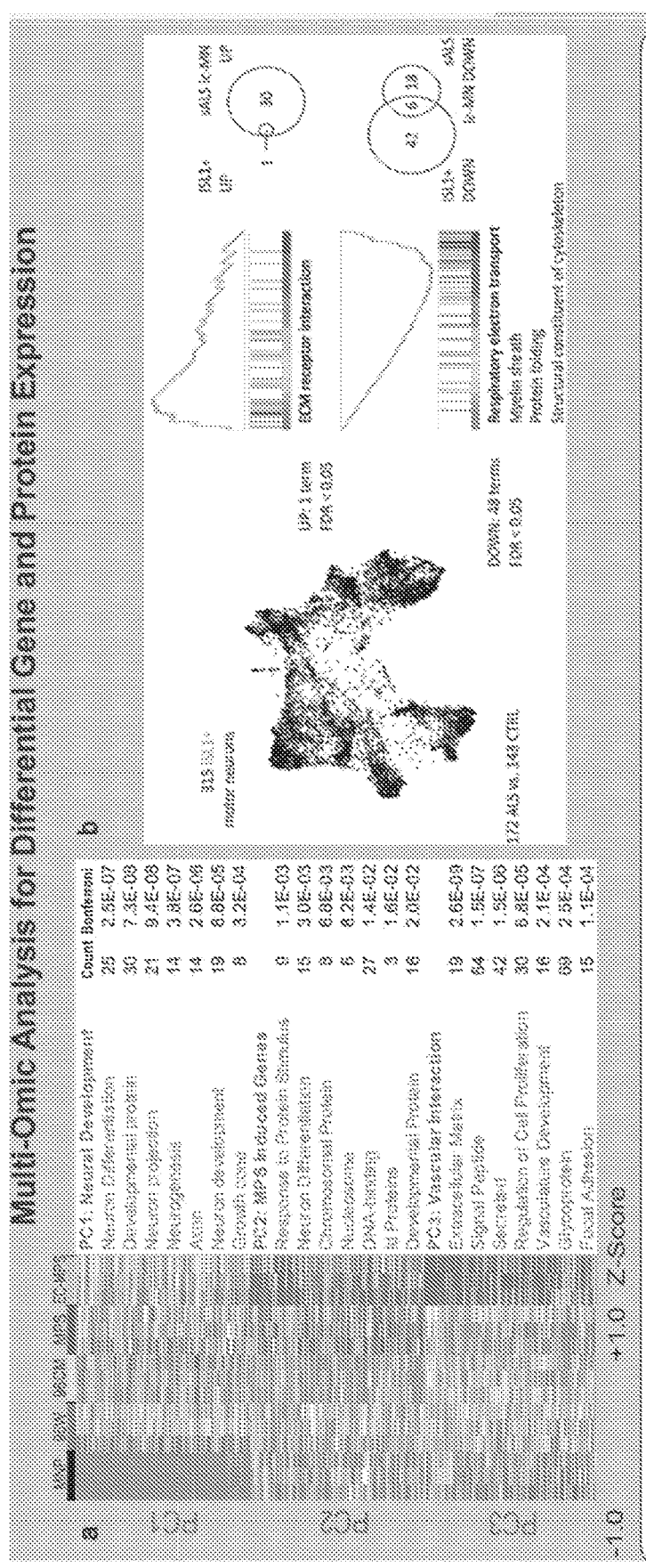
FIG. 20. Bulk and single cell transcriptomic analysis can reveal cell physiology in Chips. (a) Rna-sequencing was conducted on spMNs cultured in the chip (MPS), or in co-culture with BMECs (EC-MPS). Additionally, identical spMNs were cultured in traditional 96 well plates (96W) and in the presence of BMEC conditioned media (96CM). Top ranking gene sets were sorted into pathways using DAVID. Top ranking PC2 genes enriched for pathways involved in protein stimulation and neural differentiation. PC3 gene pathways contained genes known to control vascular interaction, unique extracellular matrix interaction, and increased secreted protein expression. (b) Single cell RNA-seq performed on ALS and control iPSC-derived MN cultures reveal distinct subpopulations within monolayer cultures. Left diagram depicts k-nearest neighbor clustering of single cells based on global transcriptome, and green shaded nodes indicate level of ISL1 expression in subpopulations of cells. Middle diagrams depict Gene Set Enrichment Analysis revealing pathways altered in ALS vs. CTR ISL1-positive cells within these cultures. Right venn diagrams illustrate subsets of these pathways overlap with those found to be disrupted in sporadic ALS (sALS) vs. control laser-captured MNs (lc-MNs).
Figure 21:
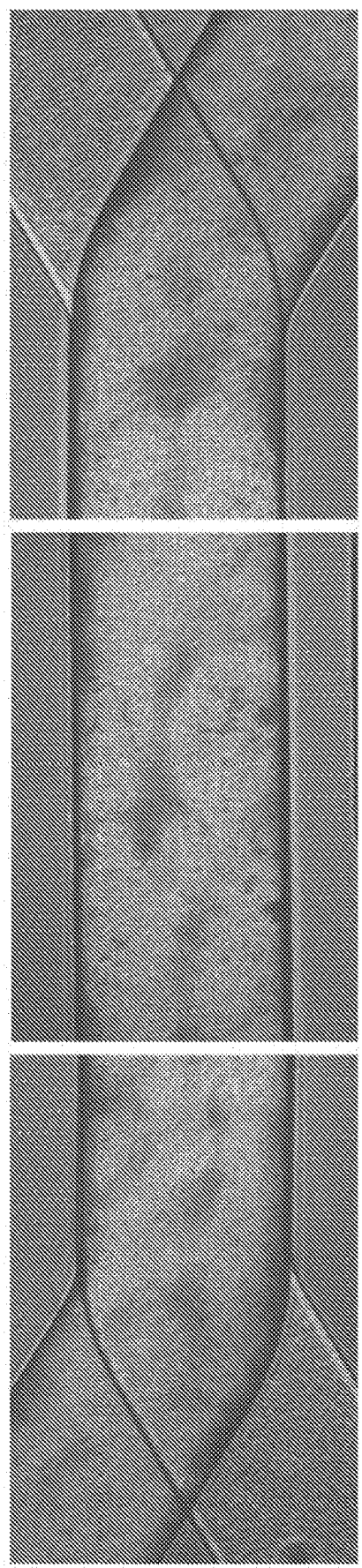
FIG. 21. Picture of channel.
Figure 24:
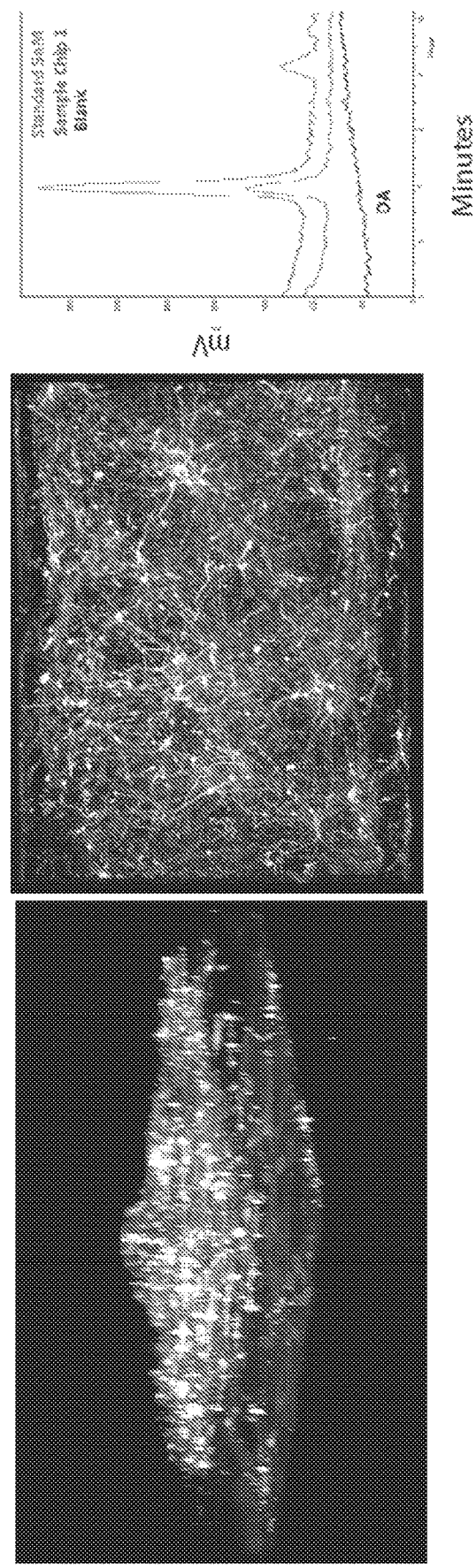
FIG. 24. DA-Chip: Dopaminergic Neurons|Endothelial Co-cultures from human iPSCs. Chip system adapted to include midbrain DA neurons for Parkinson's Disease Modeling. Reproducible TH expression. Blood Brain Barrier component for drug testing.
Figure 25:
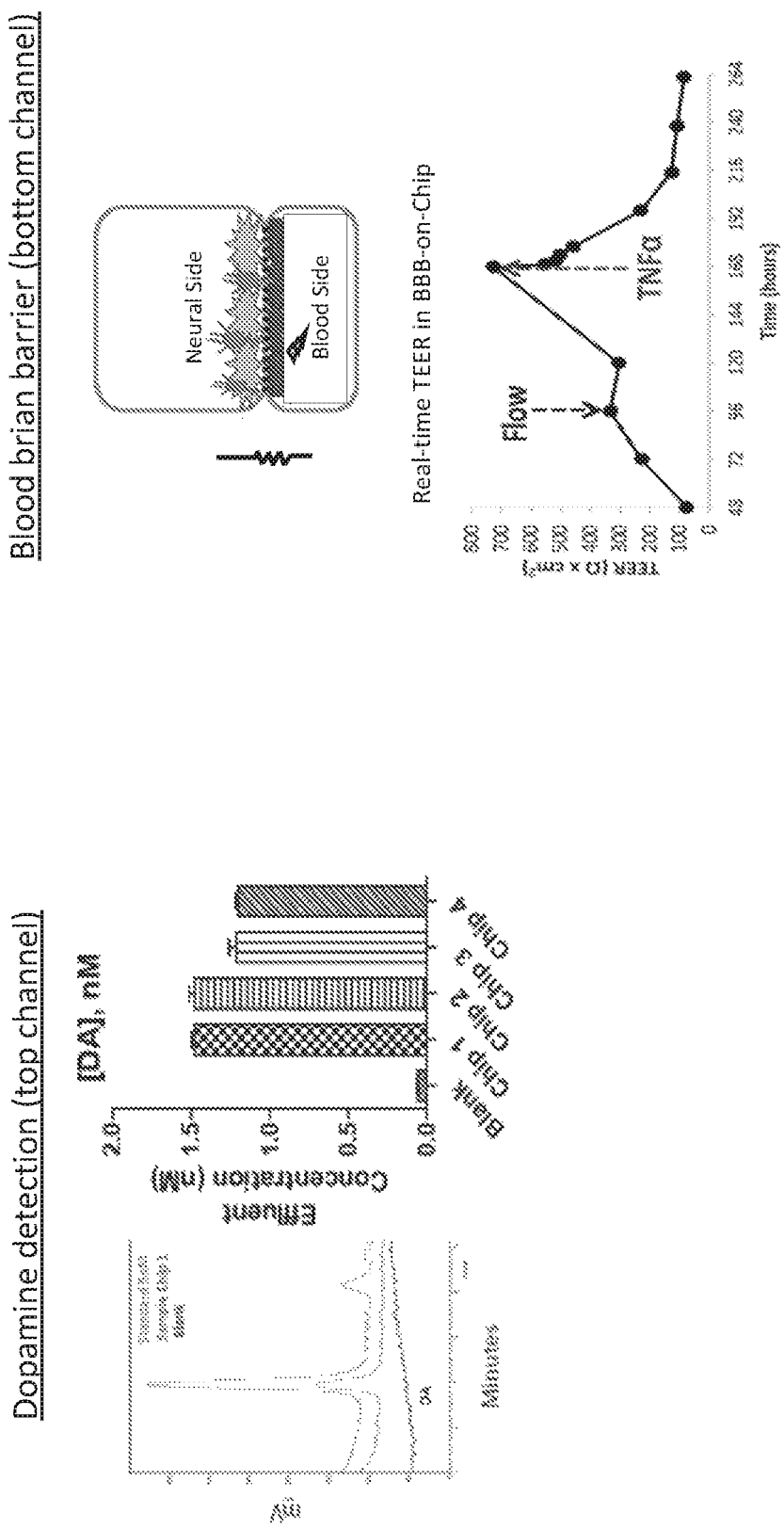
FIG. 25. DA-Chip: Unique culture readouts for drug discovery. DA-Chips produce human dopamine that can be sampled from Chip effluent.
Figure 28:
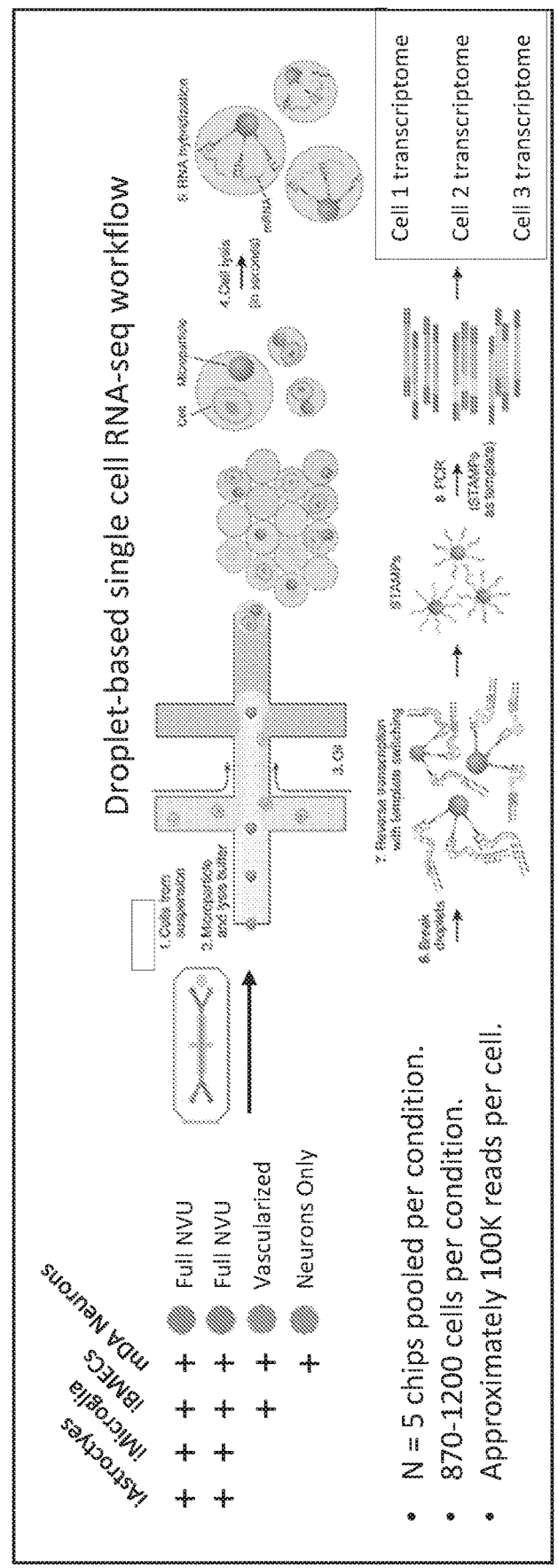
FIG. 28. scRNA-Seq determines functional enhancement of iPSC-derived co-cultures in Chips. Can iPSC derived celltypes in Chip be separated by transcript signature. Are neurons more mature in co-culture with BMECs.
Figure 29:
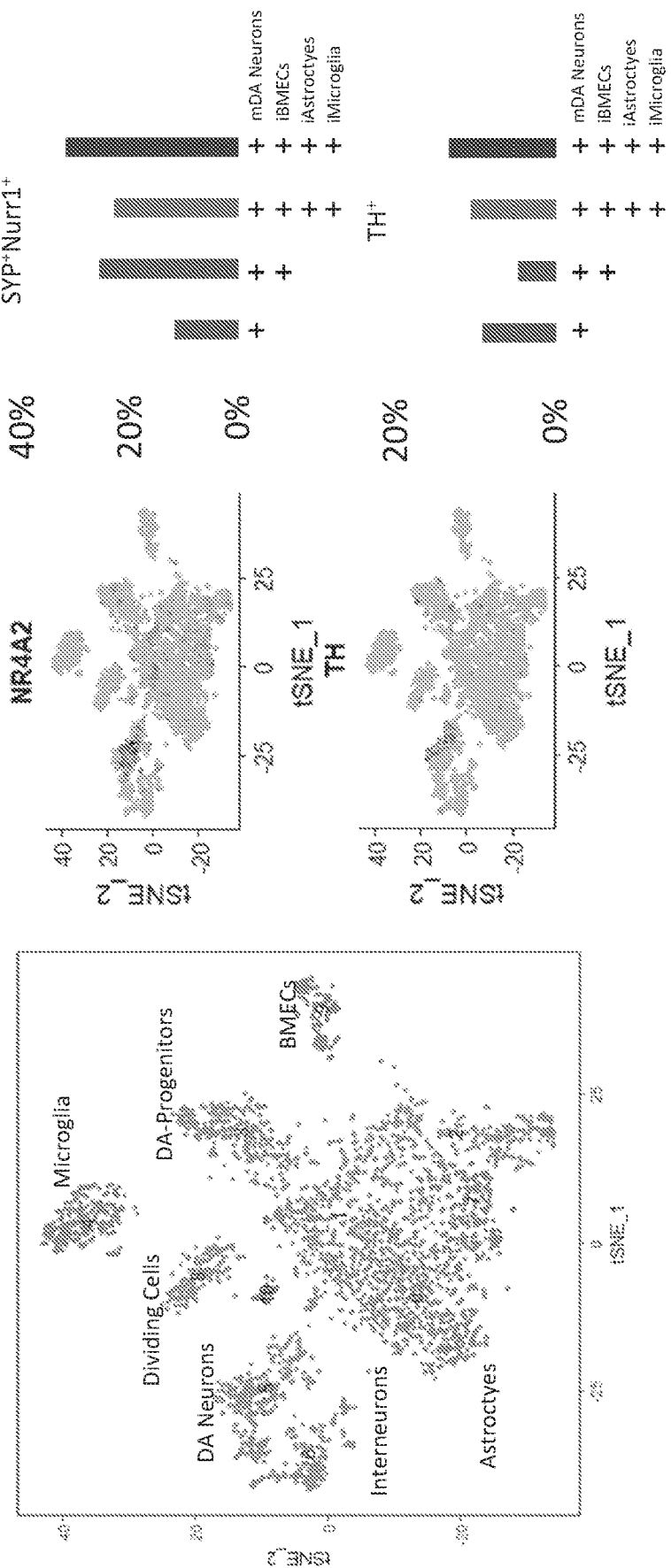
FIG. 29. scRNA-Seq determines functional enhancement of iPSC-derived co-cultures in Chips FIG. 30. Sporadic Parkinson's Disease Patient-Specific Chips have increased Synuclein protein. Lothian control cohort (80Y no comorbidities). Sporadic early onset Parkinson's disease patient cohort. Biomarkers will be confirmed in additional patient Chips.
Figure 30:
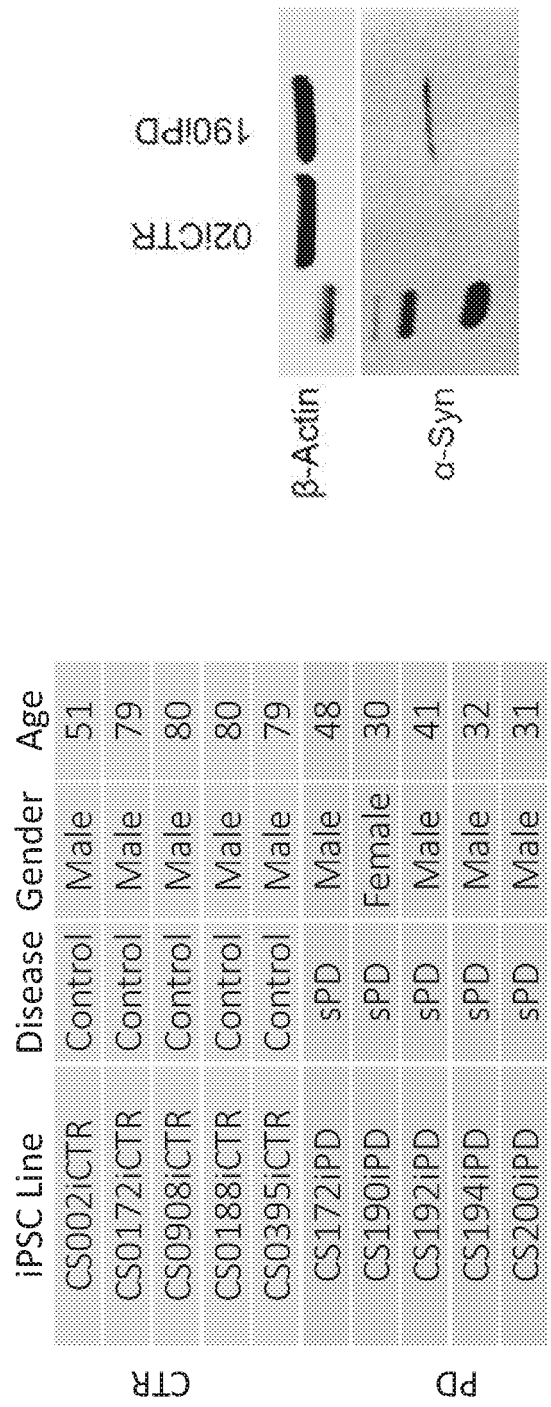
Figure 31:
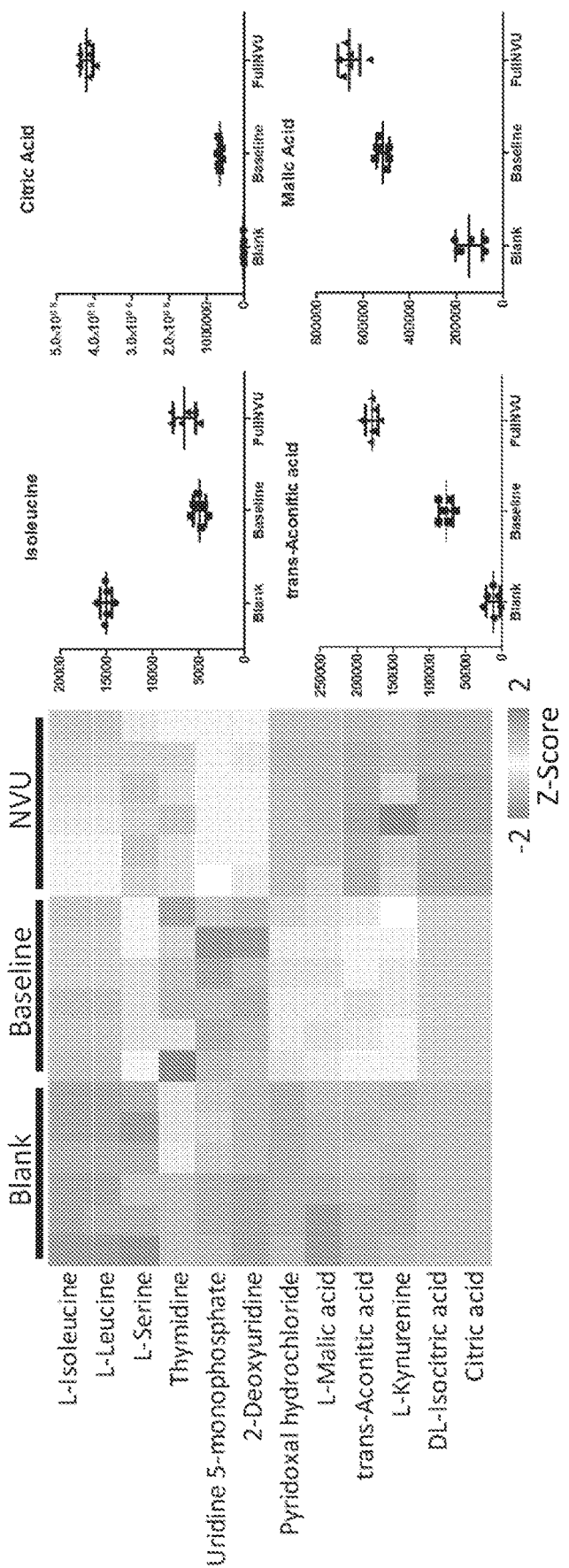
FIG. 31. Metabolomic Profile of Full-NVU Chips
Figure 34:
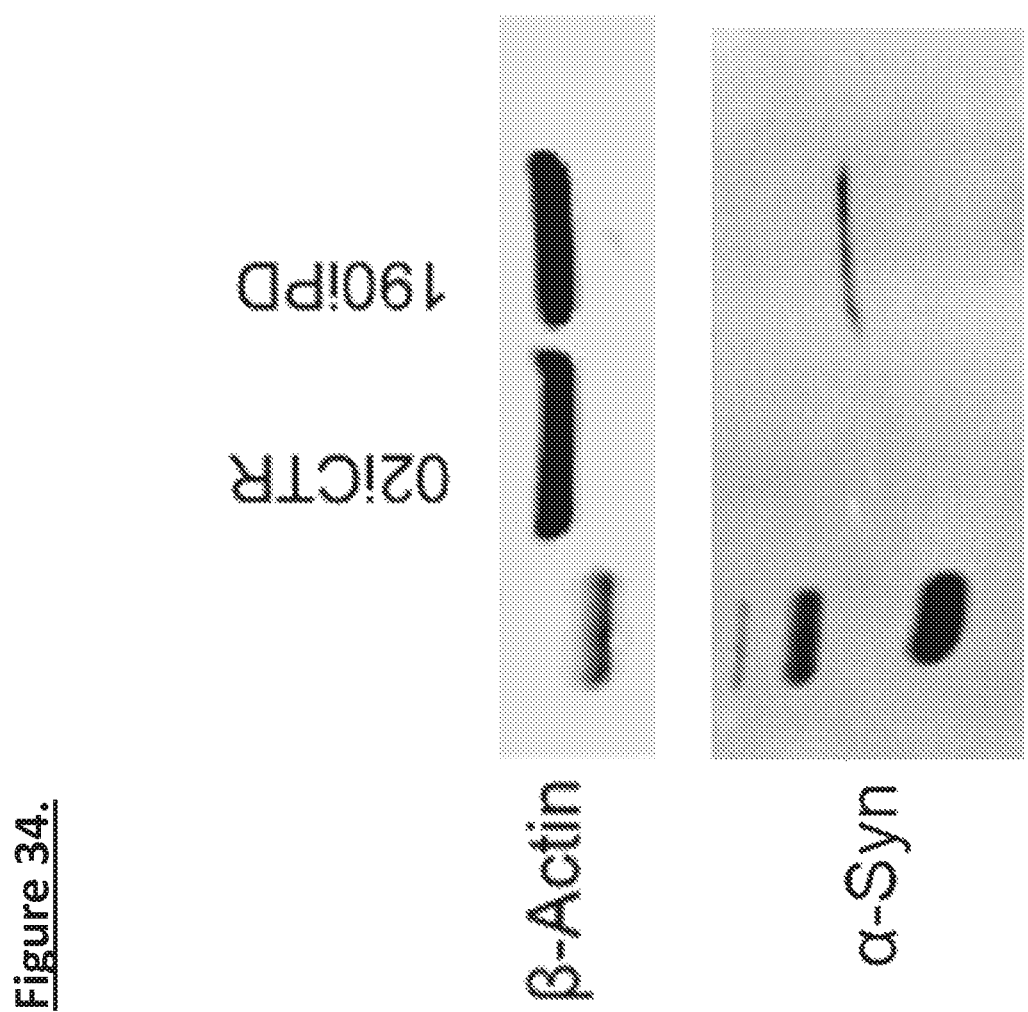
FIG. 34. PD5.1 PD biomarker pilot studyDA. Chips from an early onset sporadic patient and CTR were cultured with Astrocytes and BMECs for 30 days. SNCA accumulation was observed via western blot that is consistent with current off chip modeling studies. Expected to be a major biomarker for larger patient trial.
Figure 35:
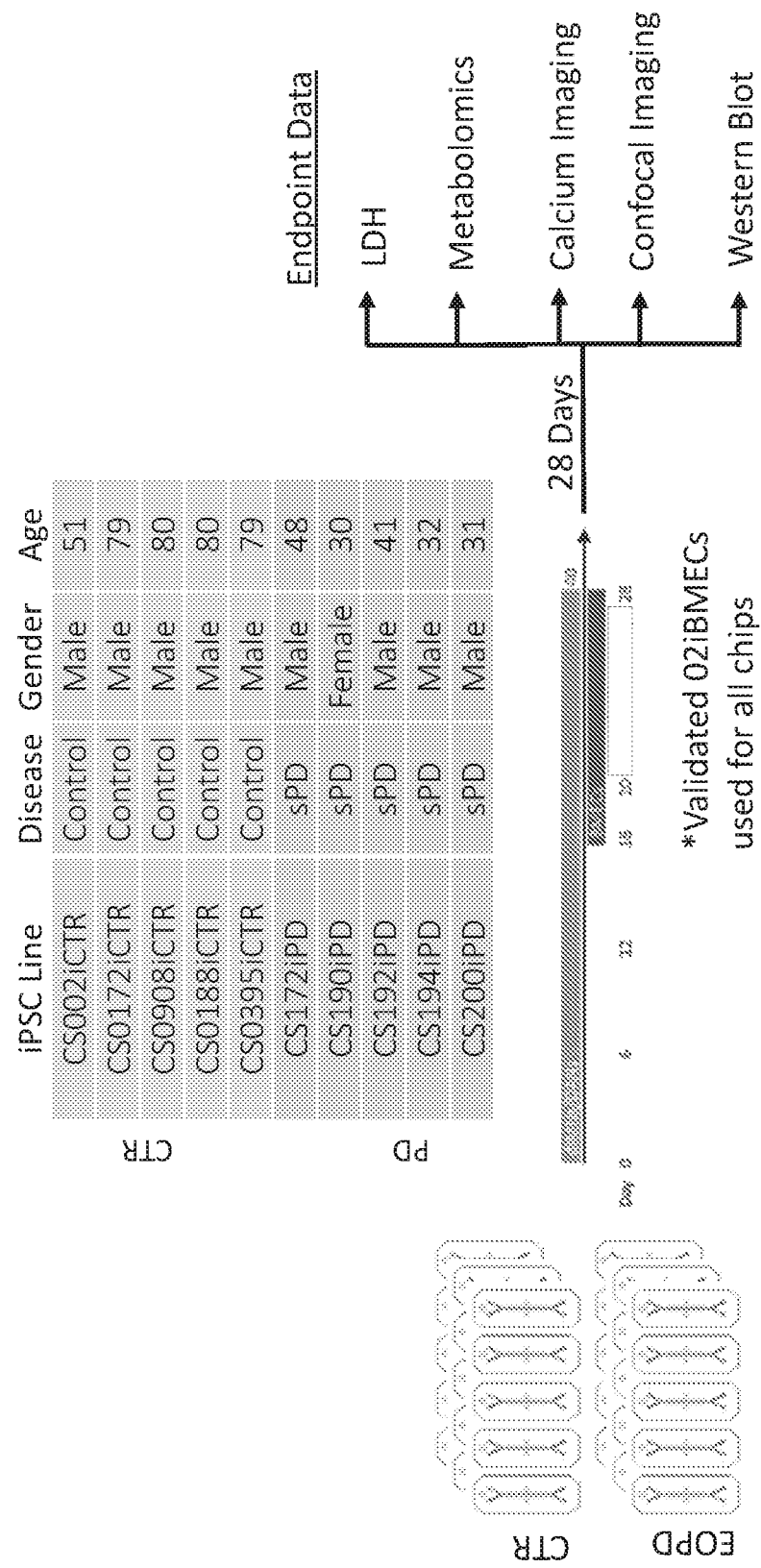
FIG. 35. PD5.1 Biomarker Discovery Study Paradigm. Schematic of PD biomarker study. 5 independent donor lines from each condition (CTR vs PD) were cultured in replicates of 3 per line. Culture paradigm included midbrain neurons cultured in chip for 14 days, then BMECs were added and cultured to endpoint. Endpoint data listed to the right.
Figure 36:
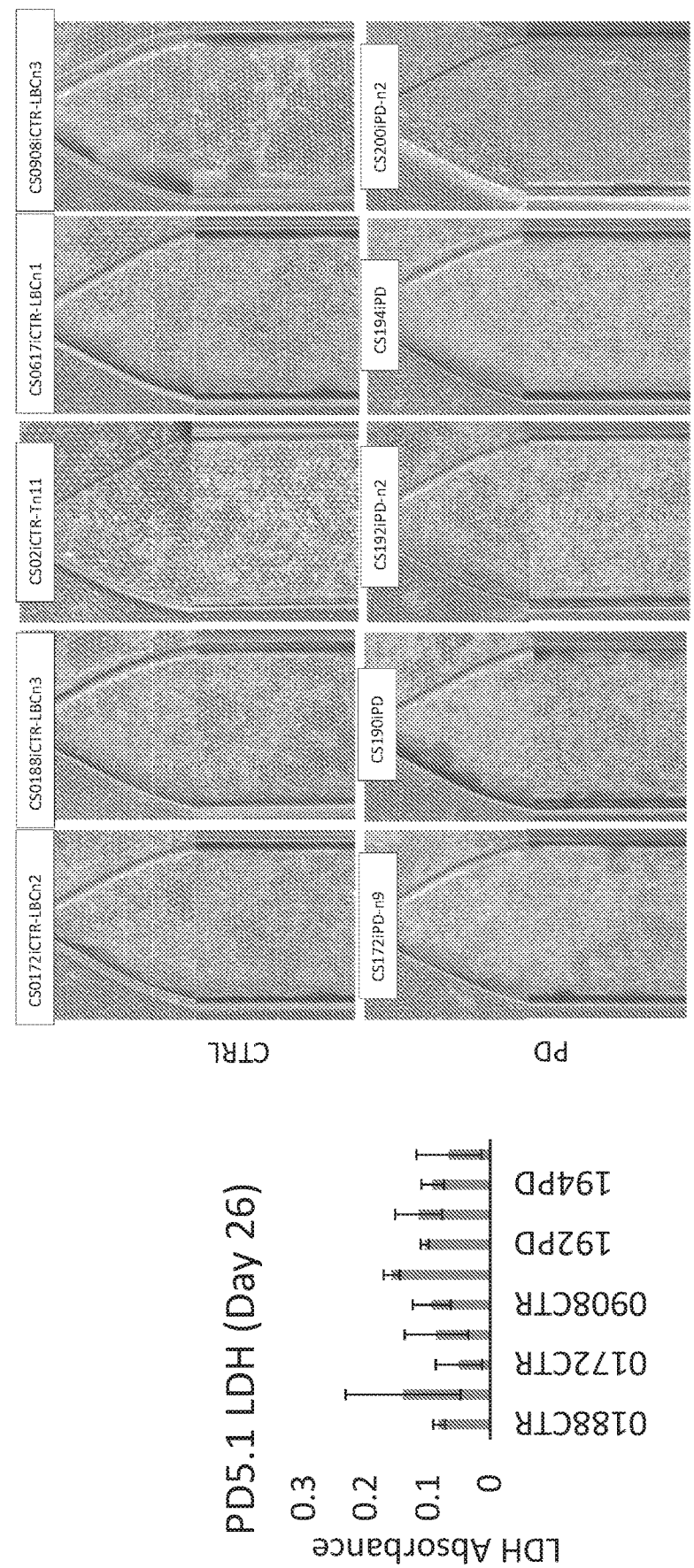
FIG. 36. PD5.1 DA-Neuron Baseline Chips (30 chips total). Representative culture images at 10× of each patient chip (seeding and main channel). Lactate dehydrogenase (LDH) activity of neural effluent at endpoint. BMECs very stable across chips. No PD specific cell death observed.
Figure 37:
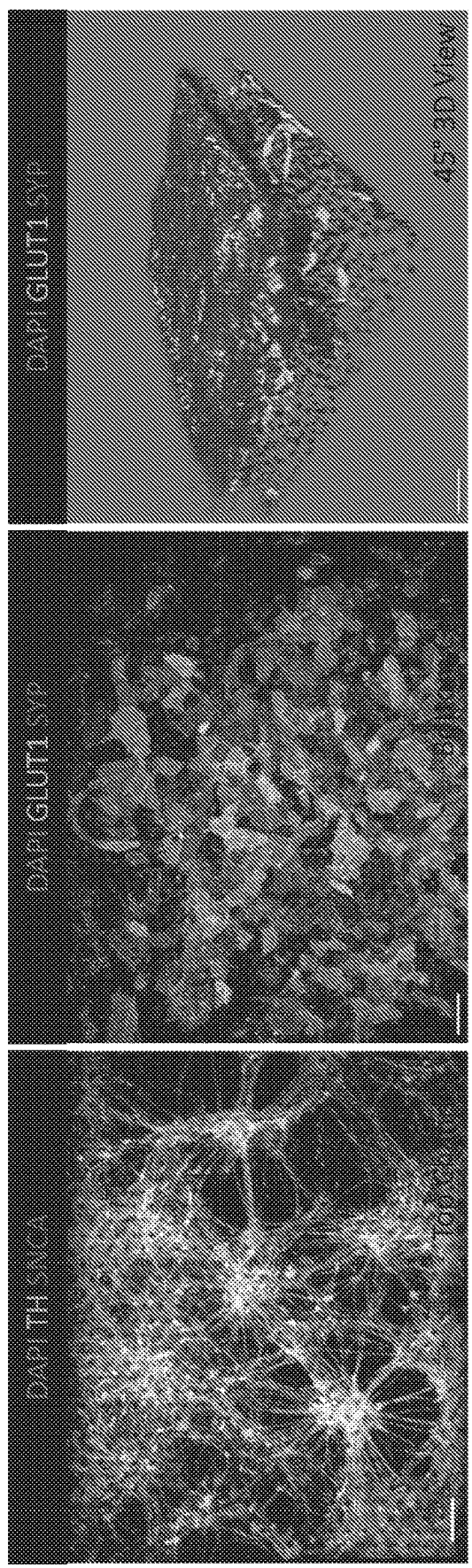
FIG. 37. DA-Chips express markers relevant for PD study. 0172 Control Chip expressed dopaminergic neuron and BMEC markers. All chips were not imaged due to degradation of staining (>2 weeks). Confocal florescent images of midbrain chip from 0172iCTR. Top channel image shows tyrosine hydroxylase (TH), alpha-synuclein (SNCA), and DAPI staining. Bottom channel shows Glut-1 expression lacking synaptophysin positive neuronal staining. Z-stack reconstruction (right) shows separation of vasculature and neural tissues in top and bottom compartments respectively.
Figure 39:
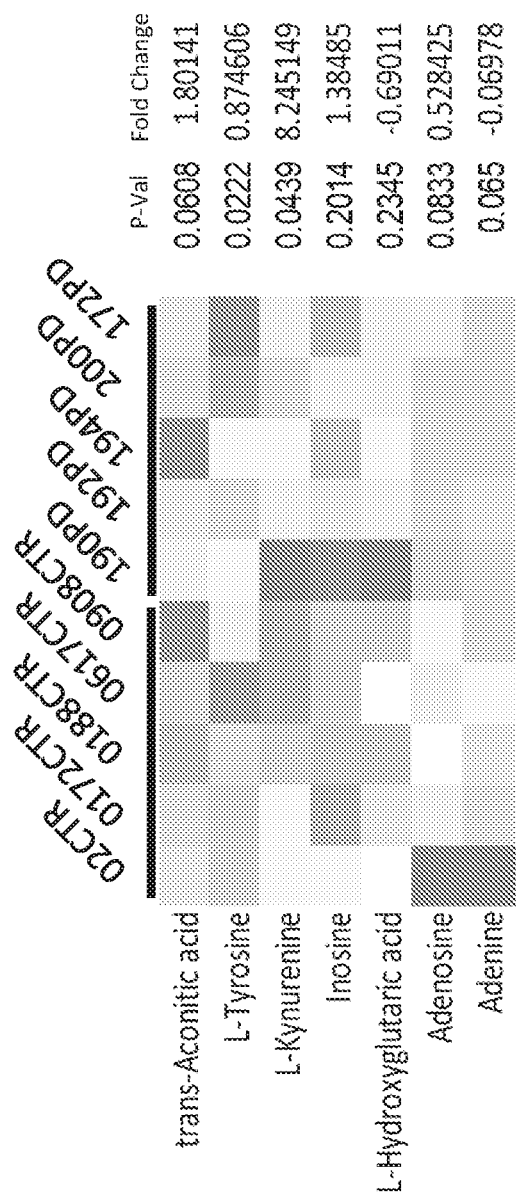
FIG. 39. Metabolomic signatures of PD vs CTR DA-Chips effluent. DA-Chips generated at day 28 from 5 lines per group, 3 Chips per line (30 chips total). 25 ul neural media conditioned for 24 hrs in Chip and collected for analysis. 63/219 metabolites passed QC (30% CV) across replicates. 2 metabolites significantly dysregulated in PD samples (t-test)
Figure 40:
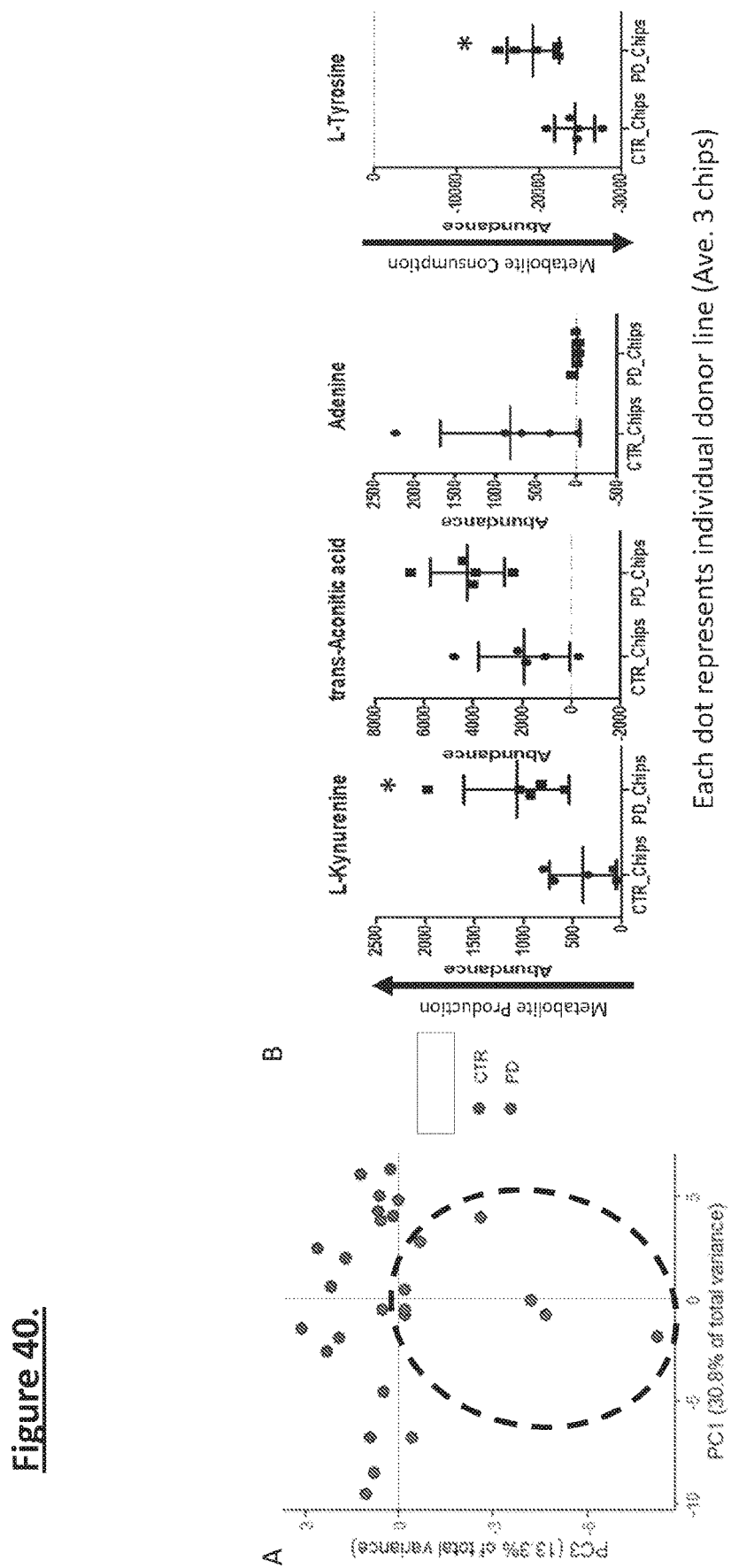
FIG. 40. Metabolomics M5.1 (DA-Chips). (a) PCA on all metabolites: PC3 trends toward separation of disease from control chips (dotted line). Blank Chip media subtraction shows altered production and consumption of metabolites in PD chips. (b) Metabolomic profiling of neuronal effluent at endpoint after 24 hours of conditioning (static). PCA plot of metabolomic dataset containing 41 unique metabolites. Circles indicate individual chips. Top differentially detected metabolites across PD vs CTRL chips. Abundance reported after subtraction from blank media. * $P<0.05$ t-test.
Figure 41:
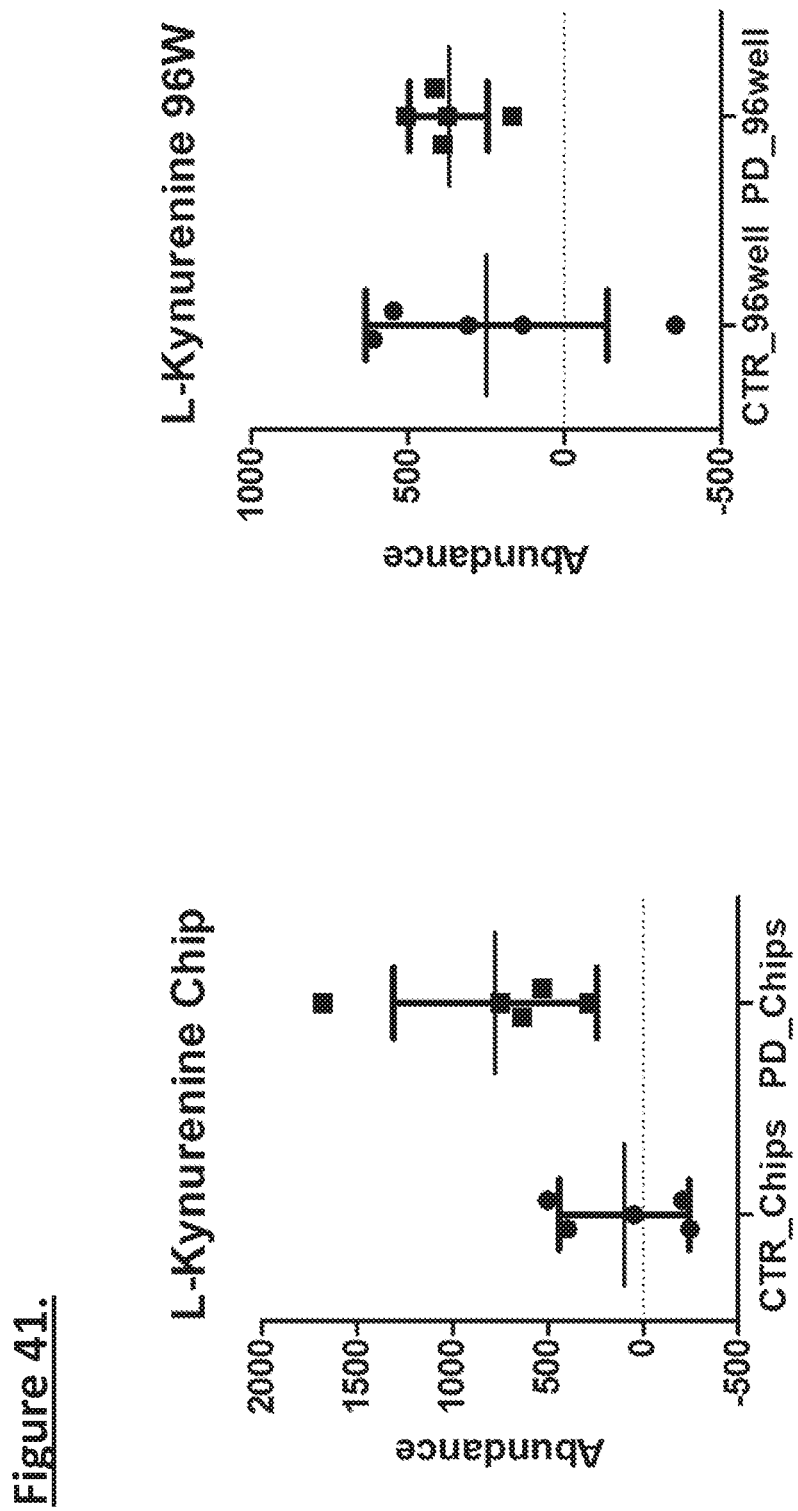
FIG. 41. Kynurenine biomarker specific to Chip cohorts. Kynyrenine 2.7-fold increase over Average CTR Chips, though variance in sporadic PD lines observed. 96 well plates do not have same effect, could be due to enhanced culture of chip or BMEC co-culture.
Figure 42:
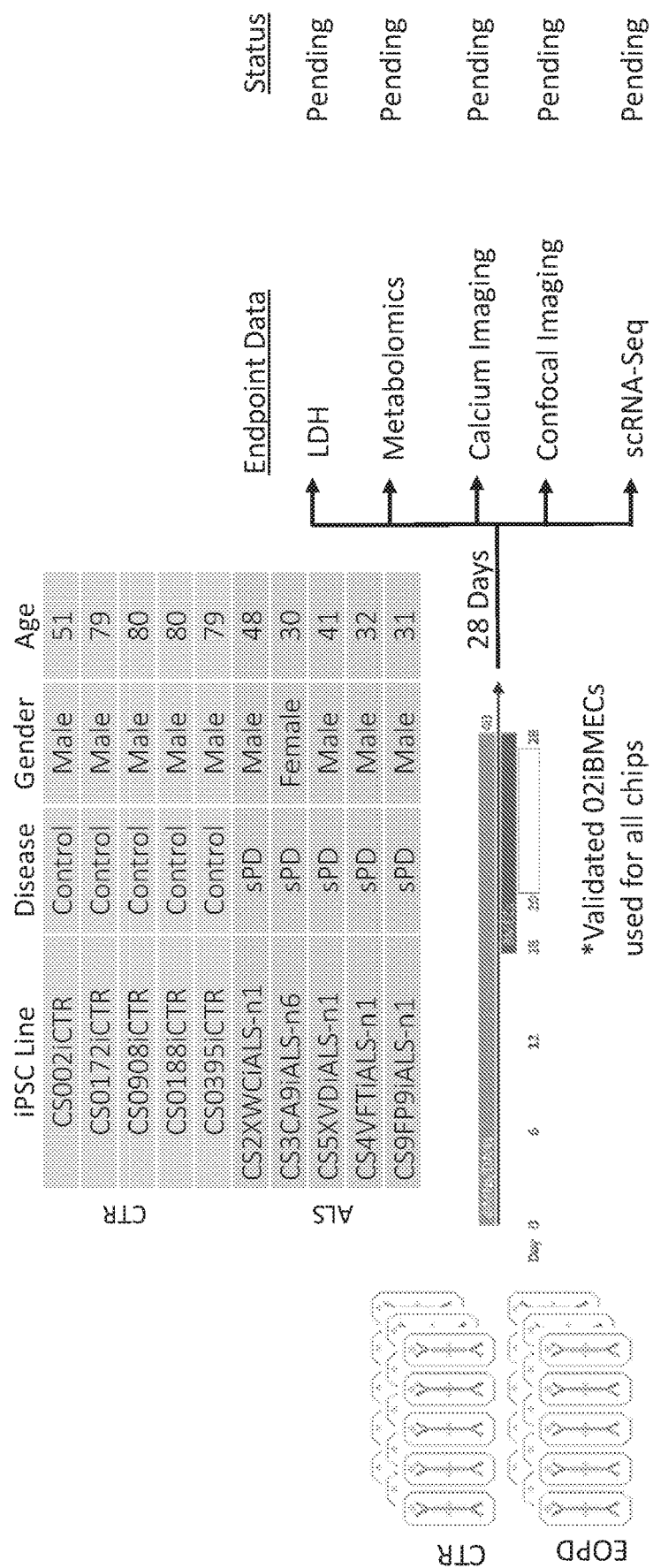
FIG. 42. ALS5.1 Biomarker Discovery Study Paradigm
Figure 43:
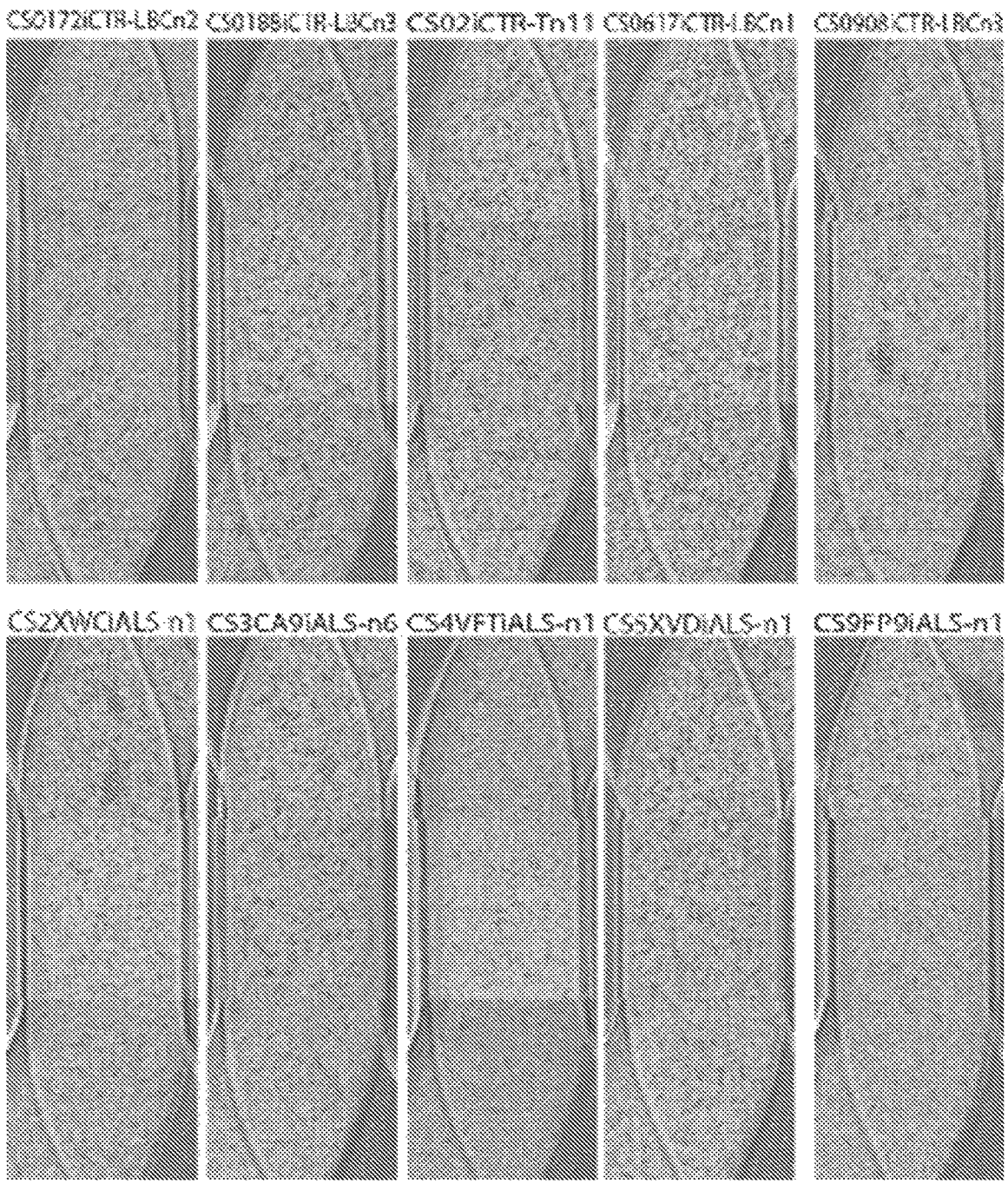
FIG. 43. Sporadic ALS vs Lothian Control MN-Chip Cohort. 40 Chips seeded with motor neurons from 10 patients. Low variance observed across chips (Day 5). LDH, and metabolomic profiling will be conducted at 14 and 28 days.
Figure 44:
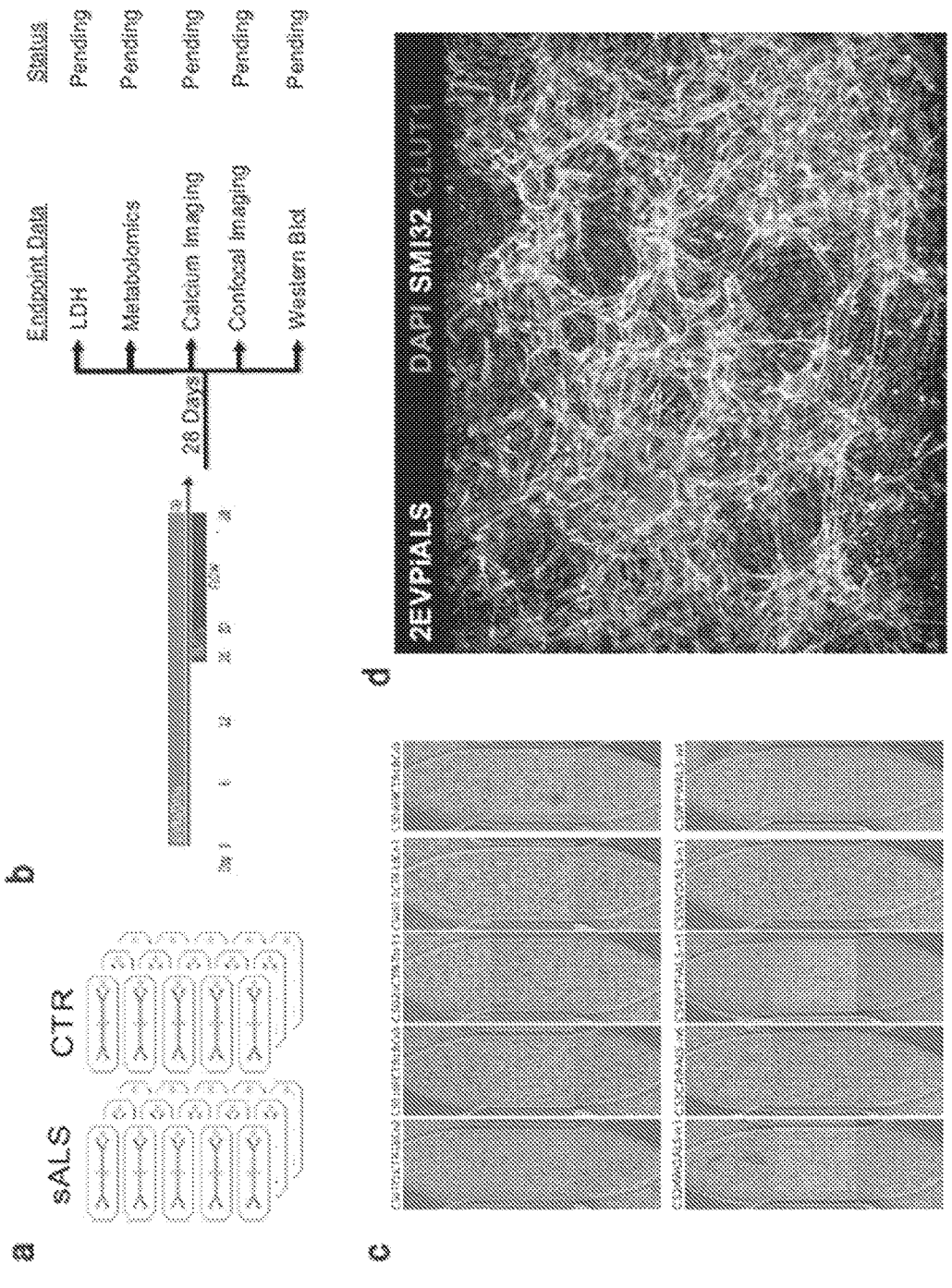
FIG. 44. Schematic of PD biomarker study. (a) 5 independent donor lines from each condition (CTR vs PD) were cultured in replicates of 3 per line. (b) Culture paradigm included midbrain neurons cultured in chip for 14 days, then BMECs were added and cultured to endpoint. Endpoint data listed to the right. (c) Representative culture images at 1× of each patient chip (seeding and main channel). (d) Lactate dehydrogenase (LDH) activity of neural effluent at endpoint.

In the Inventors' previous work in developing MPS models of PD and ALS, the Inventors established seeding and co-culture methods of neurons with either BMECs alone or with astrocytes and BMECs. The Inventors' studies conducted on spMNs under constant flow conditions have shown BMECs to be necessary for neuronal establishment under continuous flow. BMECs and astrocytes were also shown to survive in co-culture with DANs and remain stable for 3 weeks under pulsatile flow. Importantly, these BMEC and astrocyte cell types can be cryogenically stored in lots (FIG. 12). Previously validated astrocytes and BMECs can then be thawed, seeded directly into organ-chips, and matured in preparation for co-culture with PD or ALS-relevant neuronal tissues.

Figure 5:
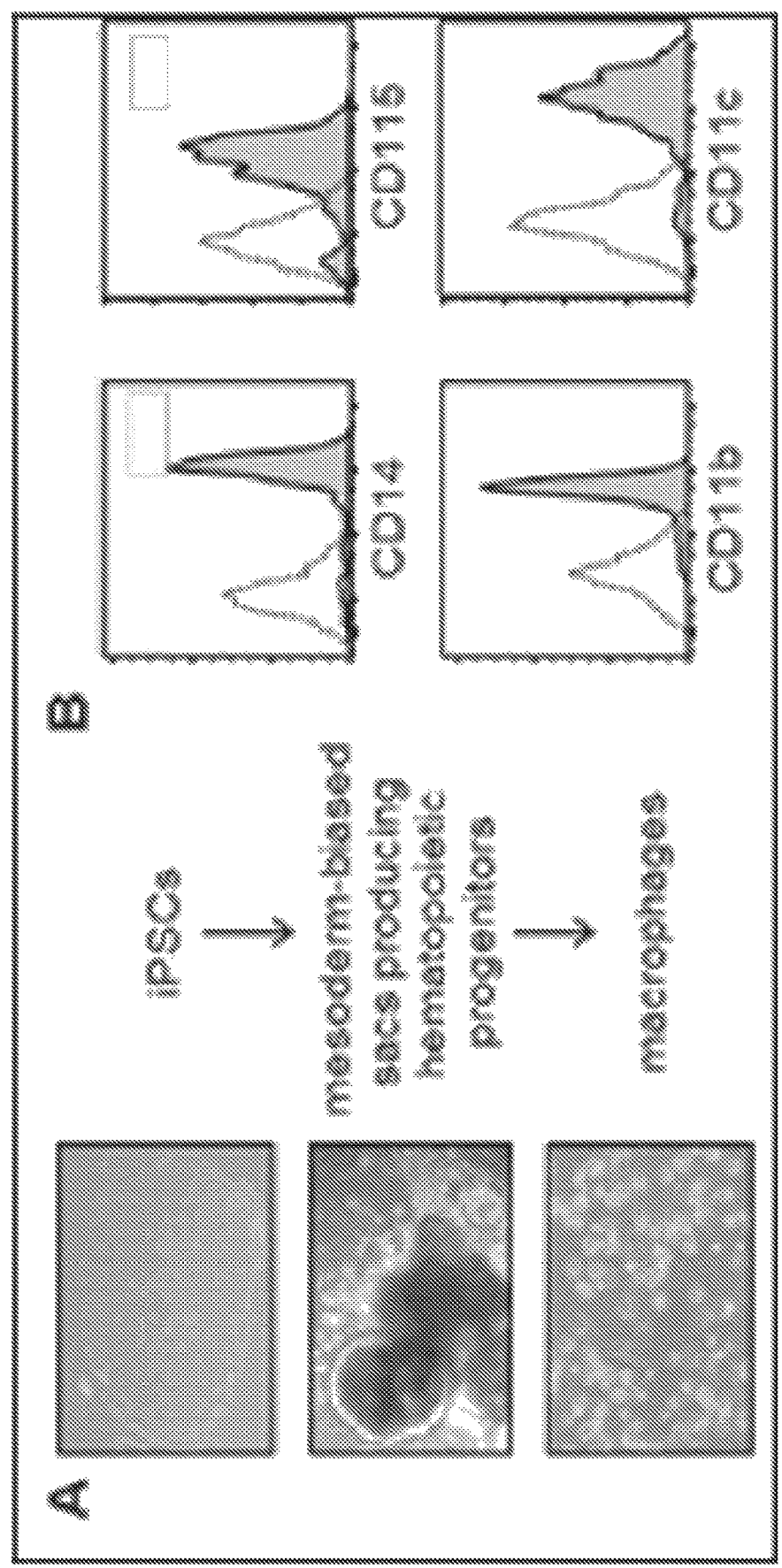
FIG. 5. (A) Cedars-Sinai has developed a robust protocol for the efficient differentiation of CD115-positive microglia from human iPSC-derived macrophages. (B) FACS shows that cells express microglial markers implicated in neurodegenerative disease including CD11b and CD11c.

The Inventors expect this on-demand availability of these supportive cell types will aid in scaling of the Inventors' system in later experiments. Beyond BMECs and astrocytes, microglia are required for normal neuron development and have been implicated as an important cell type in ALS and PD disease pathogenesis. Recent protocols have been developed (FIG. 5) for differentiation of functional microglia that could elicit distinct neuronal physiology and disease phenotypes in the MPS. In light of this, the Inventors combine BMECs, astrocytes and microglia within each disease model system to achieve a functional platform that will be used in later aims.

Example 2

Development of Reliable APS Models of Control iPSC-Derived MNs and DANs

Prior studies by the Inventors seeding neural and endothelial cells with MPS devices described above has shown that both spMNs and DANs can differentiate in co-culture with BMECs seeded into the opposite channel. Without being bound by any particular theory, it is believed that addition of astrocytes and microglia will strengthen the model further. For example, Microglia are also a cell type that has been implicated in neurodegenerative disease and is known to lose function in traditional forms of culture. The MPS could therefore allow this cell type display novel biological and disease related physiology for the first time in vitro.

Initial studies have included seeding organ-chip with iPSC-derived astrocytes in the neural side and BMECs in the blood side 1-week prior to seeding neurons. Preliminary results indicate that the astrocyte layer increases stability of both the neural and blood compartments. To assess the utility of astrocytes and microglia in platforms for both spMNs and DANs, the Inventors will utilize standard PDMS chips with PET membranes for attachment of cells with 3 micron pores. This semi-porous barrier is large enough to allow astrocyte end feet projection, but small enough to inhibit significant neural or BMEC migration.

Initial studies will focus on 25 control iPSC lines generated from the Lothian cohort in Scotland. Here, patients between 60-80 years of age have been followed for many years and shown to be neurologically normal. One of these lines will be used as a standard control line for production of spMNs, DANs, BMECs and astrocytes. The Inventors will use a limited panel of biomarkers as outcome measures.

Example 3

Use Astrocytes and Microglia to Enhance Potential Biomarkers Through Maturation of spMN and DANs Either spMNs or DANs are cultured in chips under 4 different conditions: (i) neurons alone in the top channel (ii) neurons in top channel with BMEC in the bottom channel (as in FIG. 2). (iii) neurons seeded into chips pre-coated with astrocytes in top channel and BMEC on bottom channel and (iv) neurons and microglia (FIG. 5) seeded into chips pre-coated with astrocytes in the top channel and BMECs in the bottom channel. One can produce microglia using a cytoplasmic florescent reporter line under a constitutive promoter so that one can determine their persistence in the cultures. This overcomes difficulties characterizing these cells with specific markers. Both channels can have 10 µl flow rates, which appear to be optimal for neural and endothelial cell survival.

Cultures are analyzed at either 2 weeks or 4 weeks post-seeding to establish how the co-cultures mature over time in the devices. The 4 cell combinations will be scored depending on three essential parameters to determine feasibility for future studies: (i) calcium transient activity for neuron function, (ii) immunostaining for support cells to determine co-culture stability, (iii) neuron morphology to determine neuronal establishment, and (iv) metabolites including neurotransmitter production (Table 1). Successful scores are determined by high transient activity, adequate distribution of supportive cell types, neuronal morphology that allows for adequate imaging analysis and soma sizes that are indicative of neuronal health. These experiments are repeated three times in order to assess variability between runs.

Example 4

Determine Whether MPS Cultures Show Reliable Biomarker Expression Across Multiple Experiments Based on highest scoring seeding combination, a more expansive phenotypic outcome measure is applied. This includes comprehensive matrix of cellular assays that combine the major assets of the MPS with multidisciplinary cell physiology readouts (Table 2).

The following are assessed at four weeks in culture: (i) metabolomic profiling with mass spectrometry metabolic biomarker expression are determined in the effluent from the MPS devices, (ii) neuronal electrophysiology are analyzed as the cells mature in the MPS device using live calcium imaging, (iii) MPS devices are analyzed post-experiment to assess the morphology and survival of MNs and DANs using high content imaging and (iv) whole proteomic and transcriptomic profiling are carried out to explore more potential biomarkers that are consistently expressed in these devices.

The Inventors have carefully considered complementary assays to be conducted on the same sets of chips to reduce overall chip requirements. A full description of these techniques is provided in Table 2 with further examples described herein. These experiments are repeated 3 times using the same control iPSC line at a similar passage number (Table 3). The biomarkers selected for future screening should show no significant differences ($P<0.05$) between runs based on ANOVA assessments of each data set.

Live Calcium imaging—Calcium-activated florescent dye Fluro-4AM (thermo) applied to the neural channel in the MPS allows for optical detection of neuronal activity. The Inventors can perform acquisitions using a high speed CMOS camera of up to 200 frames per second. Videos of live flashing neurons in the MPS are quantified using custom MATLAB software to determine calcium the number of transient events, and in turn neuronal activity. This high throughput assay can accurately measure large cohorts of neurons simultaneously. As cultures mature, waves of calcium activity are observed. Percent synchrony and number of waves are additional measures that are easily identified by this assay. The Inventors will define maturation as increased numbers of spontaneously active neurons in the culture (see FIG. 3) over controls and the numbers of synchronized "waves" of activity indicative of maturity (FIG. 8).

Metabalomics—The Inventors plan to routinely collect effluent from the Organ-Chips and analyze them by MS using the metabalomics assay. At 4 weeks, the Inventors will collect media effluent manually from outlet reservoir, process the samples in triplicate and inject into the LC-MS/MS system. This will give us a dynamic readout of cellular health within the chip and serve as the basis of a low throughput drug assay system for use during the UG3 portion of this award. Metabolite extraction is accomplished using methanol extraction with samples dried using no heat conditions and stored at −80° C. until further use. The analysis is done with the coupling of liquid chromatography and 6500 Triple Quadrupole (SCIEX), will provide a sensitive and highly selective system for the detection of targeted metabolites from extracts. In addition, neurotransmitter release is monitored, both at steady state and with addition of compounds. Neurotransmitters are included in the list of metabolites detected and analyzed including dopamine, serotonin, GABA, glutamate, acetylcholine and their precursors.

LDH assay for cell death—Lactate dehydrogenase (LDH) is an enzyme present in the cytosol of all human cells. Upon cytolysis, this enzyme is released into the media and can be quantified as an indicator of cell death. The Cytotoxicity Detection Kit (Roche) is a colorimetric LDH kit optimized for cell media. Percent cytotoxicity present in MPS is calculated by comparing absorbance values to non-diseased controls.

Immunocytochemistry—Neural markers will include glial fibrillary acidic protein (GFAP) for astrocytes, and CD11b or PU.1 for microglia. Disease-specific neurons are identified by any combination of tyrosine hydroxylase (TH) and PITX3 for DANs, and SMI32 and Islet (ISL1) for MNs. The Inventors will also include: (A) Early developmental markers nestin and Tuj1, and (B) late markers MAP2ab (neuronal), S100b (glial) and ChAT (MNs) or DA Transporter DAT (DANs). The Inventors will also confirm (C) BMEC identity through tight junction marker zona occludens 1 (ZO-1) and BMEC-specific marker glucose transporter 1 (GLUT-1). In the Inventors' previous work, the Inventors have determined optimum imaging techniques for both wide field and confocal microscopy. The Inventors have recently purchased a rapid scanning light sheet microscope able to very quickly scan through the entire chip and resolve neurons at high magnification. Implementation of this new imaging modality will continue as the Inventors_progress through each following experiment to generate digital records of every chip staining for comprehensive analysis.

RNAseq—Neural cultures are removed from the top channel and processed to analyze mRNA transcripts. To enhance read depth, chips are pooled at 3 chips per sample. RNAseq libraries were generated using the Illumina TruSeq Kit, sequenced on a Nextseq500 by 75 bp single reads, and aligned to the hg19 human genome, and quantified to reads per kilobase per million.

Proteomics—An emerging proteomic approach called data independent acquisition (DIA), also referred to as SWATH, is a two-step process involving (i) building a mass spectrometry (MS) peptide library that is composed of preselected high quality peptides representing the composition of cell populations within the CHIP and (ii) DIA MS data obtained from each digested individual CHIP sample that is analyzed on the MS instrument (6600 Triple TOF, Sciex) is compared to the peptide library. The advantage to DIA are: (i) maximizing breath of proteome coverage while minimizing sample quantity, increased accuracy and reduced experimental variability (reduced % CV to ~20%) due to both less number of analytic steps required for each sample and (ii) automation of mass spectrometry sample processing. If needed due to low abundance of target proteins, the Inventors can concentrate the effluent or combine samples harvested from multiple MPS devices. The Inventors will also use multiple reaction monitoring, a sensitive mass spectrometry method that only allows specific targeted peptides to be detected and quantified.

Example 5

Validate Biomarkers that are Reproducible Across 10 Individual iPSC Lines

The aforementioned studies establish phenotypic readouts in the MPS devices. A single control iPSC line, which is run at least 3 times through the protocol. Of interest is establishing what variance exists between different patients before this system can be used to detect disease-specific changes. Subsequently, 10 individual control lines allows for comparison of differences between patients (Table 3). Reducing potential sources biological of variability in later experiments, the Inventors will utilize a standard set of supportive tissues (BMECs, astrocytes, microglia) derived from a single control line. After 4 weeks, the Inventors will perform neuronal population and morphology analysis. Control lines reaching a minimum threshold of total spMNs or DANs in the chip are included, followed by application of the full set of phenotypic markers. Data is analyzed for how much variance there is in biomarker expression between human lines. Phenotypic assays whose outcomes show no significant difference between lines using ANOVA tests (P<0.05) are further evaluated.

Example 6

Further Adjustments

The Inventors expect the MPS devices with the combined cellular products to have enhanced neuronal activity and more mature neurons. Further adjustments can include refining either the ratios for each cell type, time of attachment or other parameters to establish conditions by which the cells can survive together within the MPS devices. Repeating this optimal protocol three times with one control line but bringing in the full range of biomarker read outs will allow determination of the reliability of the techniques. MPS chips and culture machines that house them are now manufactured with extremely low tolerance levels and with high quality control providing consistent performance from the devices, with the variability likely originating from biological sources.

Having determined the conditions and stable sets of potential biomarkers, deeper analysis of ALS and sPD lines is pursued. SMA iPSC lines are used as a positive control, as the Inventors know specific biomarkers such as lack of SMN protein and a cell death phenotype serving as a positive control.

Example 7

Figure 6:
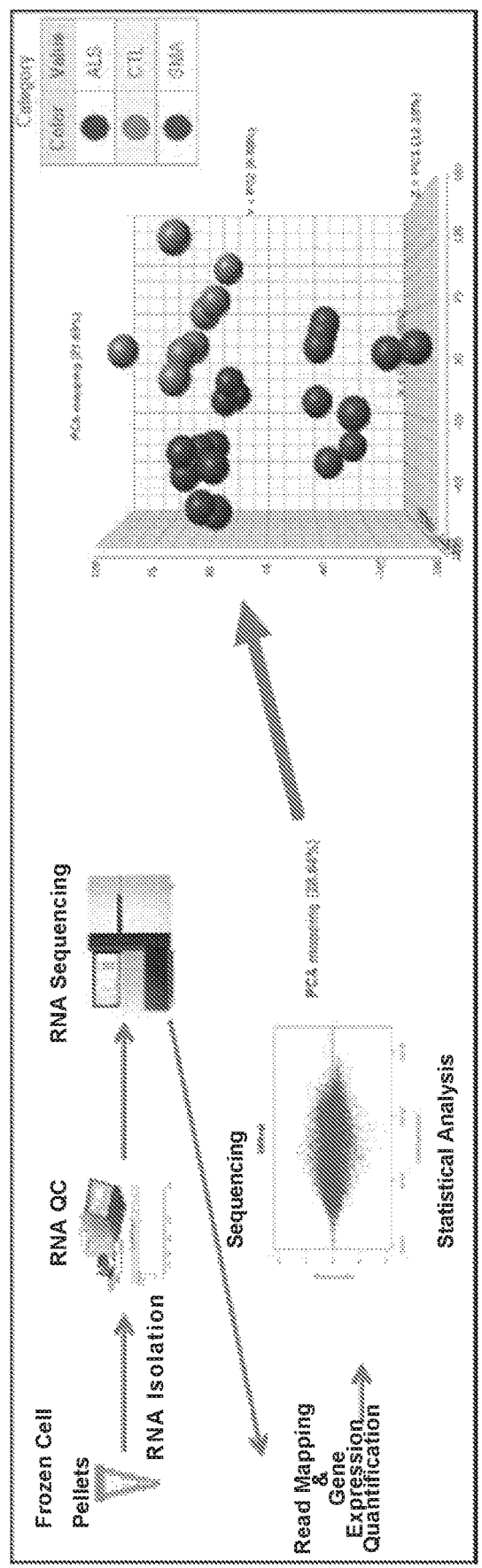
FIG. 6. Frozen pellets were prepared from standard culture plates and processed for RNASeq. Non-supervised clustering was performed that elicited clear separation between the disease and control lines assayed by principle component analysis (PCA).

Comparison of 4 sALS, 4 sPD, 4 Control, and 4 SMA Lines in the Validated spMN and DAN MPS Models to Identify Disease Biomarkers Earlier studies by the Inventors have shown that in 2-dimensional spMN cultures derived from iPSCs the Inventors can separate control, SMA and a genetic form of ALS based on RNAseq analysis and proteomics (FIG. 6). Interestingly, the Inventors found that TGF-β was a reliable biomarker that increased in ALS samples based on both RNAseq and proteomic data. Here, the improved physiological environment of the chip, and the inclusion of electrophysiology and metabolomics should increase the number of disease-related biomarkers further.

The experimental design is outlined in Table 4 with a description of the various assays is summarized in Table 2. In addition to these assays, the Inventors will include extra measures of oxidative and mitochondrial stress using caspase-3 staining and the Mitotracker dye. These have both been implicated in PD and ALS and the Inventors have already seen preliminary phenotypes in the Inventors' metabalomic assay (FIG. 7). In addition, the Inventors will interrogate disease-specific proteinopathies that represent clinical hallmarks of ALS and PD and that have been observed in vitro. Specifically, the Inventors will analyze the expression and localization of aggregated TDP-43 and synuclein proteins by confocal and light-sheet microscopy. All chips are assessed for biomarker expression at the four-week survival time. The Inventors will rank differences in biomarker expression between control/sALS and control/sPD and generate lists of those that are increased or reduced, in addition to any new biomarkers that are specific to the disease lines (and were not observed in any of the controls in SA1b).

Example 8

Test 20 sALS, sPD and Control Lines to Confirm Presence of Signatures that Hold Across Multiple Sporadic Lines While initial characterization of 4 lines will give an idea of disease-specific phenotypes, it is of interest to understand their reliability across a larger group for sALS and sPD as the Inventors' target diseases. These lines are available through the Inventors' current production of the Lothian control cohort (25 lines) and Answer ALS to produce the ALS cohort lines (currently in the process of making 1,000 iPSC lines). The Inventors will focus on rapid progressing patients to increase likelihood of severity in observed phenotypes. By the same token the Inventors will also create 20 sPD iPSC lines with a focus on early onset patients. The Inventors will compare the signatures across multiple disease lines with a direct focus on at least three major biomarkers.

Example 9

Metabolic Biomarkers

The Inventors may see some biomarkers specific to sALS and sPD predicted in the literature of familial disease models such as Caspase 3 increases, TDP43 mislocalization/aggregation or reduced DA neuron fiber length. Of greatest importance is that the biomarkers are reliable across patients and lines, and found to be associated with sporadic disease patient's lines. With the Lothian control cohort, this eliminates confounding biomarker signals in this group (i.e. control patients who would have developed ALS or PD). The Inventors believe that the most important biomarkers are the metabolomic in nature that lend themselves to scale-up for screening as described later.

Example 10

Role of Control Support Cells, Environmental Stress

As the Inventors have chosen to standardize the supportive cell types to limit potential variability and provide a system reflecting the physiological environment, the Inventors may find that disease phenotypes are protected using control support cells. If no phenotypes are seen, the Inventors will repeat experiments using support cells (BMECs, astrocytes, microglia) derived from ALS or PD patient lines and re-assess potential disease phenotypes.

Such outcomes would support notion of non-autonomous influence of support cells on diseased cells in ALS and PD pathology. While highly unlikely, a lack of significant difference between the ALS and/or PD lines and the control lines in any of the different analysis modalities, the Inventors will introduce an environmental stressor to the system. For the ALS lines this includes excitotoxicity with arsenite or phosphoinositide 3-kinase (PI3K) inhibitors shown to have selective effects on motor neurons and for PD lines it will be paraquat. This additional complexity demonstrates the unique benefits of an entirely iPSC-driven MPS model to dissect complex disease interactions in vitro.

Example 11

Detection of Functional Phenotypes in Motor or Dopamine Neurons

The use of calcium-florescent dyes has proven a valuable tool to determine neuronal function in the Inventors' MPS models. In addition to overall transient activity readouts (FIG. 3), increased interconnectivity of neurons in the mixed neural channel form neural networks that have dynamic population level activity signatures that mature over time (FIG. 8). As calcium dye administration is an assay that is conducted at endpoint, changes in neurophysiology over time in culture would require more chips for each experiment. Disease-related dynamics in network formation and response to drug treatment may yield new insights into pathogenesis.

Figure 9:
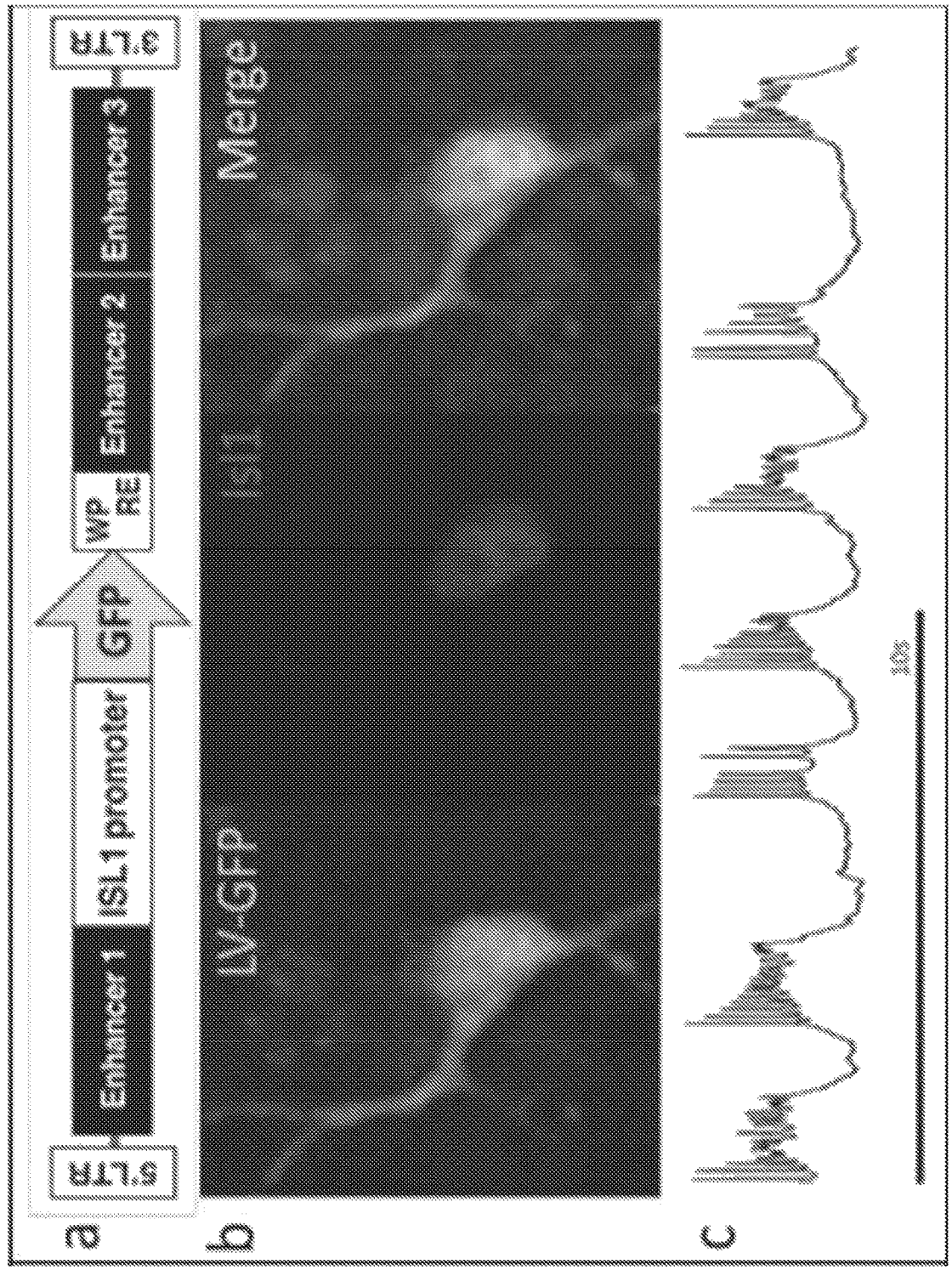
FIG. 9. (a) The Inventors have developed a novel MN-specific promoter construct to aid in live neuron function studies. (b) When packaged into a lenti-virus (LV), the islet 1 (isl1) promoter can be used to label cells via cytoplasmic GFP. (c) Neurons cultured on the MPS can be assayed for electrophysiological properties with whole-cell patch clamping by exposing the top channel for analysis. Highly complex, synchronous spontaneous bursts of activity were recorded in the MPS at 2 weeks in culture.

To allow for assay of the same chip over time, neural cultures can be infected with constructs containing cell type-specific promotors relevant to disease study, thereby creating a live readout that is specific to the cell type of interest (FIG. 9). The Inventors have previously developed a lentiviral construct containing a novel GFP reporter that is driven by an enhanced motor neuron (MN)-specific Islet 1 promoter, that permits high expression of GFP in Isl1-positive cells. The Inventors intend to utilize this novel promoter to drive GCAMP6 for a functional readout of spMNs over time and incorporate it into the biomarker read outs. With success of this system, the Inventors will also develop a DAN-specific Tyrosine hydroxylase promotor-driven GCAMP6 system that has been shown by other groups to be a successful dopaminergic cell marker.

The Inventors can also assess electrophysiological phenotypes at the individual cellular level by patch-electrophysiology (FIG. 9). This has allowed high-resolution analysis of neurons matured in the MPS. This can be further expanded by use of electrodes built into the MPS devices. The Inventors expect these specialized MEA MPS developments by year three and may use them in place of calcium imaging.

Example 12

MPS Based Drug Screens Using the NCATS Library

As described, biomarkers are detected with a combination of live electrophysiology (changes in firing patterns of neurons i.e. FIG. 9), cell death assays, neurotransmitter and metabolomic screens on the effluent, and q-PCR of highly discordant individual genes found from transcriptomic and proteomic analysis. Biomarkers include those found in the metabolome that would allow us to simply run a biomarker panel on all samples.

Alternatively, identification of a very robust electrophysiological phenotype, can be studied by a new, live MEA MPS system incorporating device electrodes, or through adaption of one of the described cell-specific reporters.

Figure 10:
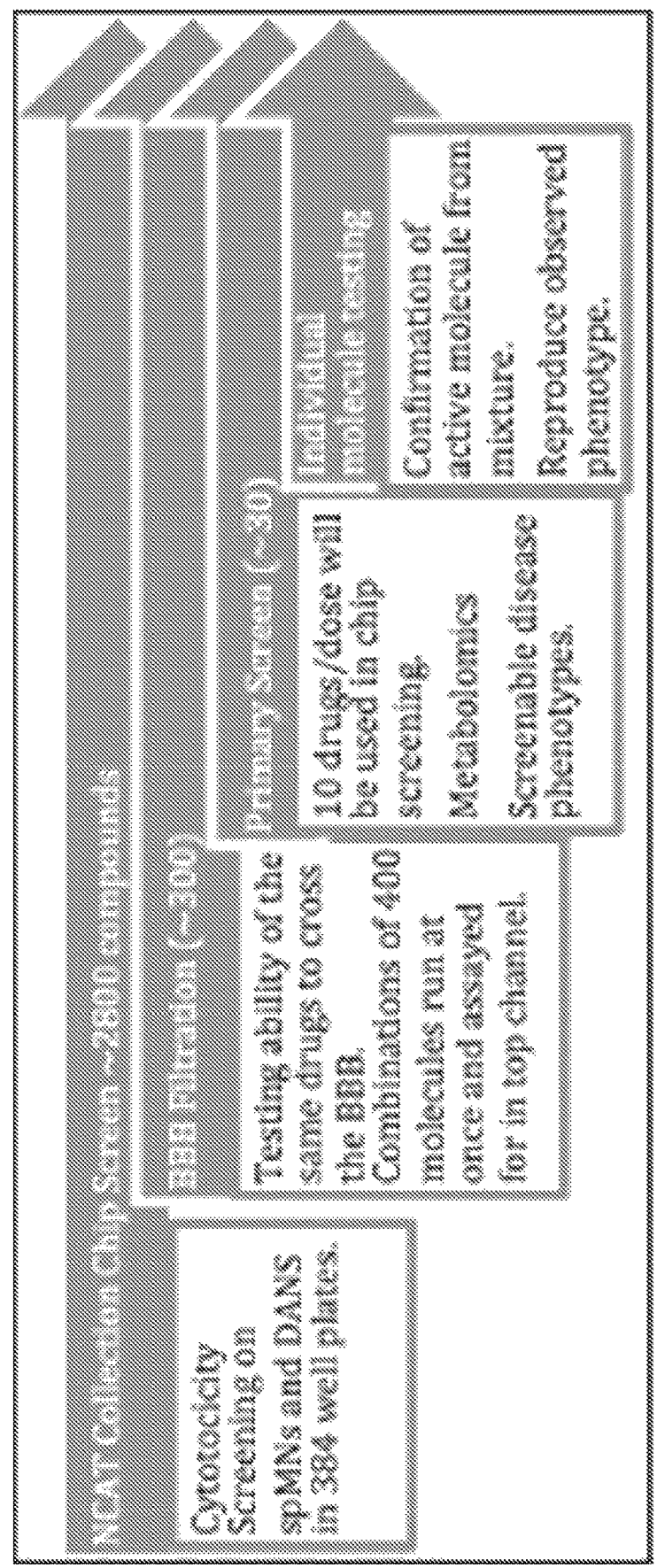
FIG. 10. Flow chart of drug screening outlines filtration steps and primary screening of NCATS compound library. Compounds will be tested for cytotoxicity with traditional methods. Compounds will then be tested for BBB permeability using the MPS system. Permeable compounds will be tested for disease phenotype modulation using a panel of screening assays listed in SA3c.

These approaches allow for use of the human iPSC-derived MPS systems at high-throughput drug discovery scale. As an example, Inventors have also leveraged the main advantage of MPS culture in trial designs by incorporating blood brain barrier properties (BBB) permeability as a primary filter to screen the NCATS Pharmaceutical Collection of 2816 compounds (FIG. 10). The Inventors will then take advantage of identified disease phenotypes including full metabolomic readouts of neural channel effluent. Finally, the Inventors aim to validate these candidates through high resolution assays only attainable in the MPS, including BBB permeability properties, live assays of electrophysiology and metabolite response, and end of assay readouts on the cells described above.

Example 13

An Annotated List of Clinically Valuable Biomarkers

The Inventors' top validated markers are compared to the known levels/activity in patient (both sporadic and genetic forms of ALS and PD) samples of blood, cerebral spinal fluid (CSF) and brain/spinal cord tissue based on an extensive mining of current literature. From these searches, the Inventors expect three possible outcomes: (i) The biomarker is already known to be altered in ALS or PD, which would be an indication that living neurons in the chip are recapitulating known disease pathology in patients. (ii) The biomarker has been assayed but was not shown to be associated with ALS or PD. This could indicate that it is only seen early in the disease pathogenesis (as the Inventors' cellular model uses "young" iPSCs) and may have been missed at clinical presentation or late-stages in patients. (iii) There is no known data on the biomarker determined from the MPS model: This possibility is likely a truly novel disease-specific trait that could then be tested in patients. In this case, the Inventors would attempt to develop an assay for selected biomarkers in biofluids from sALS and sPD patients. The Inventors' clinical co-PI's Drs. Baloh and Tagliati are well positioned to conduct clinical research centered on MPS novel biomarker validation. The Inventors expect the most translatable biomarkers to be in peripheral blood and CSF. As all three possibilities have clear clinical significance, biomarkers are ranked based on both promising translational data and feasibility of biomarker detection at scale both on chip and in patient biofluids. The Inventors will then use this short list to design a novel drug discovery platform using these new biomarkers in the experiments described below.

Example 14

Small Molecules that Pass Through the BBB into the Neural Side of the APS

Figure 11:
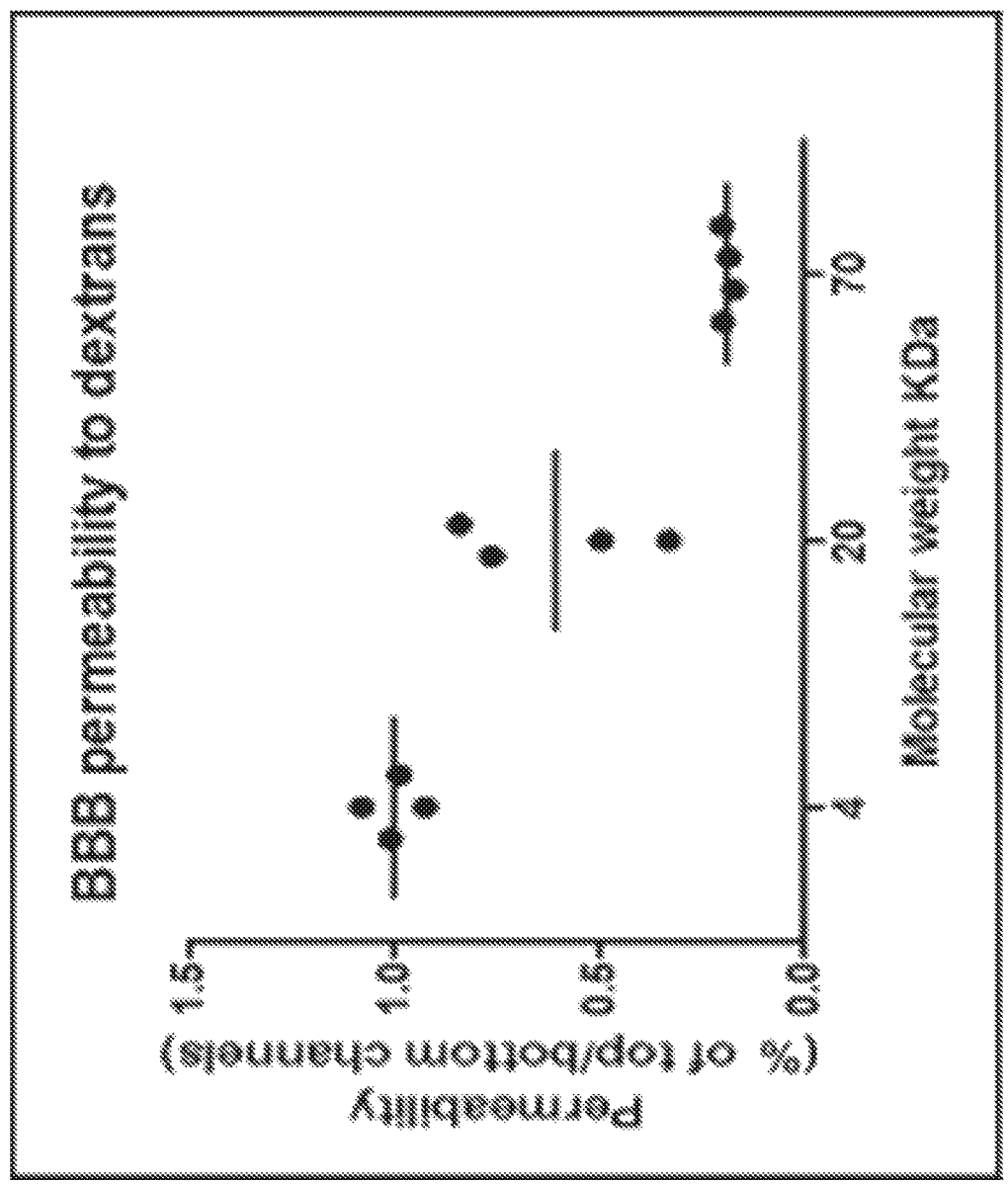
FIG. 11. The blood brain barrier of the MPS models is a critical asset for drug development. Paracellular permeability assessment of different sized molecules pass through the BMEC barrier from the bottom to the top channel with different efficiencies. Adequate barrier function has been recorded at 3 weeks in chip. Y-axis is plotted by percent of bottom concentration detected after 18 hours.

The Inventors will first test all drug candidates for BMEC, MN and DAN toxicity so as to not confound any barrier properties or functional disease phenotype effects of an active molecule in the primary mixture. To save resources, the Inventors will test control MN and DAN cultures on a standard 384-well format drug screening platform. Non-cytotoxic compounds are identified for subsequent combination screening in the MPS. Based on experience, the Inventors expect a rate of 2-5% cytotoxicity. The Inventors will then seek to filter the candidate library by the ability of candidate molecules to cross from the blood channel, through the BMEC layer, and into the neural compartment. In extensive unpublished studies, the Inventors have shown that this system mimics the BBB with respect to know drugs that do and don't cross the barrier (FIG. 11). In addition, the unique culture device that houses the MPS chips has an input reservoir that can be used to load drugs into the blood side and collect drugs from the brain side. The Inventors expect these compounds to have the highest likelihood of rapid translation to the clinic because of their BBB permeability. The Inventors will determine this permeability by first flowing a series of 100 compound mixtures through the bottom channel and probing for the same molecules on effluent from the neural compartment by mass spectrometry. This are repeated 29 times until all 2,816 drugs have been tested for permeability. Based on poor BBB penetration observed in vivo, the Inventors expect only a subset (~20%) of the NCAT's collection will be detected within a threshold higher than dextran, which is included as a negative control. These filtered compounds will then be used in the Inventors' primary screening.

Example 15

Conduct Primary Screen to Identify Novel Biomarker Modulating Compounds

Positive candidate mixtures will then be separated into individual compounds and rerun in a new set of chips to determine individual candidates to be characterized in the final year of this grant. Final candidates are validated using the full range of biomarkers to determine how well the phenotypic changes are reversed by each drug, in addition to metabolomic changes. The Inventors will conduct dose response experiments to also determine optimum concentration based on modified phenotypes. The Inventors may also find drugs that exacerbate certain disease phenotypes that may elucidate new therapeutic target pathways. As these drugs are FDA approved, this should lead to a unique set of new drugs that can be rapidly moved into clinical trials for sALS and sPD.

Example 16

Co-Cultured iBECs and Human Neural Cells Show Cellular Interactions and BBB Functionality While astrocytes and iBMECs can remain in their respective channels, astrocytes processes protruded through the pores to form direct cell-to-cell contact with the iBMECs, mimicking the astrocyte-end-feet observed in vivo. Furthermore, co-culture with human pericytes and astrocytes significantly decreased the blood-to-brain leakage of fluorescent dextran-FITC (3 kDa) compared to iBMECs cultured alone on the organ-chip, indicating that in addition to laminar flow, primary human astrocytes and pericytes can further promote functional BBB maturation on the organ-chip. Taken together, these results demonstrate organ-level structures resembling the interface of the NVU forming the BBB. Perfusing the blood compartment overnight with 10 or 100 ng/ml of TNFα caused a change in astrocyte morphology and a decrease in end-feet-like structures covering the vascular surface, compared to the control condition. Interestingly, reduction in the vascular end-feet coverage was followed by an increase in blood-to-brain leakage of dextran, indicating that vascular stimulation has a significant impact on barrier functions and that a functional link between the brain and the blood compartments was recapitulated.

Example 17

Astrocyte End-Feet Coverage Analysis

In order to quantify the percentage of vascular surface covered with astrocyte protrusions (end-feet like structures), the vascular surface of the are washed in DMEM (without FBS) and stained with the fluorescently labeled wheat germ agglutinin (WGA-647 Invitrogen), a leptin able to bind to the vascular glycocalyx (DOI: 10.1002jemt.22602). After 15 minutes at room temperature, chips were rinsed twice with fresh DMEM, fixed in 2% PFA for 20 minutes at room temperature and stained for the astrocyte marker GFAP (Abcam). Following incubation with the anti-mouse secondary antibody (Invitrogen, Alexa Fluor 488) and HOECHS (Abcam) chips were washed in PBS and imaged via confocal microscopy (Zeiss LSM850).

The area underneath the porous membrane was localized using the WGA-647 signal (that stained the whole endothelial surface) and the nuclear fluorescence signal (HOECHST) of endothelial cells. Then, five random areas of each chip were imaged using the GFAP fluorescent (488) signal using a 10× objective (Zeiss). ImageJ software was used to subtract background and then convert the digital signal detected in the GFAP channel into a binary image. Finally, percentage of signal coverage was computed from the binary image as the ratio of bright pixels to the total number of pixels in the image. Image processing and quantification was performed with an automatic macro compiled in ImageJ in order to ensure unbiased signal measurements. Numerical values were collected and statistically analyzed using Graphpad Prism V7.

Example 18

Findings

The physiological, molecular and cellular changes that underlie amyotrophic lateral sclerosis (ALS) and Parkinson's disease (PD) are complex. The Inventors have leveraged Cedars-Sinai's Induced Pluripotent Stem Cell (iPSC) Core to generate large cohorts of ALS and PD lines. Highly physiological models have been developed that combine co-culture of disease relevant tissues to study ALS (ALS-Chip) and Parkinson's Disease (PD-Chip). In addition, this microphysiological platform contains a vascular channel that is brain-specific and enables the study of blood brain barrier (BBB) properties in a human diseased system. To understand disease-specific pathophysiology, a comprehensive array of genomic, metabolomic, and electrophysiological assays have been developed and will be used to generate novel biomarkers in both systems. The primary outcome of this project is the establishment of reproducible disease specific phenotypes of both sporadic ALS and PD that will then be used as biomarkers to screen for novel phenotype-reducing drugs either to the brain side or the blood side, which would simulate the ability of the compound to cross the blood brain barrier. In the Inventors' second year, the Inventors have established cohorts of early onset sporadic (EOS) PD and ALS patient lines, and have ongoing studies to determine robust biomarkers using midbrain and spinal cord chip models. In the Inventors' first full PD trial, the Inventors utilized 5 EOSPD lines and compared them to 5 controls from the Inventors' "super control" Lothian cohort. The Inventors have determined initial disease-specific signatures in the PD patient lines in both live cell imaging, as well as metabolomic signatures. The PD-Chip paradigm has also been adapted to use as a platform for studying effects of opiates on human dopaminergic neurons, and results from preliminary studies on response to morphine and other opiate agonists will also be presented.

Example 19

Figure 45:
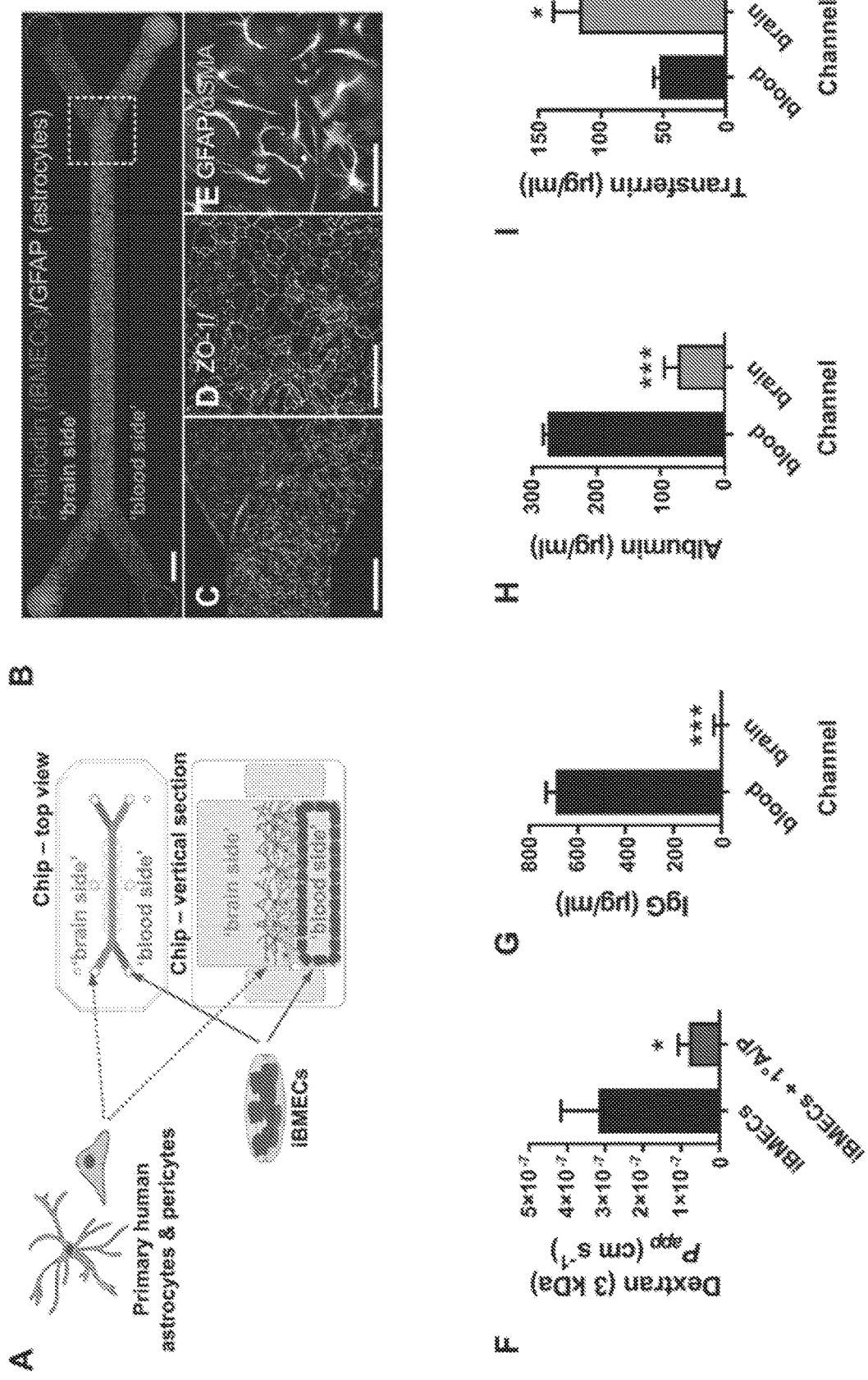
FIG. 45. Personalized iPSC-based BBB-Chip detects inter-individual variability. A) Schematic of seeding strategy. iPSCs are differentiated into EZ-spheres (early neural progenitors) in suspension. EZ-spheres are then dissociated and seeded on the 'brain side' where they further differentiate into mixed neural cultures. Isogenic iPSCs are differentiated into iBMECs and seeded on the 'blood side' as described above. B) Immunocytochemistry on the CS83iCTR iPSC-based BBB-Chip seven days post-seeding demonstrates that EZ-sphere-derived neural cultures populating the brain compartment express Nestin+ neural progenitors (red); GFAP+(red) and S10013+(green) astrocytes; and the neuronal markers heavy chain neurofilament (hNF, red), MAP2ab (green), and 131I-Tubulin (red), as well as the synaptic marker synaptophysin (SYP, green). Scale bar 200 µm. C) At eight days post-seeding, calcium imaging revealed that neural cultures exhibit spontaneous neuronal activity on the Organ-Chip that is inhibited by tetrodotoxin (TTX). D) Blood-to-brain permeability of dextran-FITC (3 kDa) was measured on Organ-Chips seeded with iBMECs alone (black bar), iBMECs with primary human astrocytes and pericytes (red bar) or iBMECs with iPSC-derived neural cells (iNeural, blue bar). One-way ANOVA with Dunnett's multiple comparisons test (*p<0.05). E) TEER measurements reach 1500 Ω×cm$^2$ two days post-seeding and remain above 1000 Ω×cm$^2$ for 5 days. F) Permeability of dextran molecules of 4, 20 or 70 kDa compared in BBB-Chips derived from healthy control iPSCs (CS617iCTR, CS0172iCTR, CS188iCTR) or a Huntington disease patient iPSCs (CS81iHD). Two-way ANOVA with Tukey's multiple comparison test, *p<0.05. G) The permeability of dextran molecules across healthy control iPSC-derived BBB-Chips correlated ($R^2$=0.96) with previously reported in vivo rodent brain uptake (Pe, cm s$^{-1}$). H) Blood-to-brain T3 permeability compared in BBB-Chips derived from healthy donors (CS617iCTR, CS172iCTR, CS188iCTR, CS03iCTR), MCT8-deficient patient (CS01iMCT8), an isogenic line where a nonsense mutation was introduced into the CS03iCTR line (CS03iCTR$^{mut}$), and an isogenic line where a point mutation was corrected in the CS01iMCT8 line (CS0iMCT8). Nested t-test between MCT8 mutants and control lines, *p<0.05. I) Dextran-FITC and the fluorescent glucose analog 2-NBDG or Retigabine, Levetiracetam, and Colchicine were spiked simultaneously to the 'blood channel' (10 µg/ml each) and their permeability and concentrations were evaluated on the 'brain side' by means of fluorescence or liquid chromatography tandem mass spectrometry (LC-MS/MS). One-way ANOVA with Tukey's multiple comparison test, *p<0.05, ***p<0.001, n=3-4 chips per drug per cell line. Data for samples run on LC-MS/MS were averaged from 3 separate injections per sample.
Figure 45:
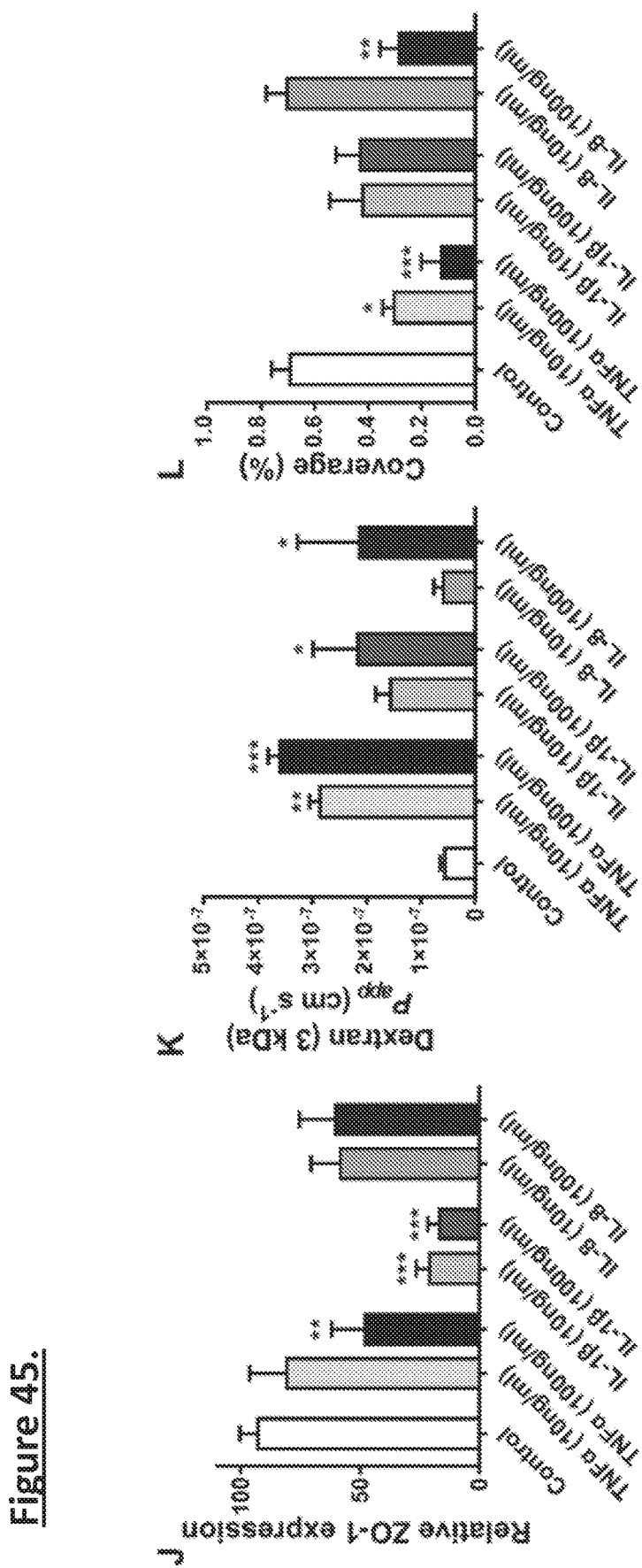

Inter-Individual Variability Across BBB-Chips can Detect BBB Alterations in Diseased Patients Demonstrating organ-specific disease modeling is important to validating the iPSC-based BBB-Chip as a relevant system for personalized medicine. The Inventors recently reported an iPSC-based model of Huntington Disease (HD) in which HD-iBMECs showed altered barrier functions. In order to assess the possibility of using a personalized BBB-Chip as a predictor for patient-specific brain penetrability of candidate molecules, the Inventors examined the permeabilities of fluorescently-labelled dextrans of varying molecular weights across iPSC-based BBB-Chips derived from three healthy donors (CS617iCTR, CS172iCTR and CS188iCTR) and a HD patient with 71 CAG repeats within the HUNTINGTIN gene (CS81iHD). Notably, there were no significant variations observed across healthy individuals, yet there was a significant increase in dextran-FITC molecule permeability in the HD-BBB-Chip (FIG. 45F). Furthermore, the permeability of the dextran molecules across BBB-Chips from healthy controls correlated with previously reported in vivo rodent brain uptake (Yuan et al., 2009) ($R^2$=0.96), demonstrating that the iPSC-based BBB-Chip formed and maintained a barrier that could selectively separate molecules based on size (FIG. 45G). The Inventors have also recently reported an iPSC-based model for monocarboxylate transporter 8 (MCT8)-deficiency, a severe form of psychomotor retardation, and showed that thyroid hormone (triiodothyronine, T3) transport across iBMECs requires functional MCT8. In order to further assess organ-specific disease modeling, the Inventors generated an iPSC-based BBB-Chip for MCT8-deficiency, which used the above healthy control lines as well as the following published iPSC lines: (i) control line CS03iCTR; (ii) CRISPR/Cas9-mediated MCT8 mutation CS03iCTR$^{mut}$; (iii) patient line CS01iMCT8; (iv) MCT8 mutation line with corrected mutation using CRISPR/Cas9-mediated homologous recombination CS01MCT8$^{cor}$. Liquid chromatography tandem mass spectrometry (LC-MS/MS) showed that while T3 transport was consistent across healthy control BBB-Chips, MCT8-deficient-BBB-Chips showed significantly lower permeability (FIG. 45H), confirming the necessity of MCT8 for the blood-to-brain transport of T3 across the BBB. Altogether, these results suggest that patient-specific iPSC-based BBB-Chips may be used to predict inter-patient variabilities in BBB functions.

The Inventors next tested whether the iPSC-based BBB-Chip could be used to predict the relative permeability of additional molecules, including the fluorescent glucose analogue 2NDBG, the marketed drug colchicine (gout treatment, moderate permeability), and the anti-epileptic drugs Levetiracetam and Retigabine, which can efficiently penetrate the BBB. These molecules were spiked simultaneously into the 'blood side' and their concentration on the 'brain side' was evaluated using fluorescence or LC-MS/MS (FIG. 45I and FIG. 47A). The diffusion of these molecules across the iPSC-based BBB-Chip demonstrated the expected differences in permeability, suggesting that this model can predict human CNS drug penetrability.

Example 20

Figure 46:
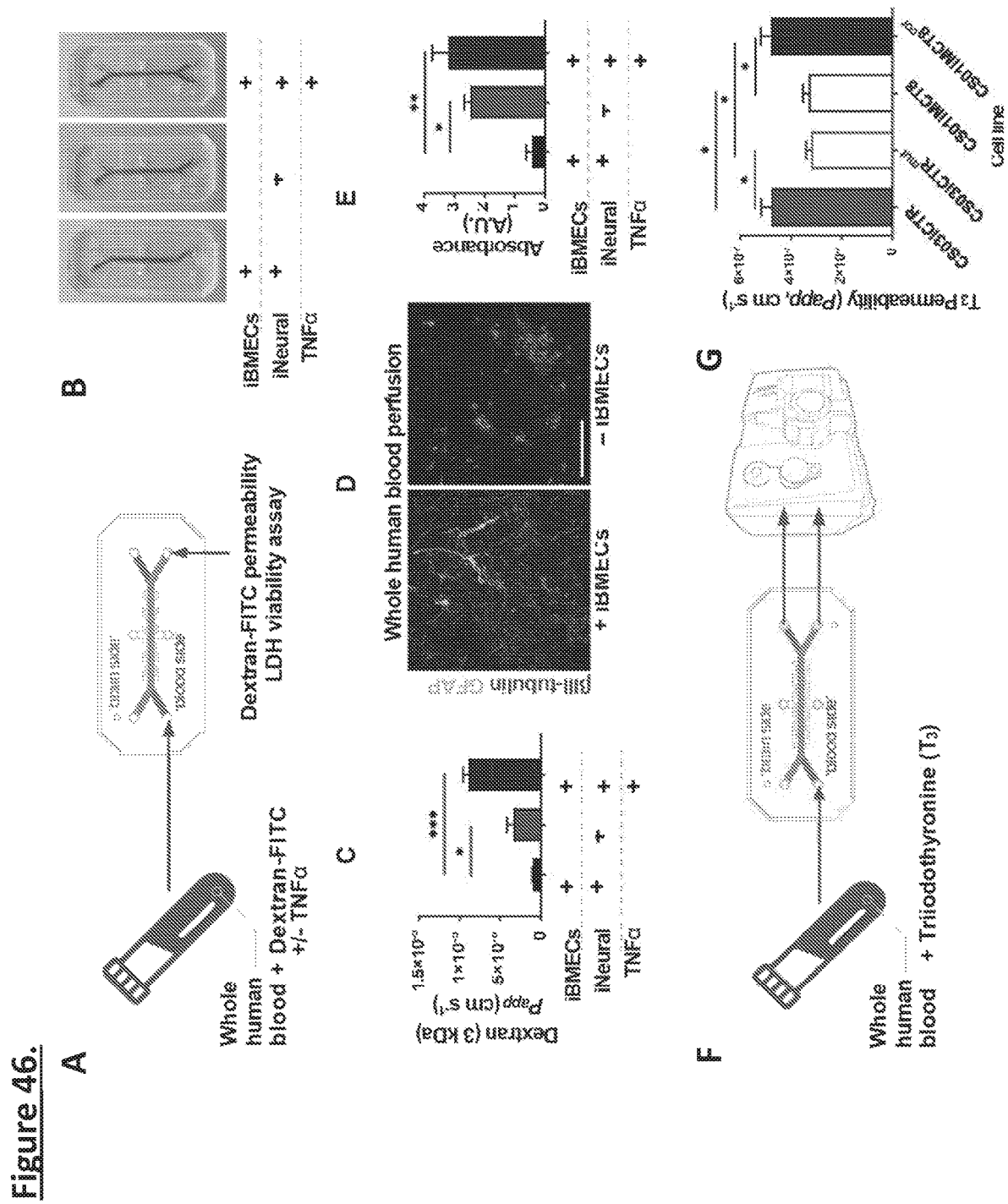
FIG. 46. Whole human blood filtration with the iPSC-based BBB-Chip can assess neurocytotoxicity and enhance disease modeling. A) Schematic of perfusion of whole human blood through the iPSC-based BBB-Chip. B) Whole human blood was perfused through the 'blood side' at 3600 µl/hr (equivalent to 5 dyn/cm$^2$). iBMECs restrict whole blood to the 'blood channel'. When neural cells are cultured alone or when iBMECs are treated with TNFα (10 ng/ml), whole human blood can diffuse to the 'brain side' (highlighted by the green arrows). C) Measuring blood-to-brain permeability of fluorescent dextran-FITC (3 kDa) following overnight perfusion of whole human blood showed low diffusion levels when neural cells were cultured with iBMECs (white bar), and a significant increase in permeability when iPSC-derived neural cells were cultured alone (grey bar) or following TNFα treatment (10 ng/ml, black bar). One-way ANOVA, *p<0.05, *p<0.0001. D) Immunocytochemistry of βIII-Tubulin+ neurons (red) and GFAP+ astrocytes (green) showed that neural cells are protected by iBMECs, but are reduced when cultured alone. Scale bar 200 µm. E) Assessing neural toxicity by quantifying LDH confirmed that iBMECs provide a functional barrier that can protect the 'brain side' from blood-induced cytotoxicity (white bar). In contrast, Organ-Chips without iBMECs (grey bar) or with TNFα treatment (black bar) led to vascular leakage and a significant increase in LDH release. One-way ANOVA with Dunnett's multiple comparisons test, p<0.01. F) Experimental design for MCT8-deficiency disease model. G) Measuring blood-to-brain T3 (100 nM) permeability across iPSC-based BBB-Chip containing control lines (filled bars) and MCT8-deficient lines (empty bars) showed that iPSC-based BBB-Chips with the MCT8 mutation have significantly reduced transport compared to BBB-Chips with no mutation. One-way ANOVA with Tukey's multiple comparisons test, *p<0.05. Color coding represents CRISPR/Cas9-edited isogenic iPSC lines.

Whole Human Blood Perfused Through BBB-Chip is Restricted to 'Blood Side', which Protects Against Blood-Induced Toxicity and Enhances Disease Modeling In most culture systems, neural cells are maintained in medium containing nutrients and growth factors, which does not account for vascular blood flow. However, exposing neural cells to unfiltered blood may lead to cytotoxicity, as observed in brain hemorrhage. Thus, a functional BBB is required to filter the blood in order to safely provide supportive nutrients and growth factors to neural cells. Whole human blood treated with the anti-coagulant sodium citrate was perfused at a physiologically relevant shear rate (3,600 µl/hr, equivalent to 5 dyn/cm$^2$) through the 'blood side', while the brain compartment with iPSC-derived neural cells was perfused with neural media (FIG. 46A). Measuring dextran-FITC (3 kDa) permeability during blood perfusion showed that iBMECs were able to maintain a functional barrier that confined blood to the 'blood side' (FIG. 46B, C). In contrast, BBB-Chips with no iBMECs or with iBMECs treated with TNFα did not have a functional barrier, resulting in blood leakage into the 'brain side' (FIG. 46B, C). Immunocytochemistry analysis and a lactate dehydrogenase (LDH) viability assay showed that neural cells with the iPSC-based BBB-Chip did not exhibit blood-induced toxicity, while neural cultures without iBMECs or treated with TNF-α exhibited significant toxicity (FIG. 46D, E). These results demonstrate that iBMECs in the iPSC-based BBB-Chip protect neural cells on the 'brain side' from blood-induced cytotoxicity, thereby recapitulating one of the key in vivo functions of the BBB. The incorporation of whole human blood into the iPSC-based BBB-Chip introduces another important in vivo BBB interface to this platform.

In the blood, over 90% of T3 is bound to proteins that act as carriers and only a small portion remains unbound and active. Thus, to test the MCT8-deficiency model under these physiological conditions, whole human blood spiked with T3 was perfused through the 'blood side' and neural media without T3 was perfused through the 'brain side' (FIG. 46F). T3 permeability across MCT8-deficient iPSC-based BBB-Chips was significantly lower compared with iPSC-based BBB-Chips from healthy control lines (FIG. 46G). These results demonstrate that blood-carried T3 transport across the BBB is MCT8-dependent. Notably, the overall permeability of T3 across healthy control iPSC-based BBB-Chips was ~5-fold lower with whole blood perfusate compared to media (FIG. 45H), suggesting that measuring transport in the context of whole blood recapitulated some aspects of the physiological BBB. These experiments demonstrate that whole blood can be used in conjunction with the BBB-Chip platform to further establish the role of the BBB in genetic-based neurological disease.

Example 21

Alzheimer's Disease on Chip

Frontotemporal dementia (FTD) is a clinical syndrome that is particularly common in patients with dementia that are under age 65. It is the third most common across all age groups after Alzheimer's Disease and dementia with Lewy Bodies. Patients display progressive deficits in behavior, executive function and language, and FTD can mimic a variety of psychiatric disorders because of the prominent behavioral component. The pathology of FTD is referred to as frontotemporal lobar degeneration (FTLD), characterized by neuronal loss, gliosis, and microvacuolar changes of frontal lobes, anterior temporal lobes, anterior cingulate cortex, and insular cortex. These regions have specialized neurons in layer 5 of the cortex (Von Economo and fork neurons), which are hypothesized to play a role in the integration of cortical and subcortical networks and degenerate very early in behavioral-variant frontotemporal dementia. Aggregates of the RNA binding protein TDP-43 are found in about 50% of FTLD (referred to as FTLD-TDP), with the remaining cases either having aggregated MAPT (FTLD-tau) or FUS (FTLD-FUS). A family history of dementia is reported in up to 40% of subjects, supporting a strong genetic component. Common genetic mutations that underly FTLD-TDP include hexanucleotide repeat expansions in C9orf72, loss of function mutations in the GRN and TBKJ genes, and missense mutations in TARDBP (which encodes TDP-43 itself), VCP, and CHMP2B. In addition to being the most common pathologic and genetic variant of FTD, it shows significant overlap with the related neurodegenerative syndrome amyotrophic lateral sclerosis (ALS), with shared genetic drivers and pathology. Additionally, there is strong evidence for a non-cell autonomous and even non-CNS autonomous pathogenesis of FTLD-TDP, making it ideally suited for the multicellular 3D forebrain-on-chip modeling proposed here.

Of interest is modeling the most common genetic forms of FTLD-TDP from C9orf72 and GRN mutations. Each of these genes is expressed highly in myeloid cells including microglia. Interestingly, there is a connection between FTLD-TDP and systemic inflammation, and patients with the disease have an increased incidence of autoimmune diseases. Thus, it has been postulated that FTD related mutations may have a significant impact on myeloid cell function in the brain and peripheral immune system. However, iPSC modeling to date has focused entirely on neuronal cell autonomous phenotypes. The unique organ-on-chip modeling with cortical and endothelial cells to create a BBB allows for the innovative examination of how serum from FTLD-TDP patients may affect neuronal phenotypes in this human forebrain model. Furthermore, in several of the common genetic forms of FTLD-TDP there are therapeutic strategies being considered for clinical use, including antisense oligonucleotides (ASOs) to knockdown C9orf72 repeat expansion containing transcripts, and gene therapy and/or drugs to augment expression of GRN. However, as no biomarkers are available for FTLD-TDP and clinical progression is difficult to measure, the development of tools for validating therapeutic interventions prior to entering clinical trial remain a critical need. Therefore, proof of concept therapeutic interventions such as ASOs and gene therapy will be used as tools to validate biomarkers identified in the 3D model system of FTLD-TDP. Finally, the Inventors' access to clinical measures, biospecimens, and autopsy material provides a unique opportunity to cross validate the Inventors' findings in the forebrain microphysiological system (fMPS) with clinical measures in humans.

If successful, the Inventors are uniquely positioned to have a significant impact to drive further insight into the pathophysiology related to progranulin and TDP-43 proteinopathies in a format that will advance the development of diagnostics and interventions. iPSC-derived neurons have been extremely successful in modeling certain neurological diseases, as the Inventors have shown previously for spinal muscular atrophy (SMA), Huntington's disease, C9orf72 related ALS, and MCT8 deficiency. The Inventors recently reported that incorporation of iPSC-derived brain microvascular endothelial cells (BMECs) enhances neuronal maturation in a 3D organ-on-chip model, and the Inventors have extensive preliminary data on cortical neuron and microglial differentiation from iPSCs in 2D culture, which is ongoing work as the Inventors are part of the current NCATS chip consortium. The Inventors also have preliminary data shown below and a publication in review that validates the functional capacity of the Inventors' BMEC protocol to form a BBB when co-cultured with non-specific neurons on the MPS chip. Finally, through the UCSF Memory and Aging Center, the Inventors have one of the world's largest and most well characterized collections of FTLD-TDP patients, with correlated autopsy material, biofluids, and clinical measures.

In this aspect, the claimed invention includes (i) the entirely human, patient-specific model of forebrain tissue through combination of cortical neurons, astrocytes, microglia and brain microvascular endothelial cells (BMECs) in the highly scalable and commercially available MPS device from Emulate Inc; (ii) the comprehensive nonbiased approach to biomarker discovery applying electrophysiology, metabolomics (including neurotransmitter levels), and single cell transcriptomics to capitalize on the MPS ability to flow reagents over the cells or through the BBB and collect information in real time biological screens through the cartridge system; (iii) development of iPSC lines with paired isogenic controls through CRISPR/Cas9 engineering from the most common variants of FTLD-TDP; (iv) the combination of an active blood brain barrier (BBB) with the forebrain tissue including microglial cells, allowing the examination of peripheral serum factors on neuronal and glial function in vitro. Finally, (v) the Inventors have the unprecedented opportunity to cross validate FTLD-TDP fMPS findings with comprehensive clinical, imaging and biomarker data as well as post-mortem pathology and cortical single nuclei RNA-seq from the same individuals. This approach has the potential to lead to "patient on chip" precision medicine and disrupt the way ADRDs are currently treated.

Example 22

The Emulate Platform with iPSC-Derived Tissue

Emulate's MPS technology includes leading models of the lung alveolus and small airway, intestine, liver, kidney, blood-brain barrier (BBB) and other organs. The Inventors have successfully applied the MPS platform for modeling of the BBB using iPSC-derived brain microvascular endothelial cells and non-specific mixed neuronal cultures (FIG. 50) in addition to establishing robust brain-on-chip models. The Inventor use a patient's peripheral blood or fibroblast cells are directly reprogrammed using non-integrating techniques that allow for transient ectopic expression of reprogramming factors. Over a few passages, iPSC colonies shed epigenetic marks and remain a stable source of pluripotent cells that carry the genetic makeup of the donor patient. These iPSCs can be expanded and cryogenically stored for subsequent disease modeling research of the various tissue types of interest as outlined below.

Figure 47:
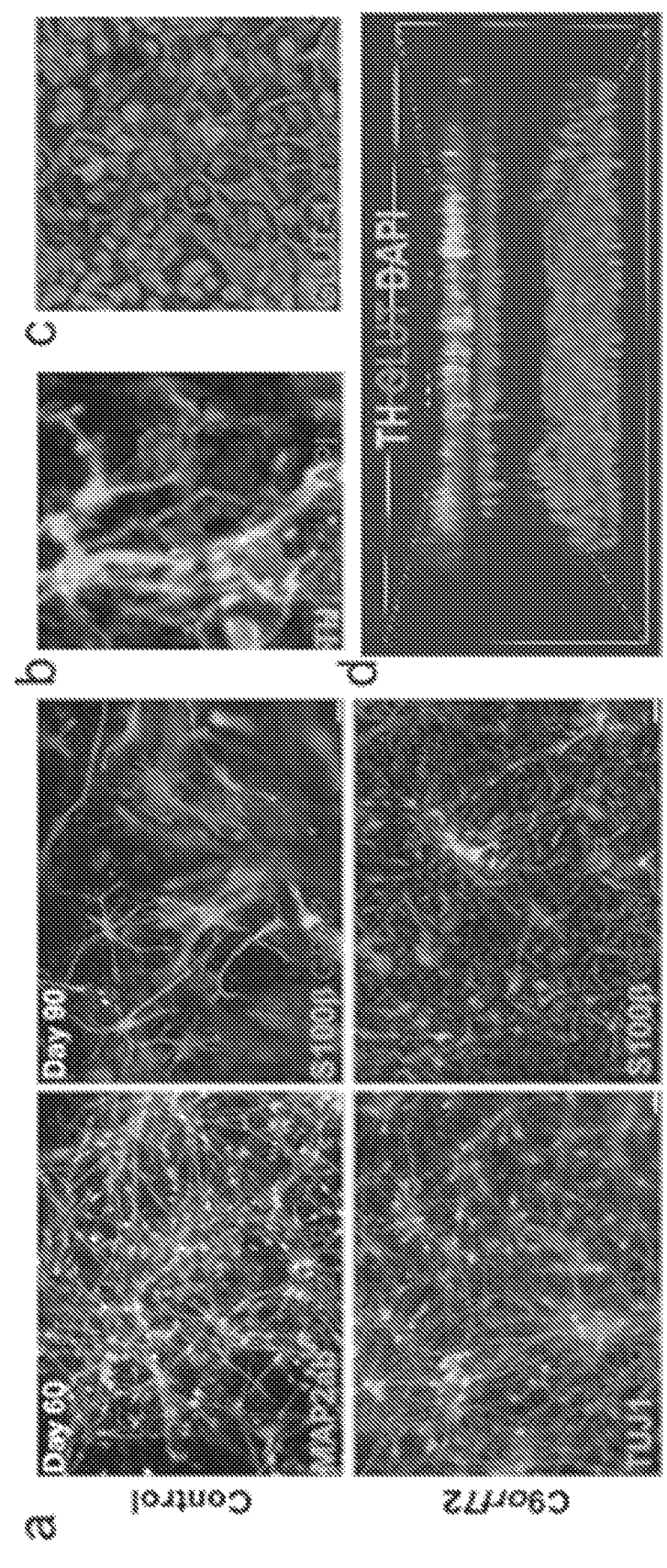
FIG. 47. iPSC-derived cell types for Forebrain MPS. (a) Control and C9orf72 CNs both express BCL11B at 60 days and astrocyte proteins at 90 days. (b) Microglia (red) co-cultured with dopaminergic neurons (TH; green). (c) Brain microvascular endothelial cells (BMECs). (d) Cross-section image of MPS after 3 weeks of co-culture with BMECs in bottom compartment and neuronal cells (green) in the top.
Figure 48:
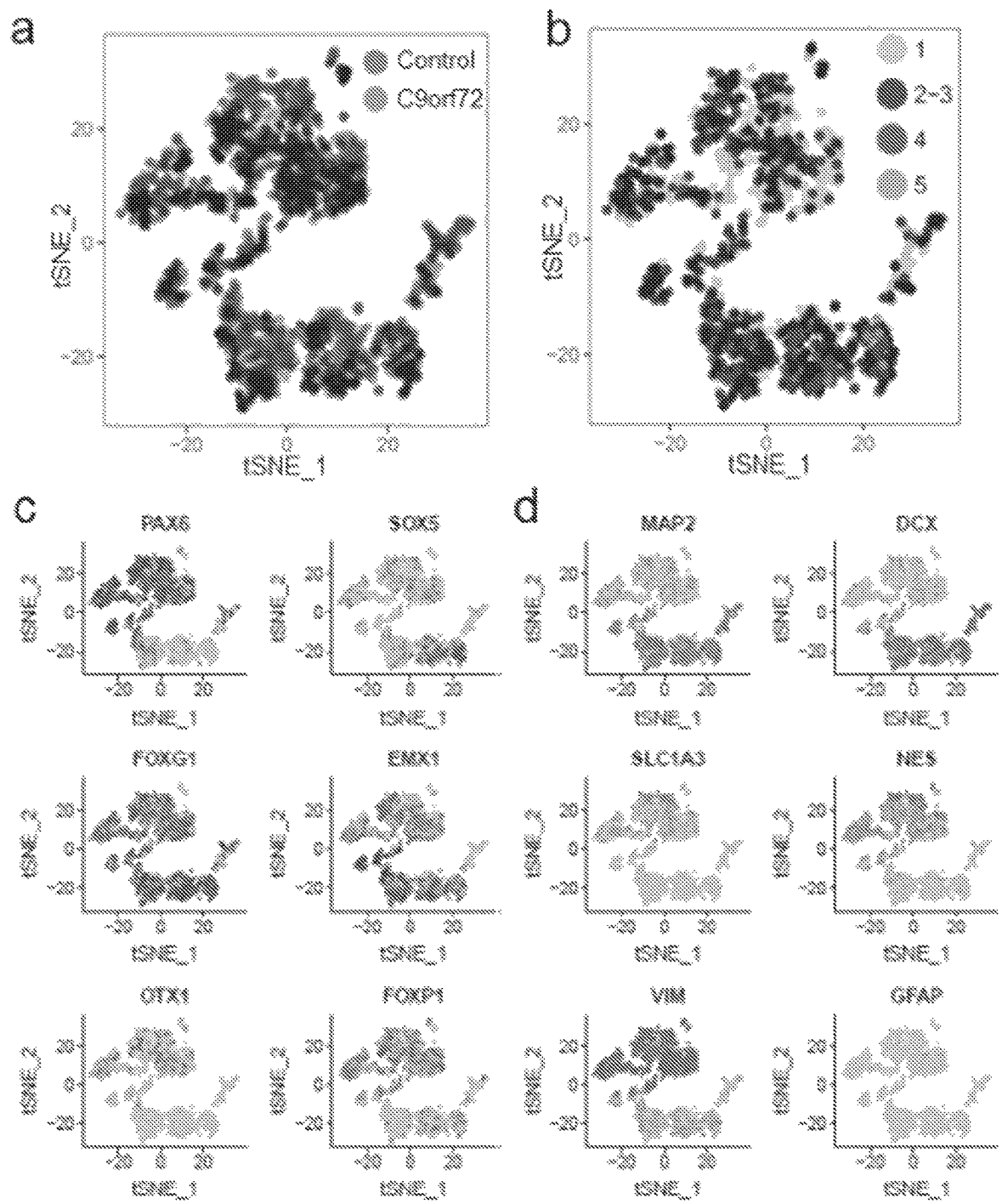
FIG. 48. At Day 50, CNs express forebrain and VEN-related transcriptomes. (a) Unbiased clusters of CTR and C9or172 CNs. (b) Cells that express 1, or co-express 2 to 5 genes associated with Von Economo neurons (VENs). (c) CNs express typical forebrain-specific transcripts. (d) CN culture is comprised of mature neurons (top), neural progenitors (middle) and some immature glia (bottom panels).
Figure 49:
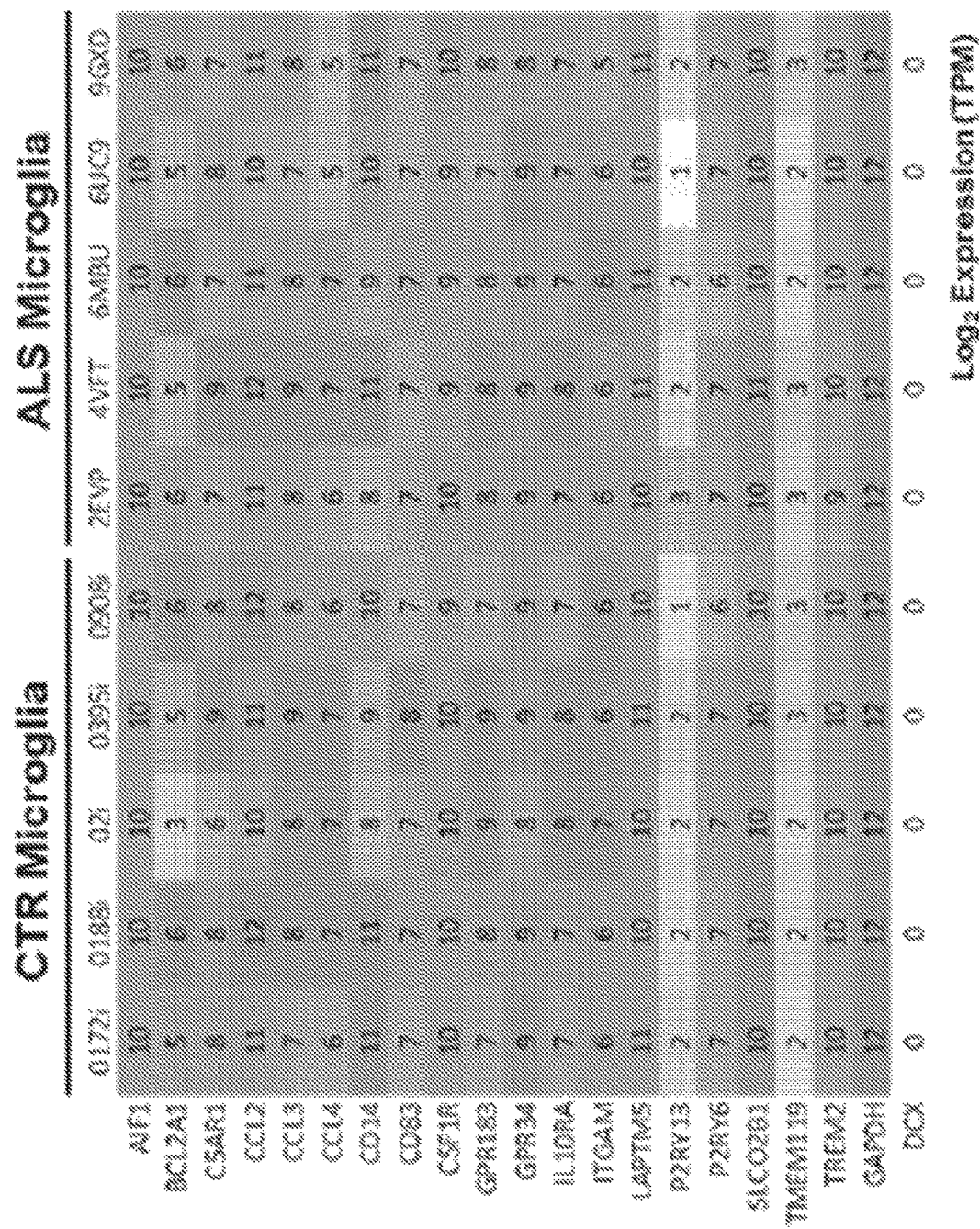
FIG. 49. iPSC-derived MG are highly reproducible. In 2D, 5 control (CTR) and 5 ALS (C9or172) lines express MG-related transcripts. Both control and disease lines consistently generate microglia.

Producing forebrain-specific neurons: As part of a NeuroLINCS initiative, Cedars-Sinai adapted a cortical forebrain protocol for production of large-scale, cortical neuron (CN) cultures that are cryopreserved and distributed for robotic imaging, single-cell RNA sequencing (scRNA), proteomic, mRNA transcriptomic, and epigenomic analysis. While these studies are in 2D culture, the CNs are robust and express several key forebrain markers (FIGS. 47 and 48). To identify the heterogeneity of cell types produced by differentiation, scRNA was performed on one control and one C9orf72 line after 50 days of differentiation (FIG. 48). Following batch normalization, t-distributed Stochastic Neighbor Embedding (tSNE) analysis showed non-biased clustering, which demonstrates that both control and C9orf72 CNs each produce a variety of cell types (FIG. 48). Von Economo spindle neurons (VENs) are particularly vulnerable in FTD (27-29) and express a combination of related deep layer cortical genes (BCL11B, Fezf2, LMO4, NMB and SLC17A7). Cells that co-express combinations of 2-3, 4 and 5 of the VEN-related genes have been identified. The Inventors found ~15% of cells in CN cultures co-express at least 3 VEN-related genes, with no disease bias. Forebrain markers are highly expressed in the CNs, and the cultures are heterogenous mixtures of neurons, neural progenitors and glial cell types (FIG. 49). Expression of hippocampal and hypothalamic genes were low. Additionally, this differentiation generates astrocytes spontaneously after prolonged culture. Here, the Inventors plan to seed the CNs on the MPS after 60 days of differentiation, and to further mature them for 2 weeks before co-culture with other cell types, allowing expression of astrocytes like that shown at day 90 (FIG. 47).

Generating other cell types for co-culture in MPS. Cedars-Sinai also has robust differentiation techniques for the generation of multiple iPSC-derived cell lineages, including brain microvascular endothelial cells (BMECs) and microglia (FIG. 47). In related studies, the Inventors have co-cultured BMECs with iPSC-derived neurons and found the neural cells can survive in the MPS for over 8 weeks and produce appropriate neuronal phenotypes (FIG. 47). While the BMECs have a 2-week survival time, it is possible to re-seed them into the chips if needed and the Inventors continue to optimize this process. In the Inventors' ongoing NIH funded work in developing MPS models of Parkinson's Disease and ALS, the Inventors established seeding and co-culture methods of neurons with either BMECs alone or with astrocytes and microglia. Importantly, much like the CNs, BMECs, astrocytes and microglia can be cryogenically stored in batches for subsequent experiments. After QC validation, frozen lots of BMECs and microglia can be thawed, seeded directly into the MPS, and matured in co-culture with CNs that have been seeded in advance. In addition to the BMECs and astrocytes, microglia (MG) are required for normal neuron development and may play a neuroinflammatory role in FTLD. Protocols to derive functional MG have been established across large cohorts of iPSC lines at Cedars-Sinai (FIG. 47). To best construct the fMPS, the Inventors plan to include the MG as a key component, incorporating potential neuroinflammatory pathways into the Inventors' phenotypic assessment of FTLD-TDP. The Inventors will determine the ideal combination and timing of the cell types during the Inventors' first aim.

Figure 50:
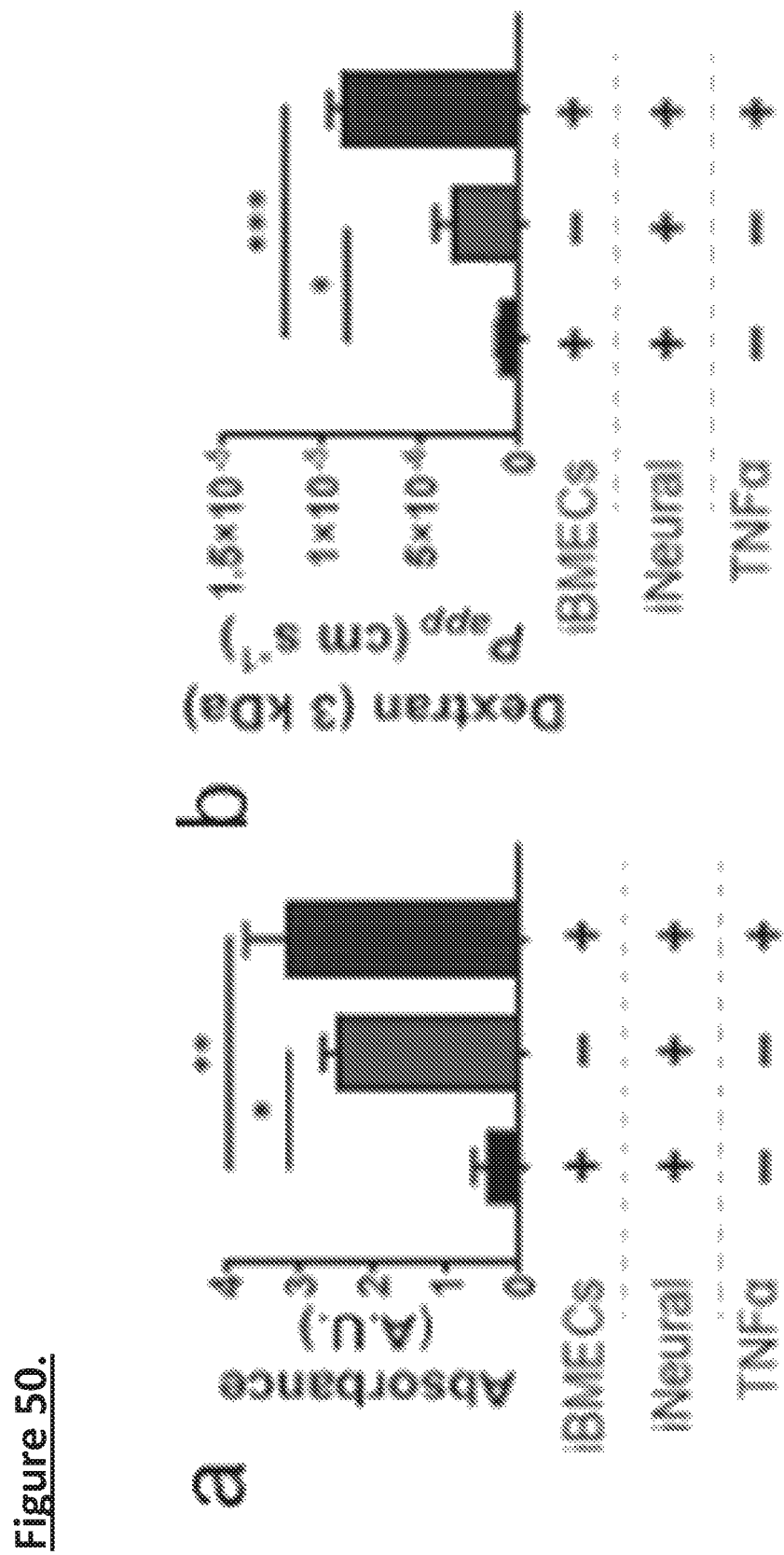
FIG. 50. Functional BBB on MPS. In the presence of whole blood, toxicity (a) and dextran permeability (b) are reduced with co-culture of BMECs.

Application of patient serum samples: Importantly, the Inventors' proposed fMPS model allows evaluation of peripheral serum on cortical cell function, which the Inventors predict will enhance phenotypic and biomarker discovery. The Inventors have already established a BBB MPS model using a mixed neuronal culture in which the Inventors have successfully passed whole human blood through the BMEC channel (FIG. 50). In the Inventors' proposed co-culture of CNs and MG with BMECs in the MPS environment, the Inventors will have a complete, in vitro human representation of the neurovascular unit. Additionally, serum samples have been gathered from the same FTLD-TDP patients from which the fMPS is derived, and the Inventors are able to flow these samples through the system. For the first time, this will allow us to explore the relationship between circulating metabolic and immune factors within the blood and the function of both control and diseased cortical neurons.

Example 23

Developing a Multicellular 3D Human Forebrain MPS and Patient iPSC Lines

Of interest is developing a multicellular forebrain MPS model (fMPS) to study FTLD-TDP. This includes control iPSC lines from the Lothian cohort in Scotland, where patients between 60-80 years of age have been followed for many years and shown to be neurologically normal. One of these lines will be used as a standard control for production of CNs, BMECs, MG, and establishment of the fMPS. The Inventors will use a panel of outcome measures to validate the system with a normal control line, and then examine robustness with an additional 4 control iPSC lines. In parallel, the Inventors will develop a set of C9orf72 and GRN patient iPSC lines and isogenic controls, which will subsequently be used to identify disease biomarkers for FTLD-TDP in SA2 and the UH3 portion of this proposal.

Pursuing the above includes developing 3D fMPS consisting of cortical neurons, glia and BMECs, and validate its stability. Control iPSC-derived CNs will be generated from a single line and seeded into the top channel of the chips after 60 days of differentiation in 2D culture. This timeline takes advantage of the differentiation's gliogenic potential (FIG. 47) resulting in a cortical population comprised of neurons and astrocytes. After 14 days, BMECs will be added to the bottom channel and in a subset of chips, MG will be added to the neuronal chamber. Both channels will have 5-7 µl/hour flow rates, which the Inventors have found optimal for neural and endothelial cell survival and maturation. Cultures will be live-imaged and effluent for LDH and dextran permeability will be collected at weekly intervals after seeding of the neurons to establish overall survival, barrier function and cell-type interactions. Given the MPS design, the Inventors will collect and assay the effluent of both the neuronal and vascular chambers of the device. At two and four weeks of co-culture with BMECs/MGs, fMPS Models are fixed and evaluated for cell population and morphology. To assess cortical neuron physiology, the Inventors will use Ca2+ imaging at each time point. The co-culture paradigms will be scored depending on four essential parameters to determine feasibility for future studies: (i) calcium transient activity for neuron function, (ii) immunostaining to determine co-culture stability, (iii) cellular morphology to determine neuronal and glial establishment, and (iv) BBB function and cell toxicity for assessment of the neurovascular unit. Successful scores will be determined by high calcium transient activity, adequate distribution of all cell types, neuronal morphology that allows for adequate imaging analysis, and low LDH and dextran levels in the neuronal compartment. These experiments will be repeated three times to assess variability between runs using the same batch. From these studies the Inventors will select the optimum timing and seeding conditions for the co-culture fMPS model. As the Inventors' first Go/No-Go criteria, the Inventors must achieve a stable, multicellular fMPS model before advancing to the next sub aim. Establishing the optimal seeding density and timing of the control-derived cells, which results in consistent barrier and toxicity performance, coupled with ICC data demonstrating the presence of all three cell types at endpoint, is the Inventors' milestone criteria. To see a full description of the Inventors' milestones and criteria, please refer to the end of this research strategy section.

Example 24

Determining Robustness of Biomarkers/Assays in Measurement of the MPS

Based on the highest scoring co-culture paradigm, the Inventors will expand the Inventors' henotypic outcome measures to include a comprehensive matrix of cellular assays that utilizes the multidisciplinary cell physiology readouts established at Cedars-Sinai. The following will be assessed at weekly intervals post-CNs, or for terminal analyses, after four weeks in co-culture: effluent will be profiled for metabolomic biomarker expression of neurotransmitters and metabolites with mass spectrometry (i), and for cytokine production using ELISA (ii); neuronal physiology will be analyzed using live calcium imaging (iii), MPS devices will be analyzed post-experiment to assess the morphology and survival of cell types using high content imaging (iv). Cell toxicity and BBB permeability will still be measured using LDH and dextran cross-over in the neuronal compartment. The Inventors have carefully considered complementary assays for the same sets of chips to reduce overall chip requirements. To establish the reliability of this system, these experiments will be repeated 3 times using the same control iPSC line-derived cell lots that have been generated together in SA1.1, for a total of 18 fMPS to compare. In each assay, the Inventors will compare results and determine the validity of the model based on a coefficient of variation (CV) that is less than 25% per measurement. For example, the control fMPS is reliable in modeling cell toxicity (or reliable in showing no significant toxicity is observed) if the LDH values are within a variance of 25% across the 5 chips per run, and the means of each of the 3 experiments are not significantly different. The Inventors will apply the appropriate statistical tests to account for repeated measurements and submit all data to the biostatistics core at Cedars-Sinai for verification. When the Inventors determine that these assays produce results that are not significantly different between the 3 runs (5 replicates per run), the Inventors will move on to evaluating the fMPS model derived from 5 separate control individuals.

Example 25

Figure 51:
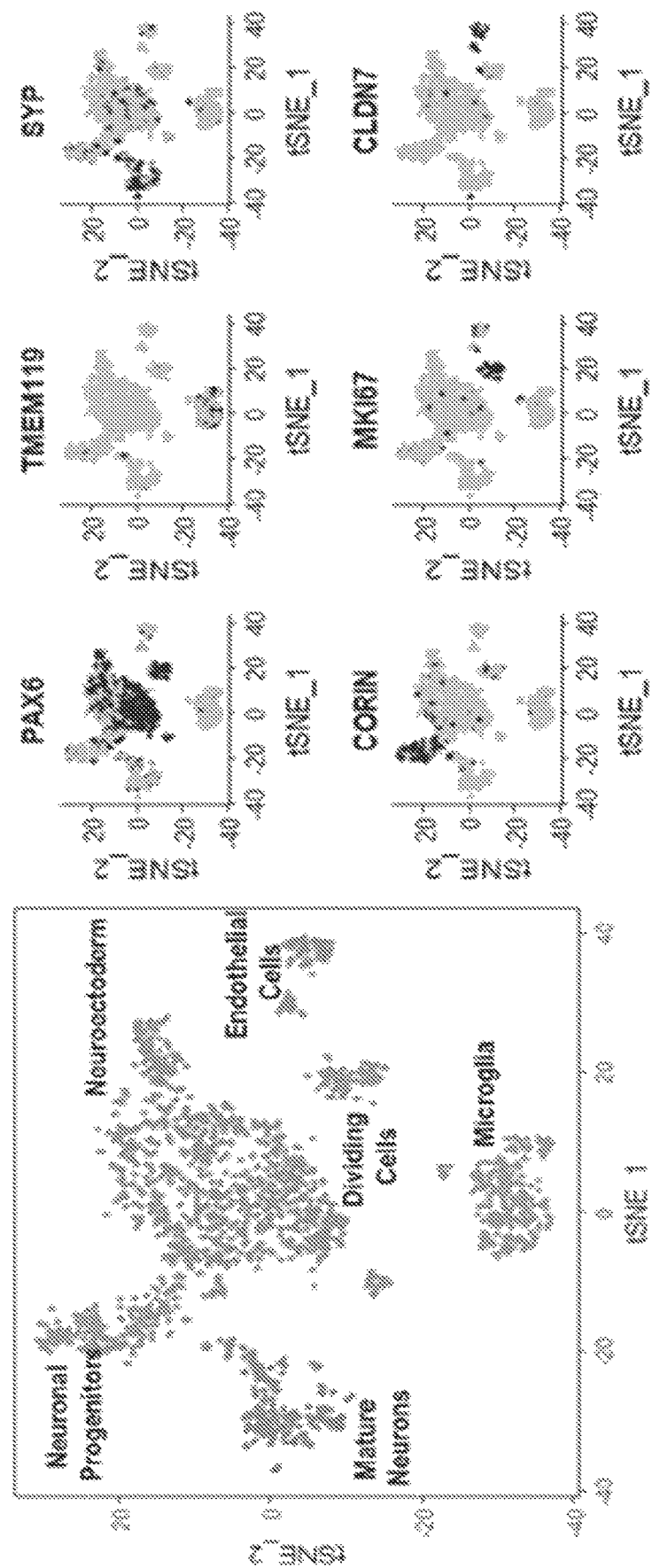
FIG. 51. Co-cultured cell types isolated from MPS are identified by scRNA. The top (midbrain neurons & MG) and bottom (BMEC) chambers are pooled for analysis by scRNA. Unbiased clustering of cells identifies six putative population (left). Specific genes representative of neurons, microglia, neural progenitors, proliferative cells and endothelial cells (right).

Identify Biomarkers that are Reproducible Across fMPS from 5 Control Individuals Before this system can be used to detect disease-specific changes for FTLD-TDP, the Inventors must establish what variance exists between different human subjects. Here the Inventors focus on the most robust assays from SA1.2a and examine variability across 5 control fMPS (Table 5). Additionally, a single fMPS per line will be allotted for single-cell RNA transcriptomic profiling (scRNA) to explore cell types that are consistently expressed in these devices. Preliminary data from the Inventors' studies of midbrain neurons co-cultured in MPS with MG and BMECs show application of scRNA, and recovery of co-cultured cell types (FIG. 51). The Inventors plan to apply the same approach to the Inventors' fMPS to aid in evaluation of cell type variation within the model. fMPS chips which meet a minimum threshold of cell survival after 4 weeks will be included in analysis of interline variability. Assays that result in reproducible biomarkers and readouts, which have a CV no greater than 25% across the 5 controls, will be selected for application as control measures. To reduce potential sources of biological variability in later aims, the Inventors will select the control-BMEC line that produces the highest barrier score of the 5 control MPS. This line will be used for the BBB chamber of disease chips, while the CN and MG will both be derived from each FTLD-TDP line. The biomarkers the Inventors choose to move forward for future disease analysis should show no greater variance than 25% CV between runs. Establishing a low coefficient of variation between control fMPS model subjects, specifically at 25% or less within lines and 30% or less across lines, will be the Inventors' second Go/No-Go criterion for advancement. This represents the usability of the Inventors' multicellular fMPS design for screening applications.

Example 26

Generate iPSC Lines from FTLD-TDP Subjects with C9orf72 (8) and GRN Mutations

The UCSF Memory and Aging Center has collected highly characterized FTLD-TDP patient samples in addition to cells for iPSC reprograming. These include measures of disease phenotype ranging from clinical scales, serial neuroimaging, brain pathology and biospecimens. Utilizing the iPSC Core at Cedars-Sinai, the Inventors will generate iPSC lines from FTLD-TDP subjects from which a complete collection of clinical, biospecimen and autopsy material are available. Therefore, the Inventors have the unique opportunity to validate FTLD-TDP fMPS results with individual clinical and pathologic data. This includes serum collected from these patients for blood/brain fMPS interactions, and post mortem forebrain tissue already being used for single-nuclei RNA sequencing by the Seeley laboratory. Additionally, as these FTLD-TDP iPSC lines are being produced by the iPSC Core, they can immediately enter differentiation of CNs and MGs, which can then be cryopreserved and stored for direct use. Lines will be generated from both males and females to account for sex as a biological variable, although the Inventors do not anticipate significant differences in terms of fMPS phenotypes.

Example 27

Figure 52:
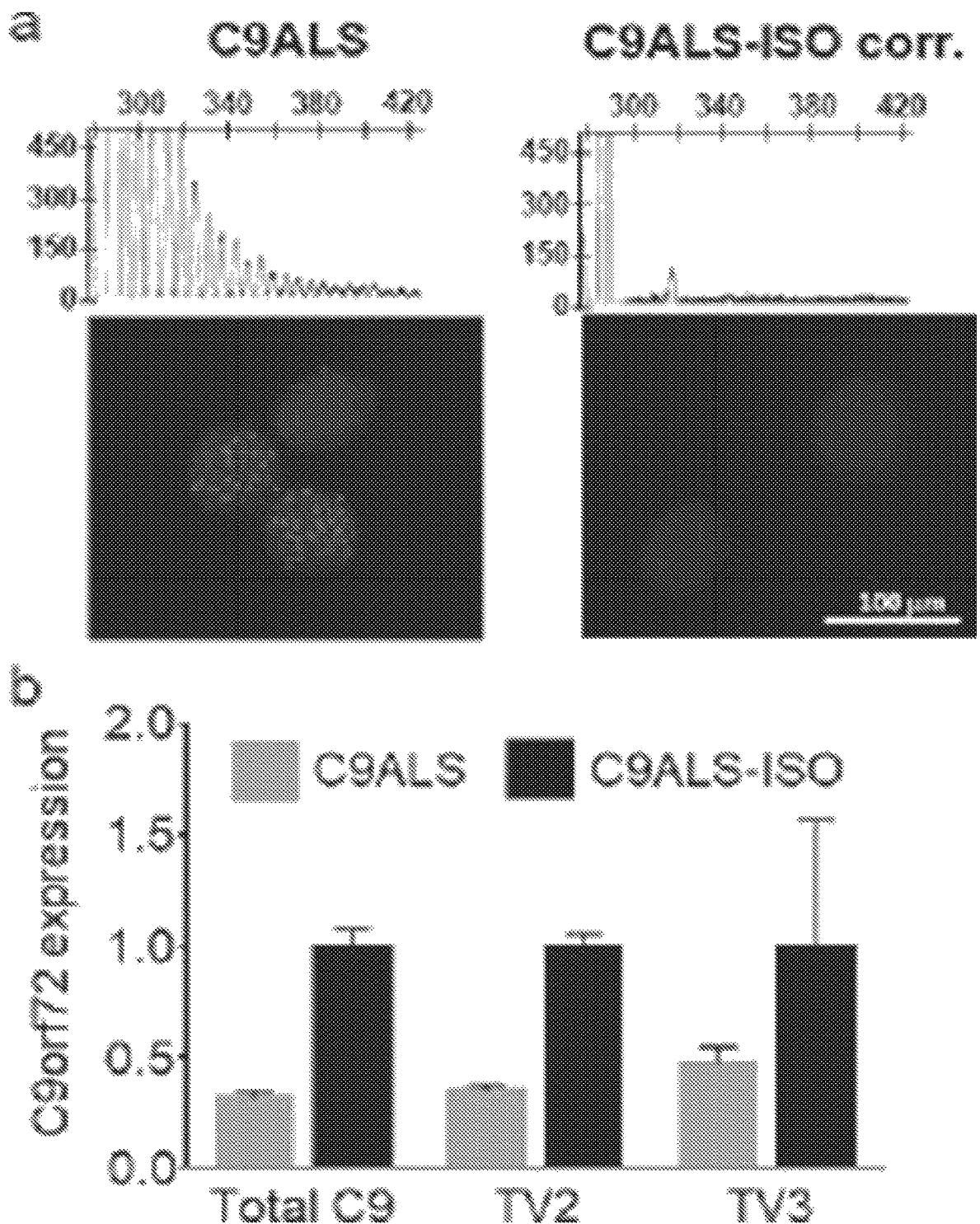
FIG. 52. C9orf72-corrected line has no RNA foci and rescued expression of C9orf72. (a) Repeat primed PCR of parental and corrected line. (b) RNA foci are absent in correction. (c) C9orf72 total and transcript variants (TV2&3) returns to normal.

Generate C9orf72 and GRN Isogenic Corrected iPSC Lines Using CRISPR Gene Editing The Inventors have already removed the repeat expansion in the C9orf72 gene in three ALS patient-derived iPSCs, restoring normal C9orf72 gene expression, and halting production of RNA foci and RAN dipeptides in iPSC-derived neurons (FIG. 52). Likewise, using CRISPR/Cas9 technology, the Inventors have restored the normal coding sequence to missense and nonsense alleles of gene such as those seen in GRN. The Inventors will use these already established approaches to develop isogenic controls for three C9orf72 and three GRN iPSC lines generated. The lines will be karyotyped, passaged and matched with the parent lines as they are expanded. Preliminary differentiation to forebrain neurons will be established prior to use in the chips.

Example 28

Characterize fMPS Models for Disease-Related Biomarkers in Two Common Genetic Forms of FTLD-TDP Differences attributed to FTLD-TDP lines. Here, the Inventors expand the Inventors' assays to include the detection of potential biomarkers and/or phenotypes that are associated with FTLD-TDP-derived tissues. The Inventors first propose to use disease and isogenic corrected lines to minimize inter-individual variability in biomarkers and phenotypes in the Inventors' assays. The Inventors will next apply the fMPS and assays to a larger cohort of FTLD-TDP patient lines to determine whether the biomarkers are reproducible and representative of disease heterogeneity. Identification of biomarkers and confirmation of the biomarkers leads to the Inventors cross-validate the system with human data, conduct preclinical efficacy testing of candidate therapeutics using identified biomarkers, and examine the effect of flowing patient serum on the fMPS for potential diagnostic application.

Based on the above, one can use a set of iPSC lines from C9orf72 and GRN subjects vs. isogenic controls to identify disease-associated phenotypes and biomarkers in the fMPS. Building upon the Inventors' studies in SA1, the Inventors will generate diseased fMPS models in parallel with isogenic controls and evaluate the biomarker and phenotypic readouts. Three C9orf72 and three GRN disease and corresponding isogenic lines will be used for derivation of CNs and MG, resulting in 6 sets of CN and MG to produce patient-specific neural compartments. The BMECs for each fMPS will be derived from the highest-scoring control line, determined. As C9orf72 expansion lines in combination with isogenic controls will be used, the Inventors will evaluate disease-specific biomarkers such as RNA foci and RAN dipeptide production. In the GRN MPS models, the Inventors will monitor levels of GRN protein and lysosomal function, and in both the Inventors will screen for phosphorylated TDP-43 inclusions. Importantly, measures of GRN protein and DPR production can be made from the effluent and can be correlated over time with changes in novel biomarkers. Single-cell RNA-seq experiments will allow us to directly compare the transcriptomic profiles of the same individual cell type, such as VEN neurons, between control and disease fMPS, and determine if cortical cell development is affected. To evaluate immunological components of FTLD-TDP, the morphology of the MG will be evaluated using confocal microscopy and expression of specific transcripts indicative of disease associated microglia (DAM). In 2D, and without co-culture, the Inventors have found that familial AD patient iPSC-derived MG differentially express transcripts associated with the DAM phenotype (not shown). The Inventors anticipate that the Inventors' proposed multicellular fMPS model will promote changes in diseased MG and that altered cytokine secretion will be detected in the effluent by ELISA or mass spec. Putative disease-specific biomarkers will be ranked by significance and reproducibility, and statistically significant biomarkers will be pursued.

The above leads to study of robustness of disease biomarkers across the larger group of FTLD-TDP patient iPSC lines with mutations in C9orf72 and GRN vs. normal controls. After establishing differential disease-associated biomarkers and phenotypic readouts, the Inventors will apply the fMPS disease model to the Inventors' complete cohort of FTLD-TDP subjects. As some phenotypes/biomarkers samples which the Inventors can then apply during the proof-of-concept application of the fMPS in diagnostic capabilities. With the increased pool of disease-associated fMPS, the Inventors will confirm the utility of the biomarkers and determine whether phenotypes or biomarkers are conserved across C9orf72 and GRN patient-derived fMPS models compared to normal controls. Completion of SA2.2 defines the final Go/No-Go criterion of the proposal: Only if the Inventors detect differential expression of biomarkers from the disease vs isogenic-corrected fMPS and across the broader patient group, will the Inventors continue to the UH3 phase of the proposal.

Figure 53:
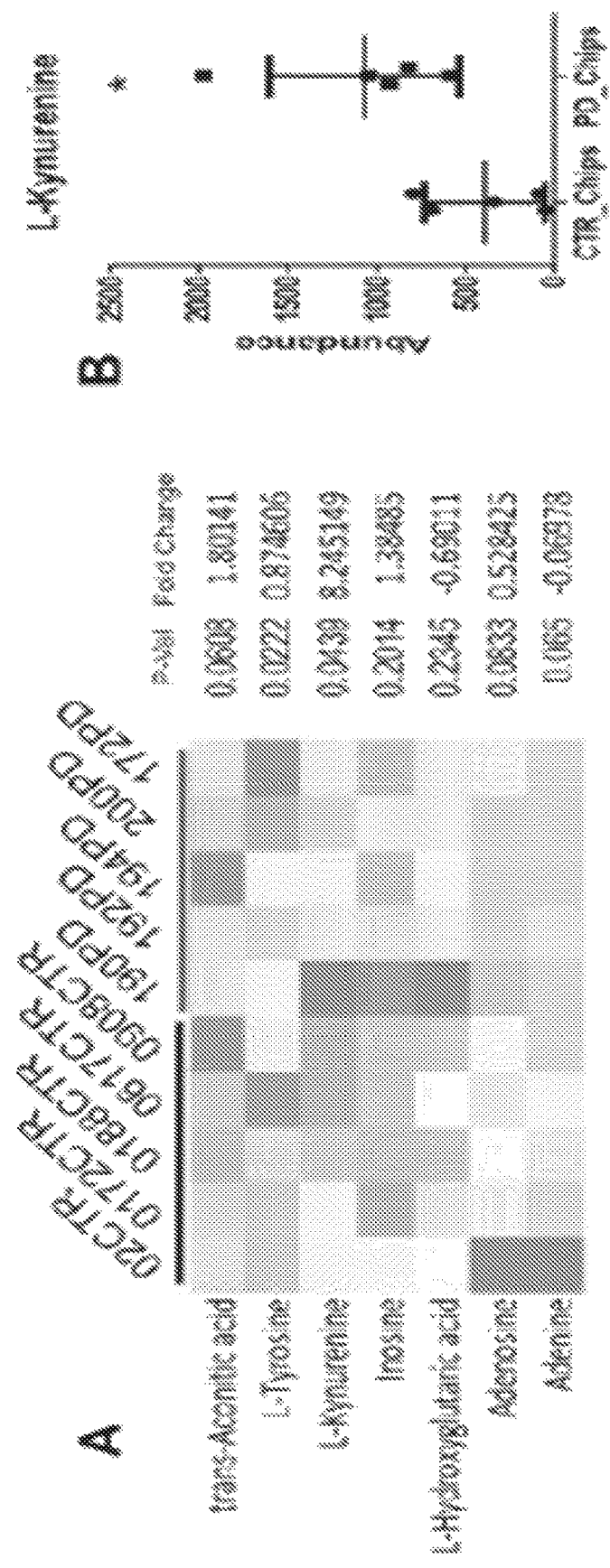
FIG. 53. Difference in metabolites detected from midbrain MPS of PD vs CTR (a) Heatmap of metabolites differentially detected between 5 control and 5 PD midbrain MPS models. (b) L-Kynurenine is more abundant in effluent from PD compared to CTR MPS.
Figure 54:
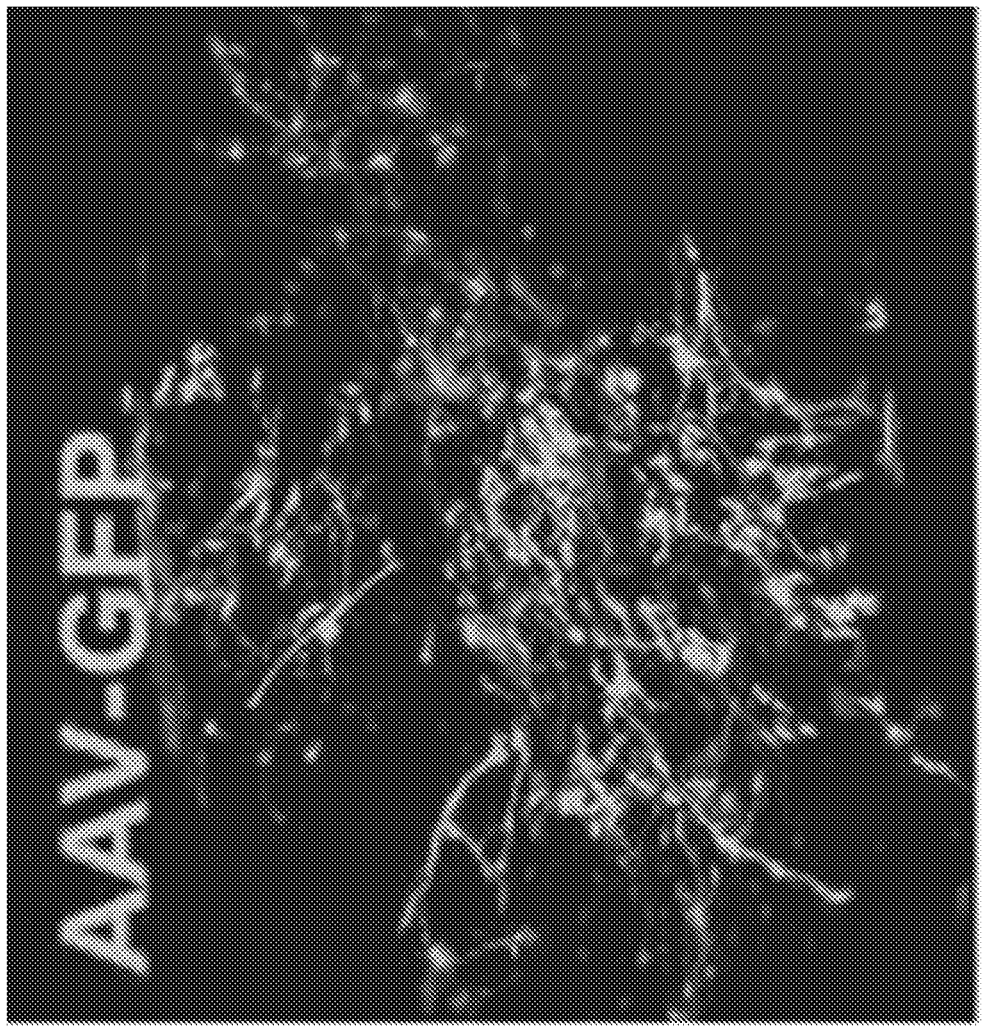
FIG. 54. MPS neurons 6 days after treatment with AAV-GFP.

The Inventors expect to see biomarkers specific to FTLD-TDP that are predicted from prior 2D culture studies, but the majority will be novel biomarkers. With the Lothian control cohort, the Inventors do not expect to see confounding biomarker signals in this group (i.e. control patients who would have developed FTLD-TDP pathology). The Inventors have recently demonstrated that iPSC-derived dopamine neurons from patients with early onset Parkinson's Disease (PD) show differences in metabolite signatures in the Inventors' midbrain MPS model (FIG. 53). In fact, using a sample size of a single MPS per 5 control and 5 PD lines, the Inventors identified significant fold changes in several metabolites, two shown here (FIG. 53). Therefore, the Inventors anticipate that application of metabolomics to the diseased effluent in a controlled culture system will reveal differences in FTLD-TDP as well, particularly with the larger disease and control cohort of lines for comparison.

After biomarker discovery, one can evaluate clinical measures and single nuclei RNA data from FTLD-TDP subjects and tissue. One can validate FTLD-TDP MPS models by comparing disease model findings to clinical and pathologic measures in humans. To this end, the Inventors have chosen to use a completely characterized set of FTLD-TDP subjects on which clinical data and post-mortem cortical tissue has been collected. In this way the Inventors can not only investigate disease-state properties of the microfluidic forebrain model (TDP-43 proteinopathy, glial activation states, cell death), but the Inventors can also compare these findings with individual patient data.

Of further interest is defining cortical and cellular vulnerability in FTLD-TDP and has an ongoing project to determine pathologic changes at the single-cell level in FTLD-TDP cortex. Nuclei from the frontoinsular and primary motor cortex of frozen, post-mortem tissues will be processed for single-nuclei sequencing of RNA (snRNA) as part of his already funded proposal which adapts an already published protocol. This data set, combined with the Inventors' fMPS-generated scRNA data set, allows the unique opportunity to compare single cell transcriptomic profiling data between an in vitro model and patient tissue from the same individuals. The Inventors will compare the profiles of patient snRNA with the fMPS scRNA and develop a normalized expression matrix of each data set to assist in identification of different cell populations. In the cell populations identified across datasets, the Inventors will describe both conserved and divergent gene pathways and transcriptomic signatures. Gene set enrichment analysis will also be used to directly interrogate data from cortical neurons, astrocytes, microglia and BMECs, which the Inventors expect to be represented in both data sets.

Example 29

Assess Therapeutic Response of Biomarkers to Genotype-Specific Modifiers Including Antisense Oligonucleotides to C9orf72, and Gene Replacement with AAV-GRN Biomarker discovery may suggest therapeutics for FTD/ALS spectrum disorder targeting specific genetic variants are entering clinical trials, they are presently focused on ALS rather than FTD. This is largely because the fast progression rate of ALS makes clinical trials using functional rating scales feasible without biomarkers, whereas this is not possible in FTD. This emphasizes the importance of this proposal, specifically the identification and validation of novel biomarkers for FTLD-TDP. The Inventors' findings would have immediate translational impact, as biomarkers identified using fMPS models could be used to design and monitor trials of gene therapy for FTD patients and would also be expected to be useful for therapeutic trials in sporadic FTD. Therefore, in this aim the Inventors will investigate the effect of two therapeutic approaches for FTLD-TDP currently under development and determine their ability to modify biomarkers in fMPS models of C9orf72- and GRN-related FTD.

Antisense oligonucleotides (ASOs) to C9orf72 and AAV-GRN for FTLD-TDP: Blocking the production of toxic RNA and protein species caused by the repeat expansion in the C9orf72 gene has been shown to have therapeutic effects in iPSC and animal models of FTD/ALS. Mutations in GRN that cause FTLD-TDP uniformly lead to loss of function and haploinsufficiency, indicating that gene replacement is a viable therapeutic approach. Here, the Inventors will generate 4 C9orf72 and 4 GRN MPS chips as before, selected from the larger cohort based upon model stability. The Inventors will then flow ASOs to C9orf72 fMPS, or AAV-GRN to GRN fMPS, through the neuronal compartment to mimic intrathecal administration via the CSF, and to determine whether biomarkers show improvement. For ASO experiments the Inventors will compare ELISA for DPR production from the effluent as a positive control, and for AAV-GRN the Inventors will do the same for GRN levels.

In this way the Inventors have an internal control for target engagement, relative to biomarker correction. ASOs and AAV will be provided by the Inventors' collaborators at Ionis (letter from Frank Bennett) and Avexis (letter from Brian Kaspar), with whom the Inventors have a strong track record of collaboration and publication. Importantly, with the fMPS the Inventors can examine the effluent across a time course of 12 hour intervals to both characterize time-to-therapeutic effect and duration of the effect. Once the Inventors confirm an effect by administration through the neuronal chamber, the Inventors will then administer the ASOs or AAV-GRN through the blood chamber to test delivery by peripheral administration and BBB permeability. Again, assays for altered biomarkers identified earlier will be conducted as outlined in Table 9. To control for potential off-target or cytotoxic effects of the ASOs and AAV, the Inventors will conduct mirrored experiments using scrambled ASOs and AAV-GFP passed through the neuronal side on the diseased fMPS models. The Inventors will also evaluate the effects ASOs to C9orf72 and AAV-GRN on 3 control-derived MPS chips. Importantly, when reversal of a biomarker or phenotype is observed after treatment, the Inventors will evaluate exactly which cell types in the fMPS are "corrected" and lead to a rescue.

Example 30

Characterize Effects of Flowing FTLD-TDP Serum in fMPS Models

FTLD-TDP patients across all genotypes show a higher incidence of autoimmune diseases; GRN levels are linked to obesity and insulin resistance and FTLD-TDP subjects with GRN mutations have elevated levels of circulating IL-6. C9orf72 and GRN proteins are also highly expressed in peripheral myeloid cells of the innate immune system, and work from the Inventors' group and others strongly supports that loss of function of these proteins leads to altered immune cell function. This raises the possibility that neurodegeneration in FTLD-TDP involves an interplay between metabolic and/or immune factors in the peripheral blood and the forebrain tissue. In addition to toxicity testing or pre-screening of therapeutic efficiency, the Inventors' fMPS is uniquely capable of being used as a biological readout for evaluating these circulating factors in patient samples. This would be an ambitious application of the device, and so here the Inventors propose to first establish the application of the fMPS when exposed to FTLD-TDP serum. Using the appropriate control experiments in parallel, the Inventors will test if FTLD-TDP patient serum elicits disease phenotypes in control fMPS models. The Inventors hypothesize that factors from serum will influence the function of BMECs, microglia, astrocytes and unprecedented ability to examine serum from the same patients from which the iPSCs were generated and the fMPSs were seeded. This will then set the stage for using fMPS models for screening large number of patient sera for effects of peripheral factors on cortical function and examining drug delivery across the BBB.

Based on the above, one can examine the effect of flowing serum from controls vs. FTLD-TDP patients on disease biomarkers in fMPS to determine impact of circulating factors on disease phenotype. The Inventors will use 3 control, 3 C9orf72 and 3 GRN patient-derived fMPS sets which showed the most stability and robust measurement of biomarkers in SA2, and the Inventors will establish the effects of flowing (i) media with IL-6 to establish a positive control response to a pro-inflammatory cytokine in the neuronal compartment, (ii) healthy control serum to account for differences caused by serum proteins and (iii) serum from the respective FTLD-TDP subjects to develop a range of potential differences. Once the Inventors evaluate the effects of flowing human serum through the fMPS, either control or patient-matched disease, the Inventors will test the effects of FTLD-TDP serum on 3 control-derived fMPS. The serum chosen will be from the FTLD-TDP patient (either C9orf72 or GRN) in which the Inventors observe the greatest enhancement or expression of disease phenotypes. The Inventors will examine the brain and serum effluents as described above. After administration of IL-6 or serum, effluent from the neuronal chamber will be tested every 12 hours for cytokine production, and either DPR or GRN release with respect to the FTLD-TDP tissue fMPS. At the end of the experiment (5 days of serum flow) MPS will be collected and assessed for markers including those for microglial and astrocyte activation.

These experiments will determine the impact of serum flow in fMPS models, and whether components from FTLD-TDP serum will produce disease related biomarkers. Using IL-6 as a positive control, the Inventors will determine whether a cascade of signaling alterations occur in microglia, astrocytes and neurons in response to a circulating pro-inflammatory factor, and whether inflammation exacerbates FTLD-TDP related fMPS biomarkers. Additionally, the Inventors will determine whether serum factors from FTLD-TDP patients influence disease biomarkers in fMPSs derived from control or FTLD-TDP. If a major influence of FTLD-TDP patient serum is observed, then follow up studies identifying serum components will be performed.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the compositions and methods related to induced pluripotent stem cells (iPSCs), differentiated iPSCs including neurons, vascular cells, support cells such as microglia and astrocytes, methods and compositions related to use of the aforementioned compositions, techniques and composition and use of solutions used therein, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of culturing cells, comprising:
providing
  (i) astrocytes and brain microvascular endothelial cells (BMECs),
  (ii) neurons,
  (iii) microglia, and
  (iv) a microfluidic device comprising a membrane comprising a top surface and a bottom surface;
seeding the BMECs on the bottom surface to create seeded endothelial cells and seeding the astrocytes on the top surface to create seeded astrocytes, the BMECs and astrocytes being seeded simultaneously;
seeding neurons on the top surface one or more days after seeding the BMECs and astrocytes to create seeded neurons;
seeding microglia on the top surface at one week to create seeded microglia; and
culturing the seeded endothelial cells, seeded astrocytes, seeded neurons and seeded microglia under flow conditions at a flow rate for a period of time.

2. The method of claim 1, wherein the astrocytes, BMECs, neurons and microglia are each differentiated from stem cells.

3. The method of claim 1, wherein seeding neurons is one or more six days after seeding BMECs.

4. The method of claim 1, further comprising detecting tight cell-to-cell junctions, and/or further comprising measuring neuron or astrocyte activity by at least one of patch clamp measurements, extracellular electrophysiology measurements, imaging using calcium-sensitive dyes or proteins, or imaging using voltage-sensitive dyes or proteins.

5. The method of claim 1, wherein the top surface of the membrane comprises part of a top microfluidic channel and the bottom surface of the membrane comprises part of a bottom microfluidic channel, and the top microfluidic channel and the bottom microfluidic channel each comprise at least one inlet port and at least one outlet port, and culture media enters the inlet port and exits the outlet port.

6. The method of claim 1, wherein the neurons are derived from induced pluripotent stem cells from a human patient diagnosed with a neurodegenerative disease.

7. The method of claim 6, wherein the neurodegenerative disease is Amyotrophic lateral sclerosis (ALS), Parkinson's disease (PD), Huntington's disease (HD), or Alzheimer's disease (AD).

8. The method of claim 1, wherein the neurons are spinal motor neurons or dopaminergic neurons.

9. The method of claim 8, wherein the spinal motor neurons or dopaminergic neurons are cultured under the flow conditions comprising flow of culture media at a flow rate for at least three weeks.

* * * * *